United States Patent
Antebi et al.

(10) Patent No.: US 11,573,231 B2
(45) Date of Patent: Feb. 7, 2023

(54) BIOMARKER OF AGING

(71) Applicant: Max-Planck-Gesellschaft zur Forderung der Wissenschaften e.V., Munich (DE)

(72) Inventors: Adam Antebi, Bonn-Bad-Godesberg (DE); Varnesh Tiku, Cologne (DE); Pieternella Slagboom, BB Woubrugge (NL)

(73) Assignee: Max-Planck-Gesellschaft zur Forderung der Wissenschaften e.v., Munich (DE)

( * ) Notice: Subject to any disclaimer, the term of this patent is extended or adjusted under 35 U.S.C. 154(b) by 579 days.

(21) Appl. No.: 16/490,184

(22) PCT Filed: Mar. 2, 2018

(86) PCT No.: PCT/EP2018/055229
§ 371 (c)(1),
(2) Date: Aug. 30, 2019

(87) PCT Pub. No.: WO2018/158454
PCT Pub. Date: Sep. 7, 2018

(65) Prior Publication Data
US 2020/0072840 A1 Mar. 5, 2020

(30) Foreign Application Priority Data
Mar. 2, 2017 (WO) .................. PCT/EP2017/000297

(51) Int. Cl.
*C12Q 1/68* (2018.01)
*G01N 33/573* (2006.01)
*C12Q 1/686* (2018.01)

(52) U.S. Cl.
CPC ........... *G01N 33/573* (2013.01); *C12Q 1/686* (2013.01); *G01N 2333/91011* (2013.01); *G01N 2800/7042* (2013.01)

(58) Field of Classification Search
None
See application file for complete search history.

(56) References Cited

PUBLICATIONS

Sinclair et al. (Annu Rev Microbiol, 1998, 52:533-60) (Year: 1998).*
Tschentscher et al. (Cancer Research, 2003, 63:2578-2584) (Year: 2003).*
Goasguen et al. (Leukemia Research, 1999, 1133-1140) (Year: 1999).*
Sinclair et al. (Science, 1997, 277:1313-1317) (Year: 1997).*
International Search Report and Written Opinion for International Patent Application No. PCT/EP2018/055229 dated Jul. 26, 2018, 16 pages.
Xia et al., Molecular and phenotypic biomarkers of aging [version 1; peer review: 3 approved], F1000Research2017, 6 (F1000 Faculty Rev):860 Last updated: Jul. 17, 2019.
Demontis et al., Intertissue Control of the Nucleolus via a Myokine-Dependent Longevity Pathway, Cell Reports, vol. 7, No. 5, Jun. 1, 2014 (Jun. 1, 2014), pp. 1481-1494.

* cited by examiner

*Primary Examiner* — Stephanie K Mummert
(74) *Attorney, Agent, or Firm* — Amin, Turocy & Watson, LLP

(57) ABSTRACT

The present invention relates to a marker that can be used as aging biomarker. More specifically, the present invention relates to the analysis of nucleolar size as a biomarker for aging and metabolic health and its relation to the virtual age, or the life expectancy of animals, including humans. The aging biomarker of the invention can be used to study the effect of medication, food compounds and/or special diets on the wellness and virtual age, or the life expectancy of animals, including humans.

5 Claims, 46 Drawing Sheets a b a

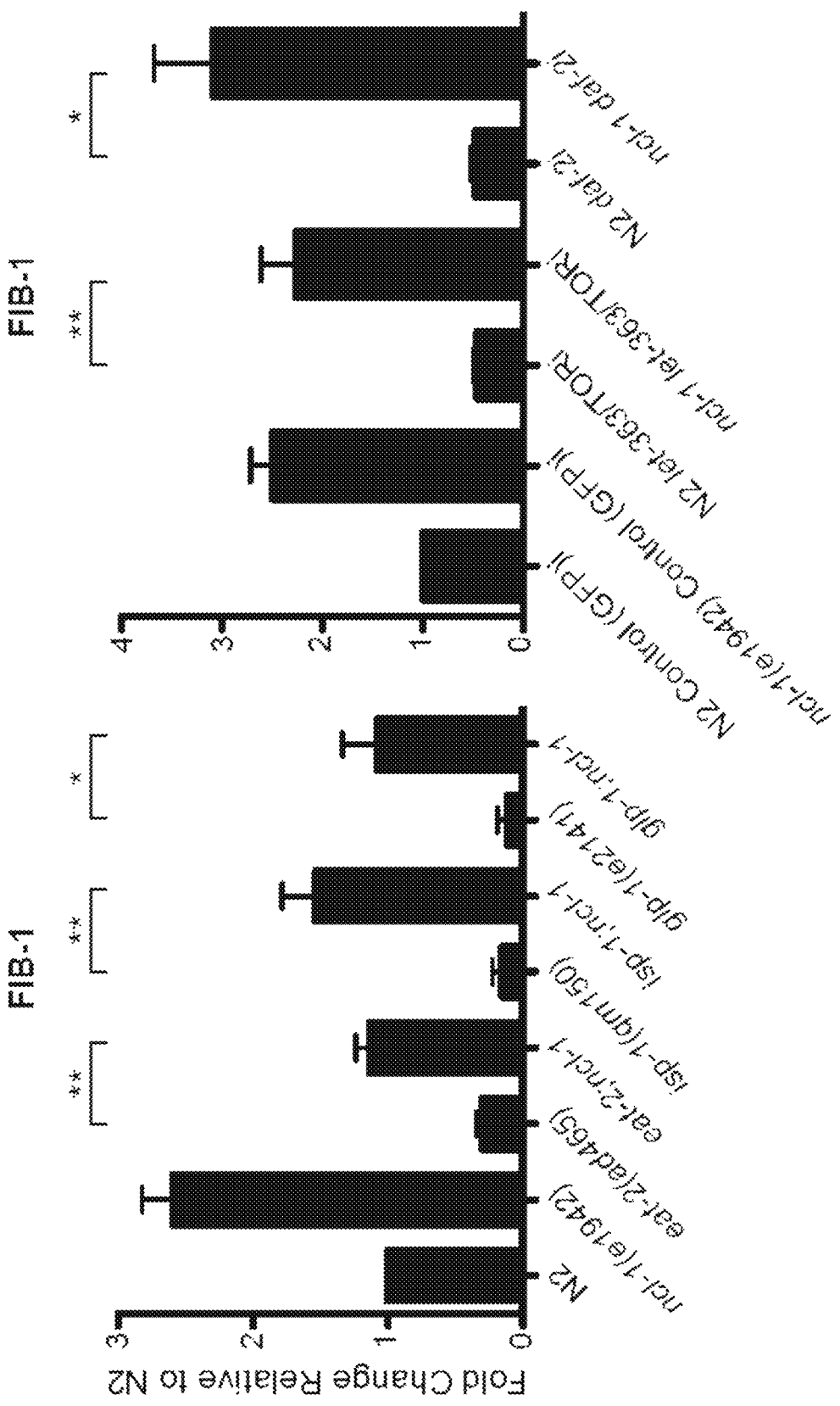

C

FIBRILLARIN/DAPI

Ad libitum     DR

Kidney

Wildtype     IRS1 KO

Kidney a b

A

S. aureus

B

E. faecalis

D

Uninfected THP1 macrophages

S. aureus infected THP1 macrophages (24 HPI)

E

A

B

C

D

A

A

B

BIOMARKER OF AGING

SPECIFICATION

The present invention relates to a marker that can be used as aging biomarker. More specifically, the present invention relates to the analysis of nucleolar size as a biomarker for aging and metabolic health and its relation to the virtual age, or the life expectancy of animals, including humans. The aging biomarker of the invention can be used to study the effect of medication, food compounds and/or special diets on the wellness and virtual age, or life expectancy of animals, including humans.

BACKGROUND OF THE INVENTION

Over the last several decades, studies in model genetic organisms have revealed that animal lifespan is plastic and regulated by evolutionarily conserved signaling pathways. These pathways include reduced insulin/IGF and mTOR signaling, reduced mitochondrial function, dietary restriction mediated lifespan, and signals from the reproductive system, which act through specific constellations of transcription factors to extend life. Whether they converge on common regulators or shared downstream processes, however, has remained largely an open question. One process universally required across the major lifespan pathways is autophagy, the turnover of cellular components through lysosomal degradation. Accordingly, a key transcriptional regulator of autophagy, HLH-30/TFEB has been shown to be responsible to extend life in various *C. elegans* lifespan pathways. More recently, it was shown that the Mondo complexes also do so, as part of an extensive HLH transcriptional network together with HLH-30/TFEB. However, the full extent of this regulatory tier and the precise relationship to downstream processes remain poorly understood. A related question is whether there are common causal biomarkers of aging. Considerable efforts have been invested to identify biomarkers predictive of biological age, including physiologic readouts, metabolic parameters, glycomic profiles and others. Nevertheless, markers with strong predictive power, and those proximal to the process of aging have remained elusive. More recently, the discovery of a DNA methylation clock, which monitors changes in hundreds of sites across the genome, has been used to robustly predict human chronological age, as well as aspects of biological age, but the functional and physiologic significance of this remains obscure. The nucleolus is a nuclear subcompartment where ribosomal RNA is synthesized and assembled into ribosomal subunits. It is a dynamic organelle subject to inputs from growth signaling pathways, nutrients, and stress, whose size correlates with rRNA synthesis. The nucleolus is also a production site for other ribonucleoprotein particles, including various splicing factors, the signal recognition particle, stress granules and the siRNA machinery. It thus can be thought of as a central hub of protein and RNA quality control and assembly.

BRIEF SUMMARY OF THE INVENTION

The objective of the present invention is to provide biomarkers of aging with strong predictive power. This goal is achieved by identification of nucleoli size as a cellular hallmark of lifespan and metabolic health conserved across taxa.

Within the present invention, it was possible to show that NCL-1/TRIM2/Brat tumor suppressor extends lifespan and limits nucleolar size in the major *C. elegans* lifespan pathways, as part of a convergent mechanism focused on the nucleolus. Animals representing distinct lifespan pathways exhibit small nucleoli, and decreased expression of rRNA, ribosomal proteins, and the nucleolar protein fibrillarin, dependent on NCL-1. Fibrillarin itself is a causal factor whose knockdown reduces nucleolar size and extends lifespan. In the present invention, it was surprisingly possible to show, that among wildtype *C. elegans*, individual nucleolar size varies, but is highly predictive for lifespan ($R^2=0.93$). Long-lived dietary restricted fruit flies and insulin-like-peptide mutants also exhibit reduced nucleoli and fibrillarin expression. Similarly, tissues derived from longlived dietary restricted and IRS1 knockout mice, and humans who undergo modest dietary restriction coupled with exercise display reduced nucleoli. It is therefore, possible to conclude that small nucleoli are a cellular hallmark of lifespan and metabolic health conserved across taxa.

The invention refers particularly to an ex-vivo or in vitro method for use of nucleolar size as a biomarker for aging and metabolic health. Thereby the term metabolic health refers especially to glycemic and lipid homeostasis but also to a profile comprising insulin sensitivity, fitness and body weight. Several organs, such as liver, adipose tissue and muscles, hormones (insulin, glucagon) and enzymes influence the metabolic health and work together to digest, absorb, process, transport, and excrete the nutrients.

The invention relates also to an in vitro method for use of nucleolar size as a biomarker for aging and metabolic health, wherein the nucleolar size is used as a biomarker for aging or metabolic health in humans. Thereby virtual age, or the life expectancy is higher the smaller the nucleolar size is. In addition to the nucleolar size further biomarker for aging can be determined which are selected from the group comprising fibrillarin, TRIM2/3 (respectively NCL-1), as well as the amount of ribosomal proteins and rRNA.

Another embodiment of the present invention refers to an in vitro method for determining the virtual age, or the life expectancy of animals, comprising provision of a sample containing nucleoli, the analysis of the size of the nucleoli, and finally determination the virtual age, or the life expectancy according to the size of the nucleoli. Thereby the virtual age, or the life expectancy is higher the smaller the nucleolar size is.

Further advantageous embodiments, aspects and details of the invention are evident from the depending claims, the detailed description, the examples and the figures.

DETAILED DESCRIPTION OF THE INVENTION

Work in model organisms has revealed that animal lifespan is regulated by conserved metabolic signaling pathways, which work through specific transcription factors to extend life. Whether these pathways affect common downstream mechanisms remains largely elusive. The inventors could identify the nucleolus as a convergent point of regulation of major lifespan pathways across species. The inventors could reveal that several *C. elegans* lifespan pathways impinge on regulators of nucleolar function, including NCL-1, a homolog of BRAT/TRIM2, which inhibits production of FIB-1/fibrillarin, a nucleolar protein involved in the regulation and maturation of rRNA. The examples demonstrate that small nucleoli are a visible cellular hallmark of lifespan and metabolic health, and that molecules associated with nucleolar function might serve as predictive, causal biomarkers of life expectancy. Smaller nucleoli are also seen with interventions that improve metabolic health in humans, thus revealing a reversible process linking metabolic state to a simple cellular readout.

Consequently, the present invention refers particularly to the size of nucleoli as biomarker for ageing or lifespan. In addition, the nucleolar protein fibrillarin, TRIM2/3 and ribosome biogenesis are suitable biomarker for lifespan.

A first aspect of the invention is the use of the size of nucleoli as a biomarker for aging and metabolic health. The present invention refers to an in vitro use of nucleolar size as a biomarker for aging and metabolic health in animals, including humans.

The nucleolus is the most prominent substructure within the nucleus of eukaryotic cells which is the site of rRNA transcription and processing, and of ribosome assembly. Nucleoli also have other important functions like assembly of signal recognition particle and playing a role in the cell's response to stress. Nucleoli are made of DNA, RNA, and proteins. The nucleolus, which is not surrounded by a membrane, is organized around the chromosomal regions that contain the genes for the 5.8 S, 18 S, and 28 S rRNAs. Therefore, nucleoli can be found and analyzed in each sample containing cells. Preferably, the present invention refers to an in vitro use of nucleolar size as a biomarker for aging and metabolic health in animals, wherein nucleoli are derived from blood cells, adipose tissue or muscle biopsies. Blood is most preferred because it can be collected most easily.

Nucleoli have a substantially different refractive index from the rest of the nucleus and thus are clearly seen by methods such as phase-contrast or differential-interference contrast microscopy. They also stain differently from the rest of the nucleolus by staining with a variety of nucleic acid stains. Consequently, the size of the nucleoli can be determined after staining of the nucleolus in samples containing cells. The condensed chromatin surrounding part of the nucleolus is visible using standard or preferential staining methods. For example, DAPI excludes the nucleolus. The SYTO® RNASelect™ stain (ThermoFisher scientific) can be used to detect the nucleoli, and cells may be counterstained with a nuclear stain such as DAPI.

Eukaryotic cells often contain a single nucleolus, but several are also possible. The exact number of nucleoli is fixed among members of the same species. Each diploid cell in the human body features only one nucleolus, though immediately after cell division ten tiny nucleoli appear before they coalesce into a single, large nucleolus. Therefore, it is preferred that the methods of the invention comprise analysis of cells in a human sample having only one single nucleolus. Alternatively, it is possible to add the size of all nucleoli per cell.

Another aspect of the present invention is the use of the nucleolar size as biomarker for immune function. Thereby, a reduced amount of fibrillarin and therefore, nucleolar size correlates with an improved immune function. An improved immune function thereby refers to an improved reaction of the immune system to infections with pathogens. Thus, an animal having improved immune function is able to react faster and with better effectiveness to the infection with pathogens.

The term a biomarker, or biological marker, as used herein generally refers to a measurable indicator of some biological state or condition. Aging as used herein doesn't refer to the real age, but to the condition of the human or animal tested, and therefore, the aging biomarker refers to a virtual age. The methods of the invention comprise calculation of the life expectancy. Another aspect of the present invention is the use of the nucleolar size as biomarker for virtual age or life expectancy.

Still another aspect of the present invention is the use or determination of the nucleolar size to test the effect of chemical compounds, medication, food and/or diet on life expectancy or virtual age of animals, including humans. The virtual age or life expectancy of an animal (including humans) after a treatment with chemical compounds, medication, food and/or diet is determined by comparing the size of nucleoli of the treated animal with a non-treated control group. Chemical compounds to be tested may be, as a non-limiting example, compounds that may be released in the environment, either deliberately, such as insecticides, fungicides or herbicides, or indirectly, such as solvents used in paintings. As nucleolar size differs from species to species, representative age related sizes are defined for the animal species tested. It is self-evident, that it is not enough to determine only size of one nucleolus of a sample but to analyze several nucleoli and determine the nucleolar size of the sample using common statistical methods. Thus, the nucleolar size as used herein refers to an average size or median size of nucleoli. The invention refers to an in vitro use of nucleolar size as a biomarker for aging and metabolic health, wherein the age, life expectancy or virtual life is higher the smaller the nucleolar size is.

Altogether the examples of this application reveal that multiple lifespan pathways strikingly reduce nucleolar size, and diminish expression of the nucleolar protein FIB-1, ribosomal RNA, and ribosomal proteins across different species.

Conversely fibroblasts derived from Hutchinson-Gilford progeria syndrome patients show enlarged nucleolar size and elevated ribosome biogenesis and protein synthesis. These markers are not simply molecular correlates, however, but likely responsible in part for prolonged life. Notably, *C. elegans* FIB-1 is regulated by multiple molecular pathways, and its down-regulation is sufficient to extend lifespan. Evidently NCL-1 plays a critical role in regulating nucleolar size and inhibiting FIB-1 expression in part via its 3' UTR, thereby affecting lifespan in multiple pathways. In the NCL gene encodes the protein nucleolin. Interestingly in an independent systems biology study, transcriptome analysis of multiple lifespan pathways revealed down-regulation of fib-1 as a common target. The studies in this invention are the first to reveal that nucleolar functions work pervasively across many lifespan pathways. Reduced ribosome biogenesis and protein synthesis are the most obvious candidates for proximal mechanisms responsible for extended life. These energetically costly processes consume considerable resources, and a modest reduction of ribosomal proteins or translational regulators in model organisms prolongs life. Notably, transcriptomic analyses typically exclude ribosomal RNA, thus overlooking the very molecules that according to the present findings affect lifespan.

The present invention discloses a novel role of the nucleolus and more specifically the nucleolar methytransferase Fibrillarin in response to infection against different pathogenic bacteria. Infection in *C. elegans* with *Staphylococcus aureus* and *Enterococcus faecalis* leads to a reduction in nucleolar size. ncl-1/TRIM2 mutants that are known to possess enlarged nucleoli are refractory to infection mediated reduction in nucleolar size and are thereby more sensitive to infection suggesting that a reduction in nucleolar size might be a protective innate immune response towards infection.

Therefore, another embodiment of the invention relates to the use of nucleolar size as aging biomarker, wherein at least one further biomarker for aging is determined. Thereby it is preferred that the at least one further biomarker for aging is selected from the group comprising Fibrillarin, TRIM2/3 or NCL-1 and ribosome biogenesis. NCL-1 is the *C. elegans* homolog of TRIM2/3. More preferably, the at least one further biomarker for aging is Fibrillarin. Therefore, it depends of the species which biomarker is determined. In case the sample is derived from *C-elegans* NCL-1, whereas in humans TRIM2 and/or TRIM3 can be determined.

The creation of ribosomes is a process known as ribosome biogenesis. It involves the coordinated function of over 200 proteins in the synthesis and processing of the three prokaryotic or four eukaryotic rRNAs, as well as assembly of those rRNAs with the ribosomal proteins. Most of the ribosomal proteins fall into various energy-consuming enzyme families including ATP-dependent RNA helicases, AAA-ATPases, GTPases, and kinases. Ribosome biogenesis is a very tightly regulated process, and it is closely linked to other cellular activities like growth and division. Within the present invention ribosome biogenesis refers preferably to the amount of rRNA and/or ribosomal proteins. Therefore, another embodiment of the invention relates to the use of nucleolar size as aging biomarker, wherein at least the expression levels of rRNA or ribosomal proteins is determined.

A down-regulation of ribosome biogenesis is associated with longevity. Thus, life expectancy is higher the lower the expression levels of rRNA or ribosomal proteins is. NCL-1 regulates fibrillarin. The nucleolar marker fibbrillarin is down regulated in long lived worms and flies. Thus, NCL-1 overexpression or fibrillarin (FIB-1) downregulation extends life. Expression levels of fibrillarin are a suitable biomarker for ageing or life expectancy. Within the methods of the present invention, life expectancy is higher the lower the expression levels of fibrillarin are.

Animals including humans age at different rates. The chronological age (calendar age) is the number of years a person has been alive. The term virtual age (biological age) or physiological age as used herein, is a measure of how well or poor a body of an animal including a human is functioning relative to its chronological age. The virtual age (biological age) represents one's present position in regard to the probability of survival. The virtual age (biological age) is defined as a description of an individual's calculated actual age based on the inventive biomarkers. The virtual age is a reflection of the health and vitality of the sample, i.e. an animal, including humans. In the present invention, it is determined on the basis of the analyzed, i.e. measured size of the nucleoli thereof. The virtual age as determined is used to calculate the life expectancy of the sample, i.e. an animal, including human from their chronological age.

Another embodiment of the present invention refers to an in vitro method for determining the life expectancy or virtual age of an animal, including human, comprising:
 a) providing a sample containing nucleoli,
 b) analyzing the size of the nucleoli, and
 c) determining the virtual age according to the size of the nucleoli.

In the step c) the term "virtual age" can also be replaced by the term "life expectancy" as follows:
 an in vitro method for determining the life expectancy or virtual age of an animal, including human, comprising:
 a) providing a sample containing nucleoli,
 b) analyzing the size of the nucleoli, and
 c) determining the life expectancy according to the size of the nucleoli.

Each sample containing cells is thereby suitable because nucleoli are compartments of a cell nucleus. The sample of step a) is preferably blood, particularly blood cells, adipose tissue or muscle biopsies. Blood is most preferred because it can be collected most easily.

Step b) comprises preferably staining of the nucleolus and subsequently measurement of the diameter or area of the nucleolus, or respectively a statistically significant number of nucleoli of the sample. Methods for staining of the nucleolus are commonly known in the art (see above). It is self-evident that step c) comprises comparison of nucleolar size determined during step b) with a standard size or a standard curve representing the correlation of nucleolar size and life expectancy for a representative, healthy individual of the revealed species. Thereby, life expectancy or virtual age is higher the smaller the nucleolar size is.

In a preferred embodiment of the invention the ex-vivo method for determining the life expectancy or virtual age of animals comprises further step b)' analyzing the expression level of fibrillarin, TRIM2/3 (NCL-1) and/or ribosome biogenesis and wherein step c) reads: c) determining the virtual age, or the life expectancy according to the size of the nucleoli, as well as the expression level of fibrillarin, TRIM2/3 (NCL-1) and/or ribosome biogenesis. It is preferred that ribosome biogenesis is analyzed by determining ribosomal protein and rRNA levels, wherein virtual age, or the life expectancy is higher the lower the ribosomal protein or rRNA levels are.

Thus preferred is an in vitro (ex-vivo) method for determining the life expectancy or virtual age of an animal, including human, comprising:
 a) providing a sample containing nucleoli,
 b) analyzing the size of the nucleoli,
 b)' analyzing the expression level of fibrillarin, TRIM2/3 (NCL-1) and/or ribosome biogenesis and
 c) determining the virtual age, or the life expectancy according to the size of the nucleoli as well as the expression level of fibrillarin, TRIM2/3 (NCL-1) and/or ribosome biogenesis.

More preferably, at least one further biomarker is the expression level of fibrillarin and thus the preferred in vitro (ex-vivo) method for determining the life expectancy or virtual age of an animal, including human, comprises:
 a) providing a sample containing nucleoli,
 b) analyzing the size of the nucleoli,
 b)' analyzing the expression level of fibrillarin, and
 c) determining the virtual age, or the life expectancy according to the size of the nucleoli and the expression level of fibrillarin.

Methods for determination of an expression levels are well known in the art and comprises quantifying the level at which a gene is expressed within a sample. Ideally, measurement of expression is done by detecting the final gene product (for many genes, this is the protein); however, it is often easier to detect one of the precursors, typically mRNA and to infer gene-expression levels from these measurements. General methods are therefore western blotting, northern blotting and RT-qPCR.

(a) eat-2(ad465) animals have smaller nucleoli while ncl-1(e1942) and eat-2; ncl-1 animals possess larger nucleoli compared to N2. (b) Nucleolar size is reduced upon bacterial food reduction with a corresponding increase in lifespan. (P<0.0001, log-rank test). (c,d) eat-2(ad465), TOR RNAi, isp-1(qm150), glp-1(e2141) and daf-2(e1370) animals possess smaller nucleoli while daf-2; daf-16 have nucleoli similar to N2 in the hypodermis and pharyngeal muscle. (e,f) Schematic illustration of the experiment, which shows that longer-lived worms exhibit small nucleoli and vice versa. (The graph depicts mean and standard deviation. Pearson correlation coefficient $R^2$=0.93 is calculated using the entire data set). Scale bar represents 5 μm. *P<0.05, P<0.01, *P<0.001, ****P<0.0001, ns: nonsignificant, unpaired t-test.

Figure 3:
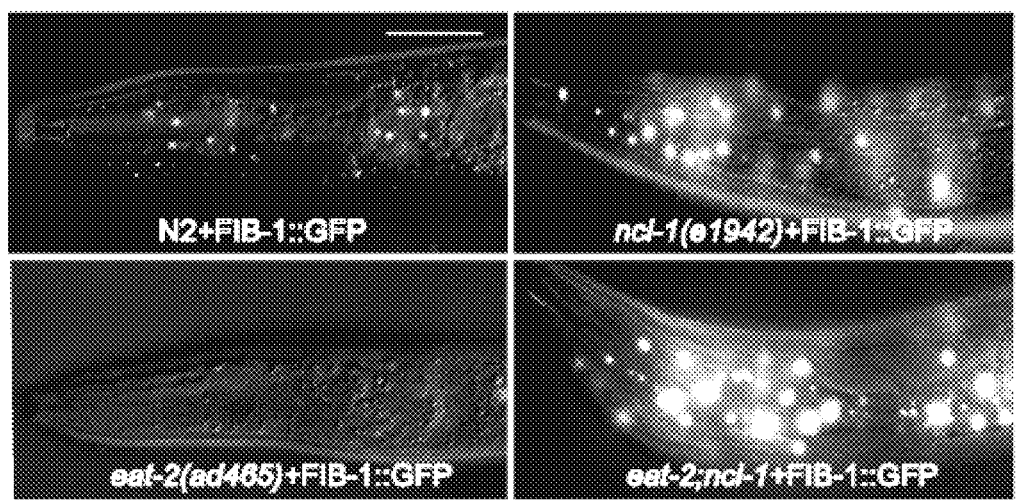
Figure 3:
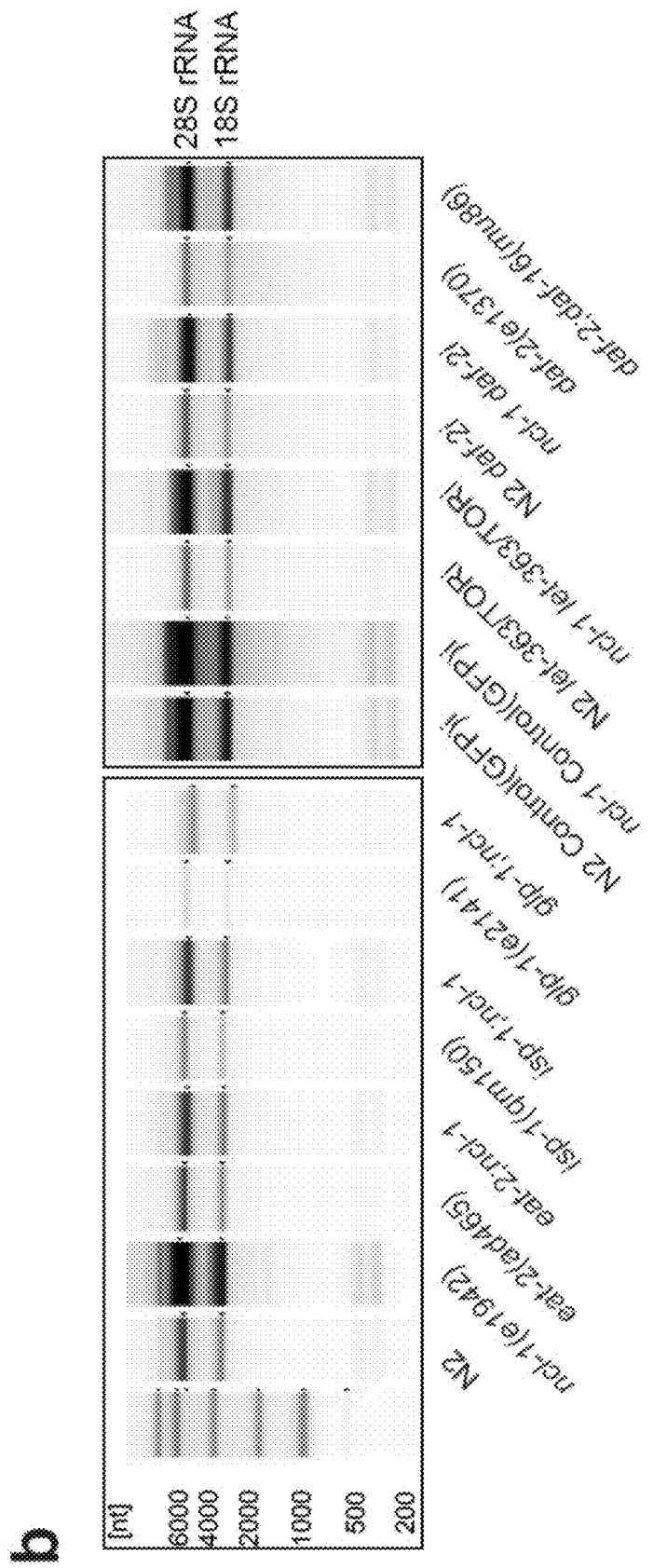
Figure 3:
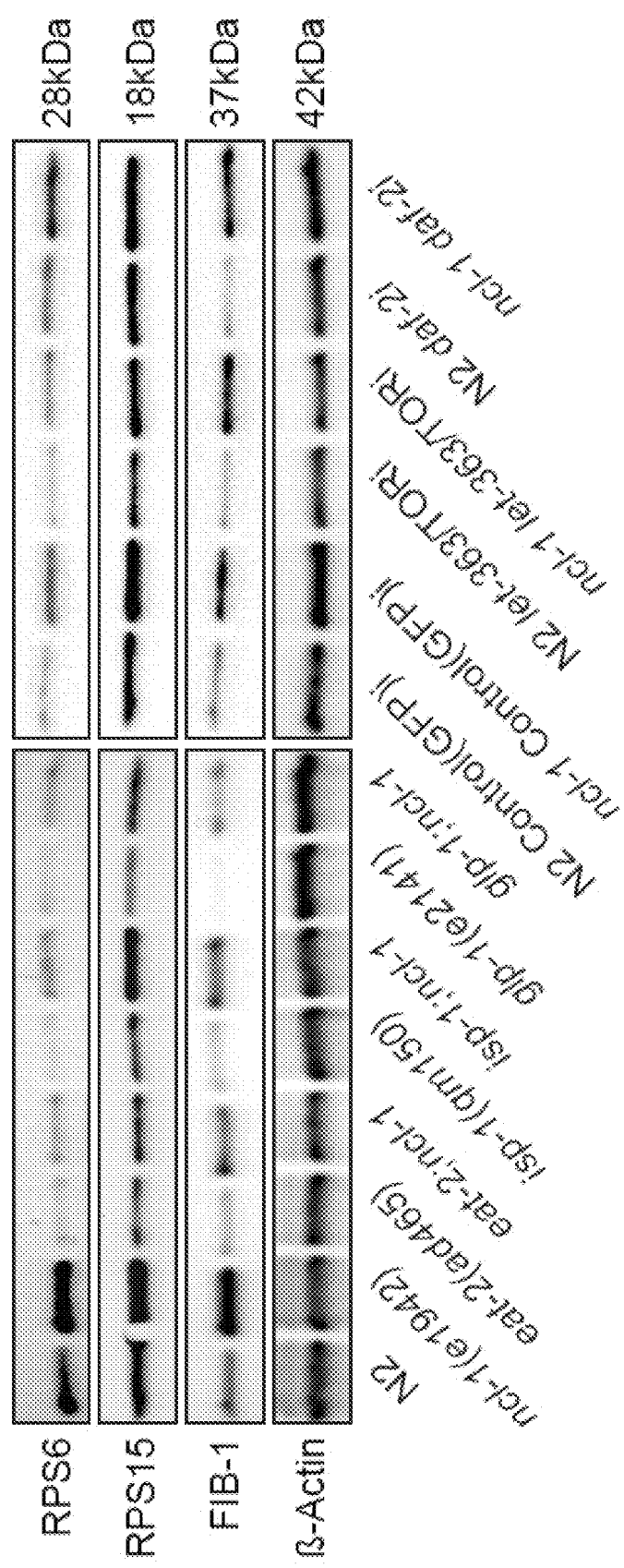
Figure 3:
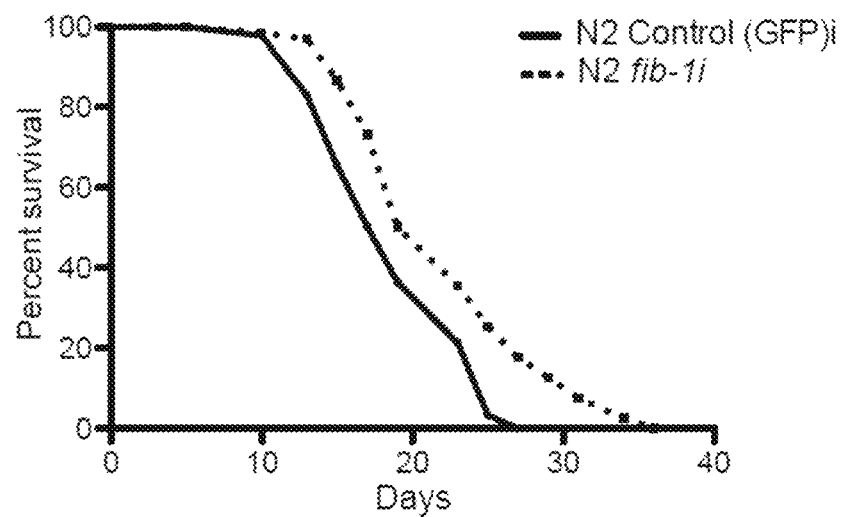
Figure 3:
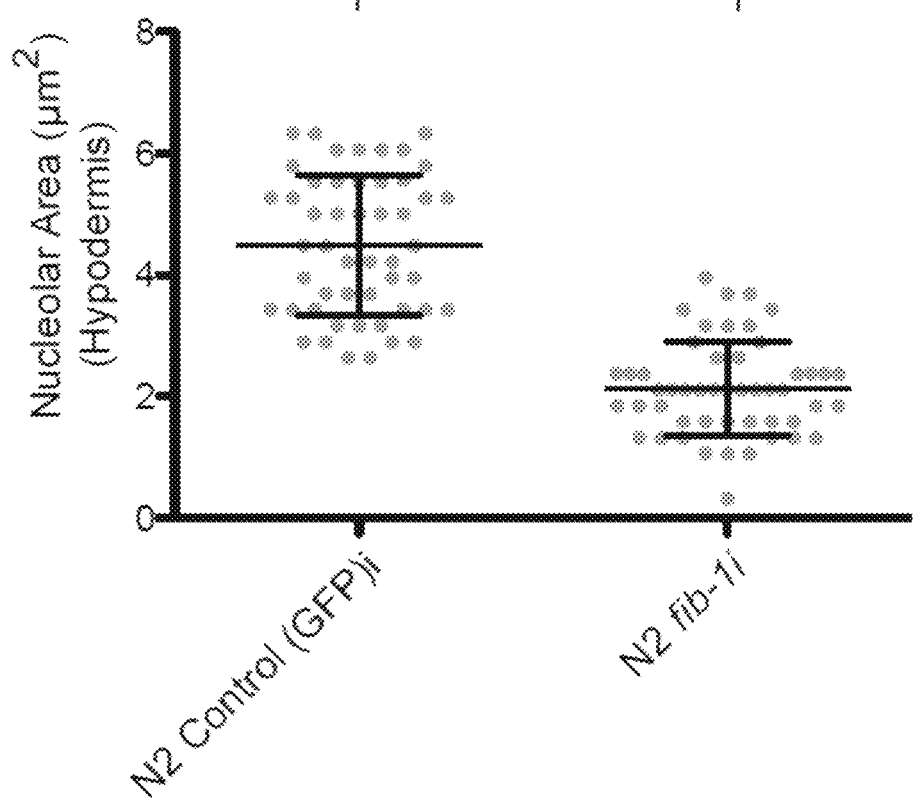

FIG. 3: shows that ncl-1 and lifespan mutants regulate fibrillarin, rRNA, and ribosomal protein levels. (a) FIB-1::GFP is strongly down-regulated in eat-2(ad465) animals but up-regulated in ncl-1 and eat-2;ncl-1 double mutants. (b,c,d) rRNA, RPS6, RPS15 and FIB-1 levels are increased in ncl-1(e1942) and reduced in eat-2(ad465), isp-1(qm150), glp-1(e2141), daf-2 RNAi and TOR RNAi and this effect is partially reversed by loss of ncl-1. daf-2(e1370) also shows reduced rRNA levels compared to daf-2;daf-16(mu86). (e) fib-1 RNAi extends lifespan of N2 (p=0.0004, logrank test) (f) fib-1 RNAi reduces the nucleolar size of N2. Scale bar represents 20 μm. *P<0.05, P<0.01, **P<0.0001, unpaired t-test.

Figure 4:
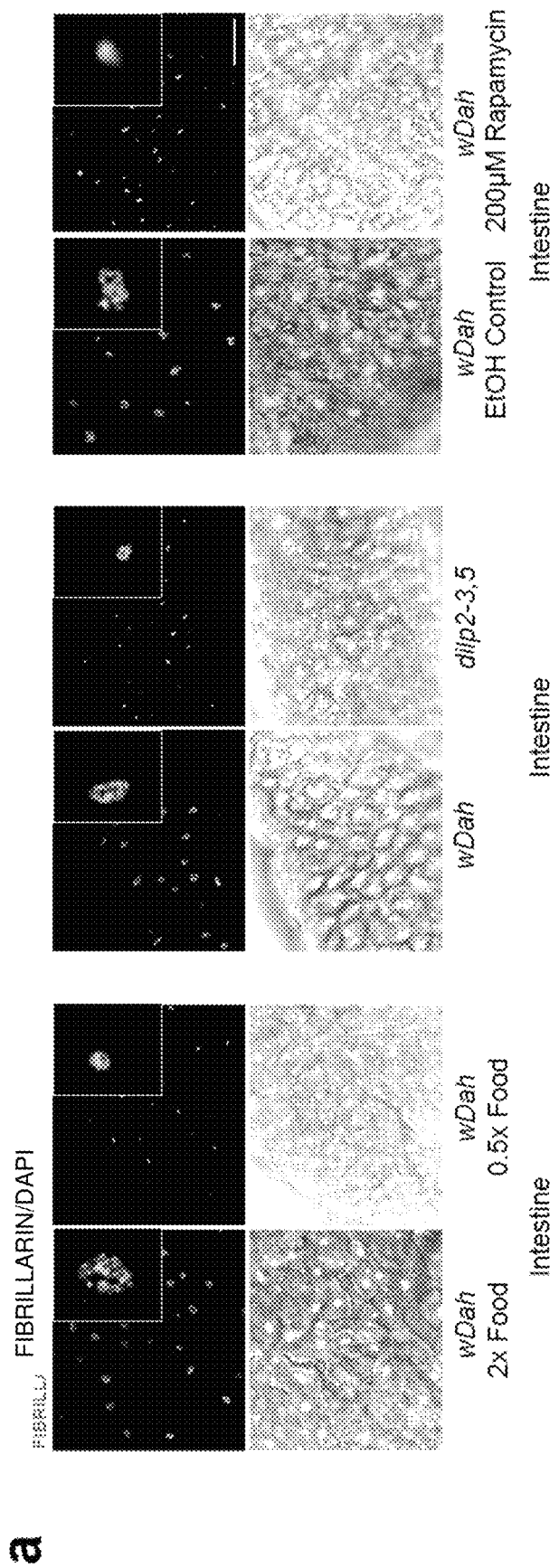
Figure 4:
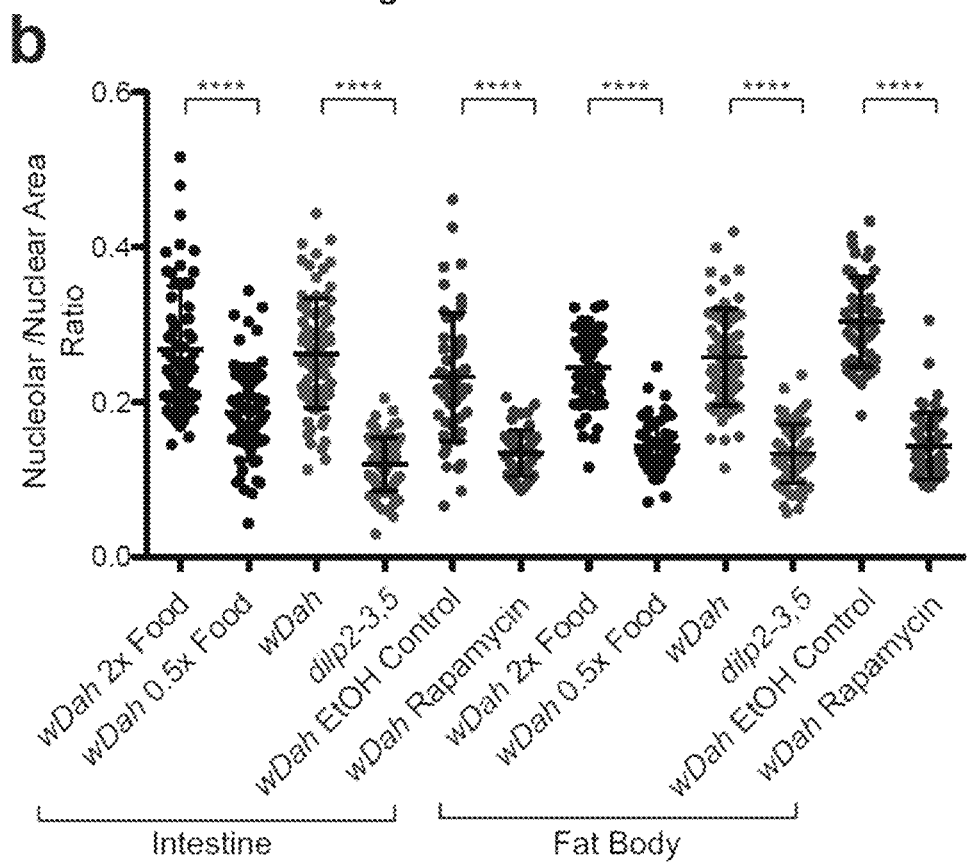
Figure 4:
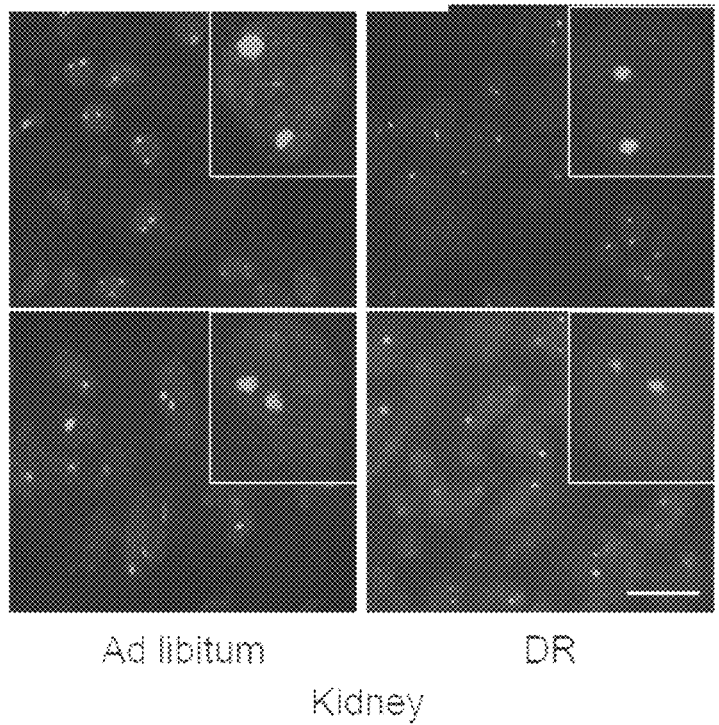
Figure 4:
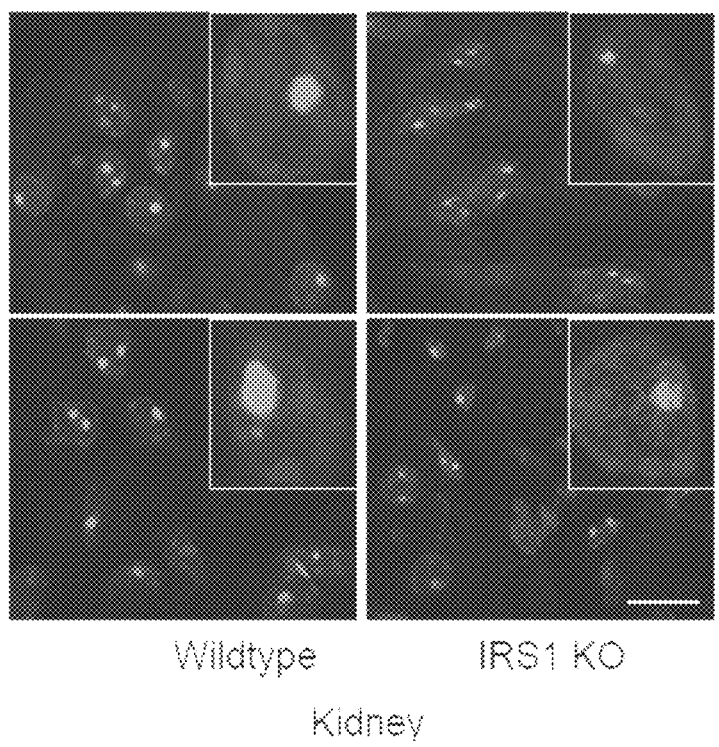
Figure 4:
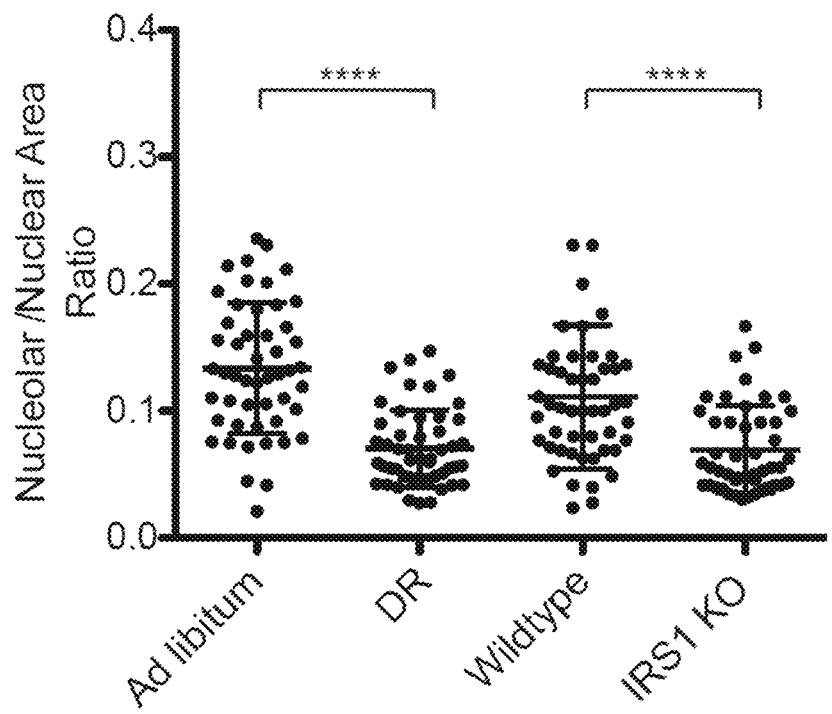
Figure 4:
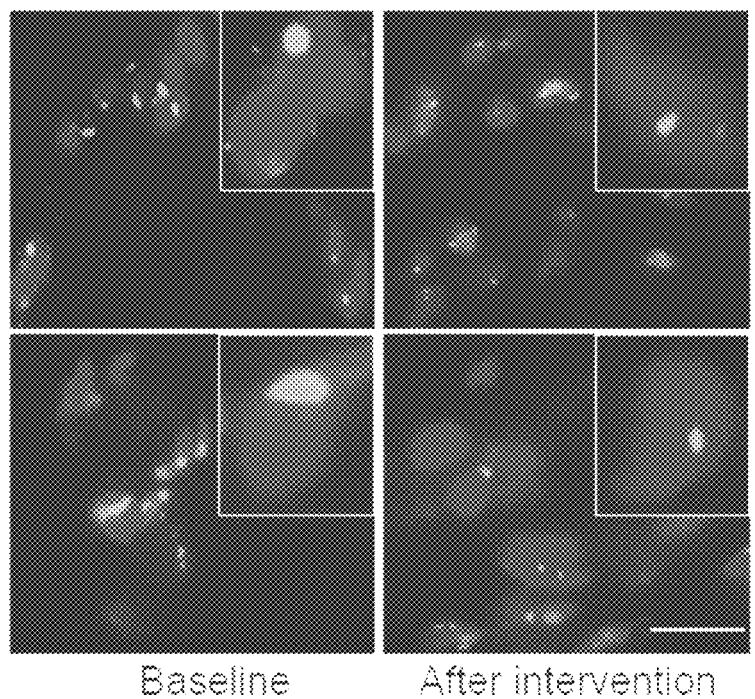
Figure 4:
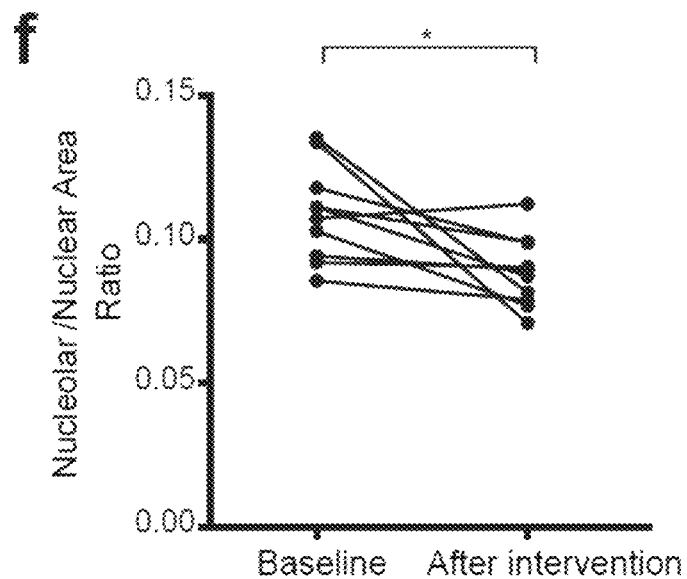

FIG. 4: shows that smaller nucleoli are also associated with lifespan in higher organisms. (a,b) DR, dilp2-3,5 and Rapamycin treated D. melanogaster possess small nucleoli in intestine and fat body. (c,d) DR and IRS1 knockout mice show reduced nucleolar size in kidney tissue compared to ad libitum fed mice and wildtype. (e,f) Muscle biopsies from humans undergoing DR and exercise exhibit small nucleoli. Scale bars represent 10 μm (a,c) and 20 μm (e). *P<0.05 paired t-test, ****P<0.0001 unpaired t-test.

Figure 5:
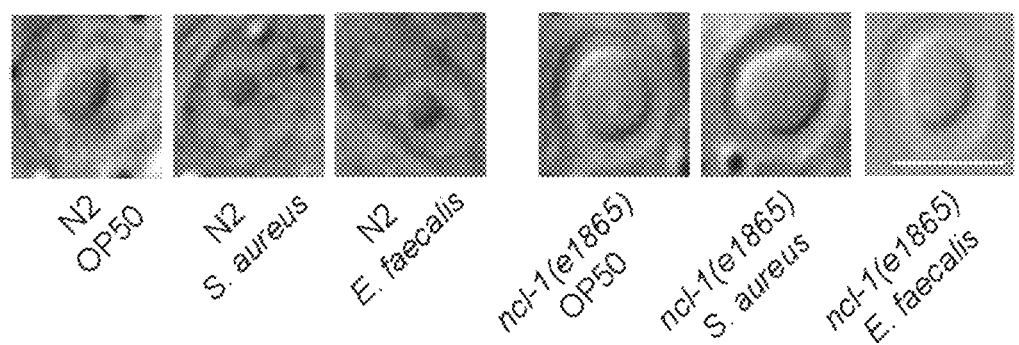
Figure 5:
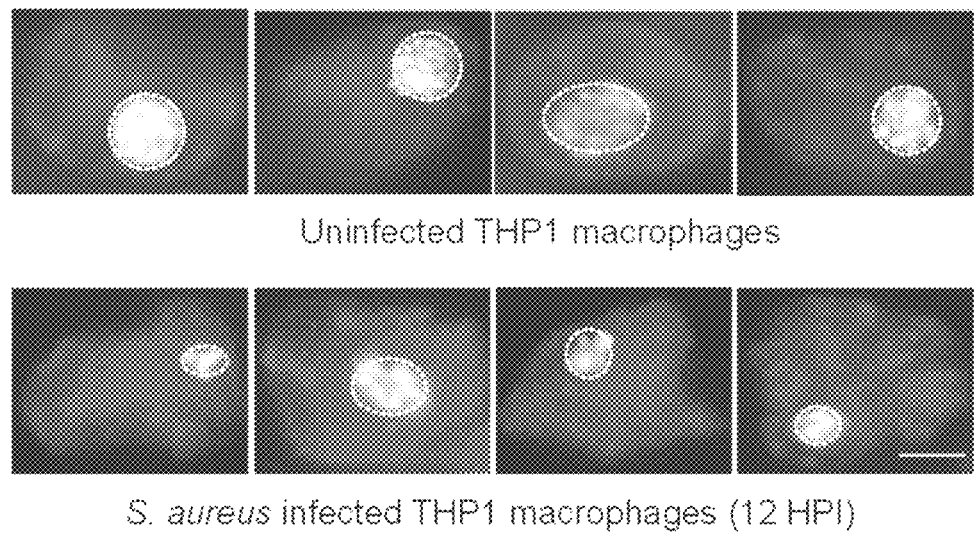

FIG. 5: (a) Wildtype N2 worms infected with the designated bacteria exhibit a reduction in hypodermal nucleolar size whereas there is no reduction in the nucleoli of ncl-1/RTRM2 mutants upon infection. (b) Human THP1 macrophases display a nuceloar size reduction 12 hours post-infection with S. aureus.

Figure 6:
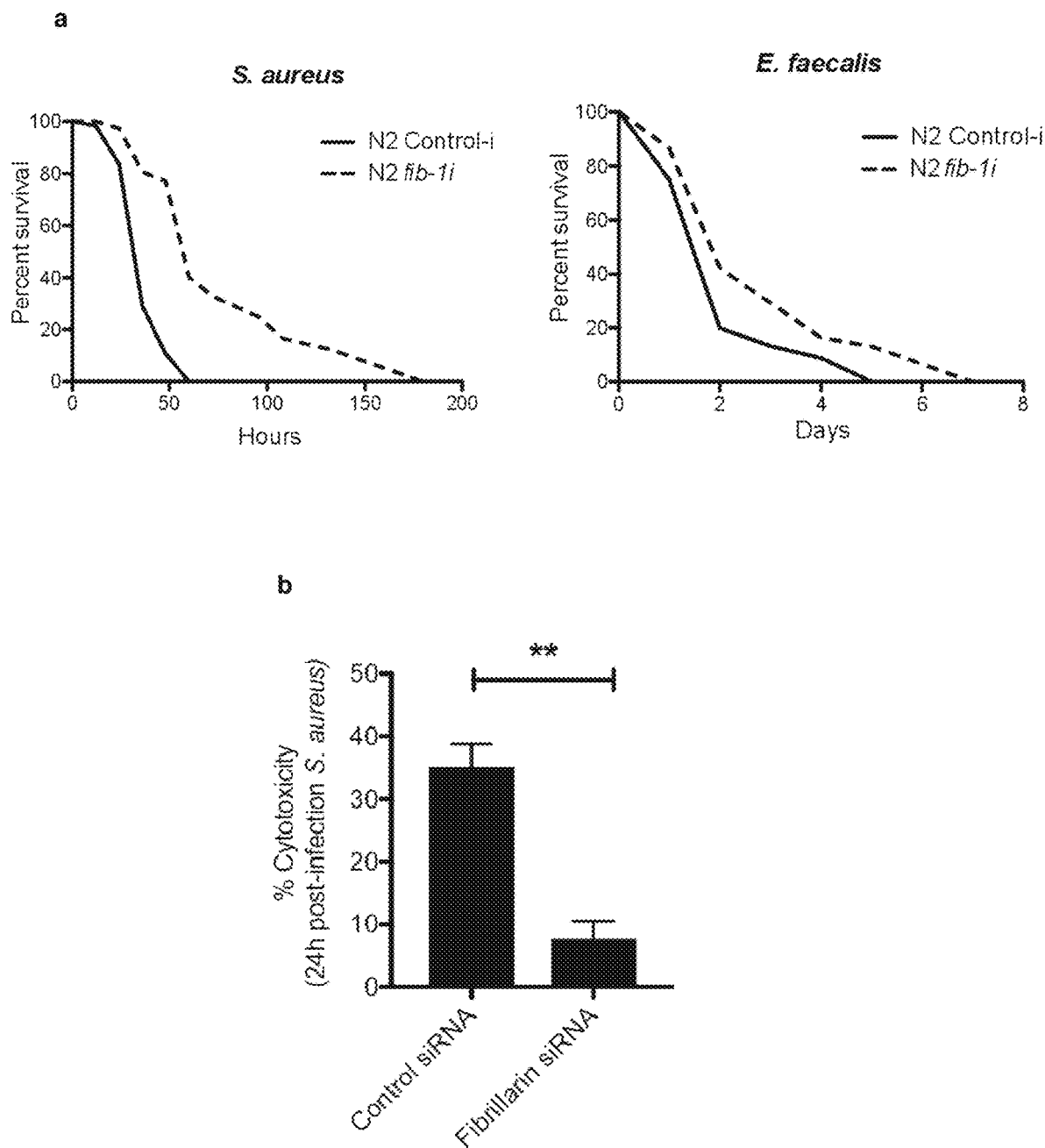

FIG. 6: (a) Fibrillarin (fib-1) knockdown prior to infection significantly improves survival of C. elegans upon infection with S. aureus and E. faecalis. (b) Fibrillarin reduction using siRNA significantly lowers cytotoxicity in murine bone marrow macrophages infected with S. aureus.

Figure 7:
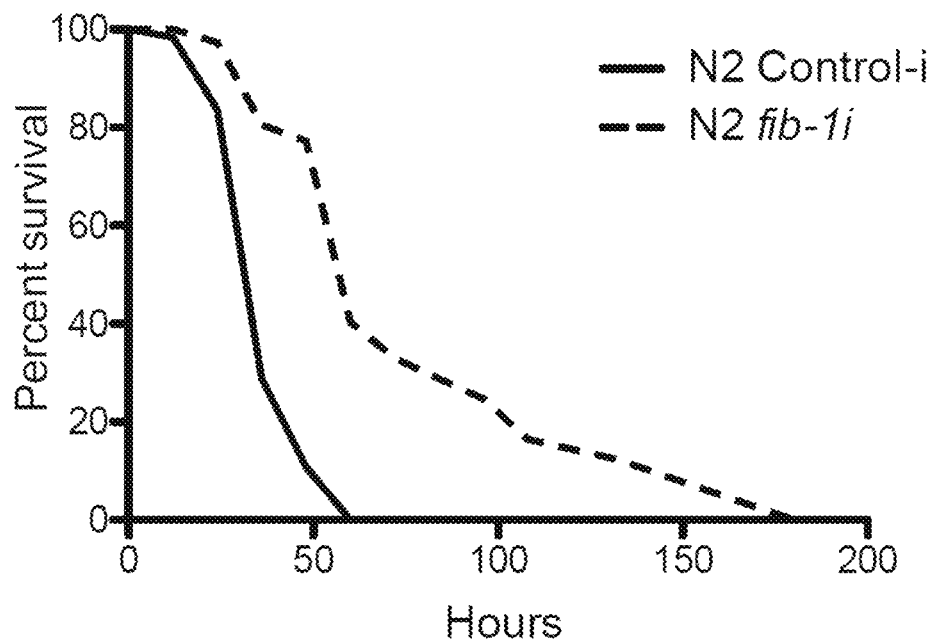
Figure 7:
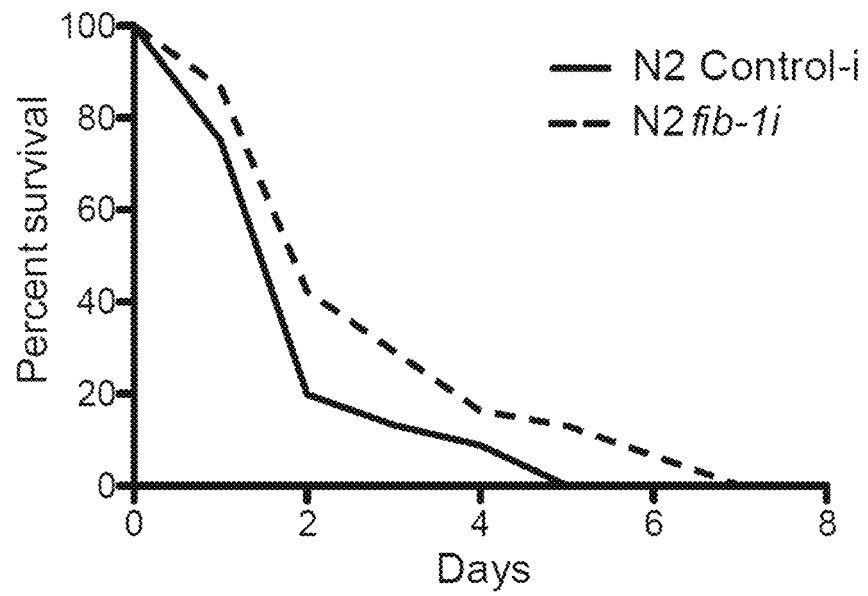
Figure 7:
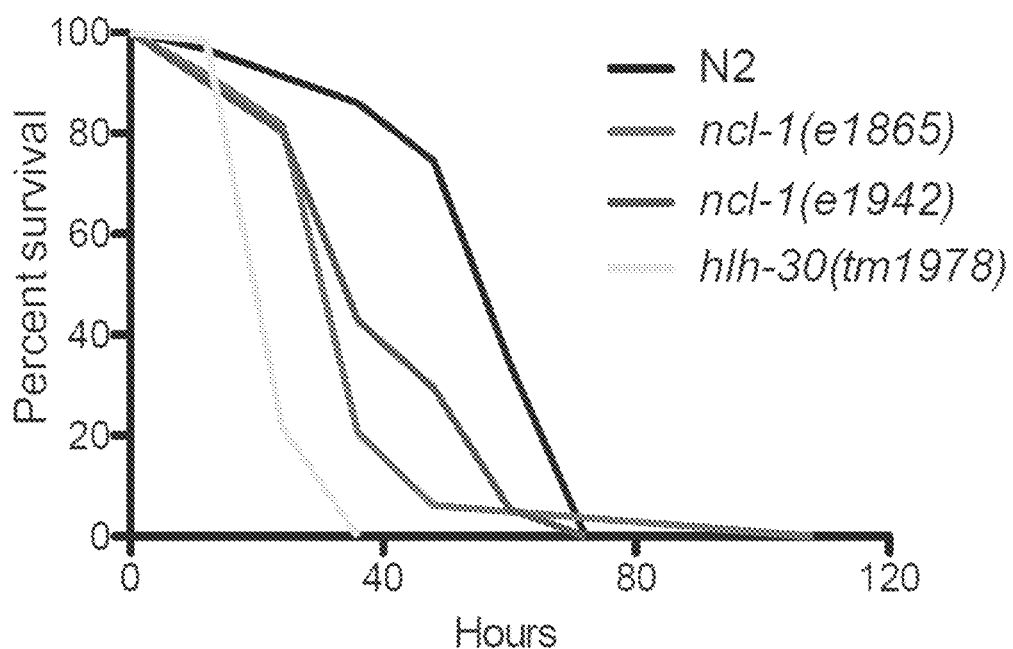
Figure 7:
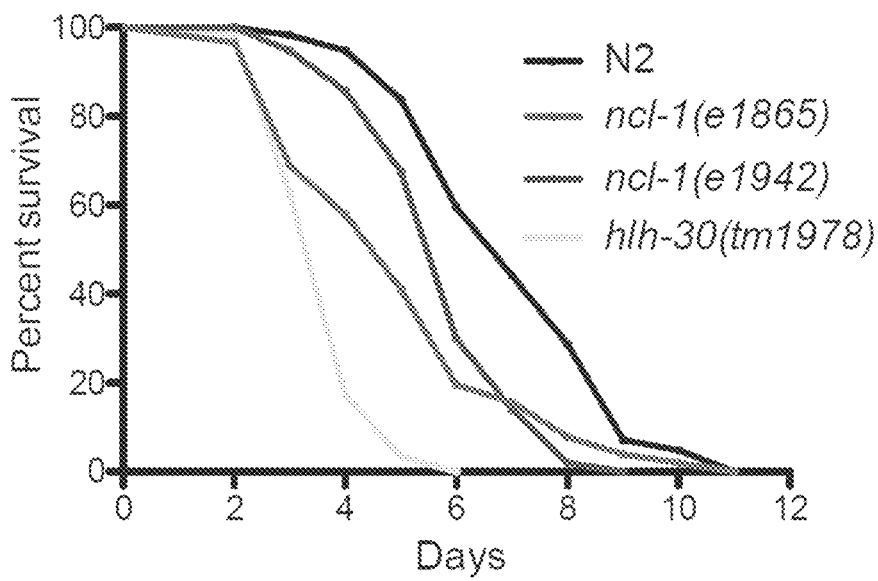

FIG. 7: shows that fib-1/Fibrillarin regulates bacterial infection resistance in C. elegans. (A,B) fib-1 knockdown improves survival of wildtype N2 worms upon S. aureus and E. faecalis infection (P<0.0001). (C,D) ncl-1 mutants (e1865 and e1942) are short-lived compared to wildtype N2 upon infection with S. aureus and E. faecalis (P<0.0001). hlh-30(tm1978) served as a control for infection. Survival experiments were performed three times independently. P-values were calculated by log-rank test.

Figure 8:
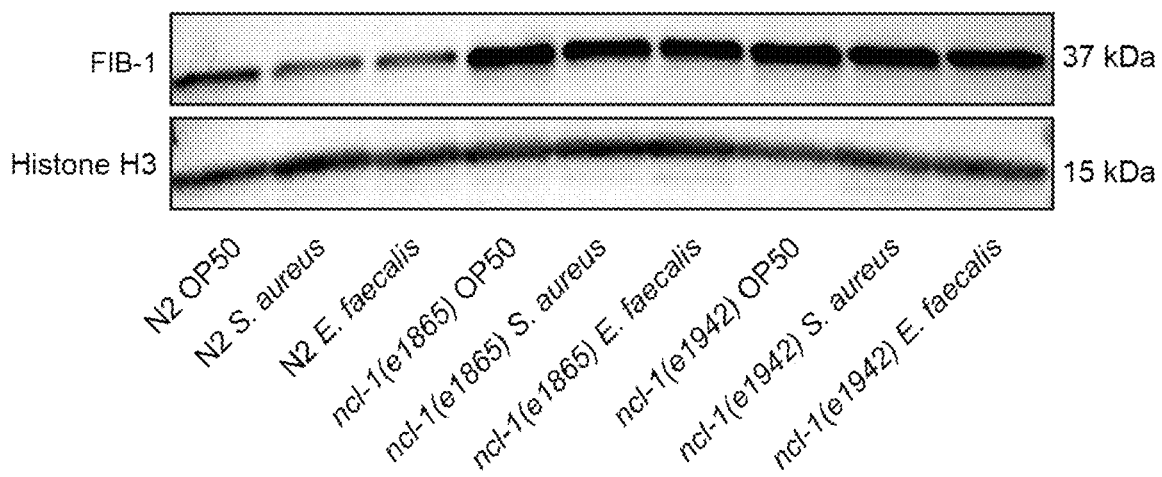
Figure 8:
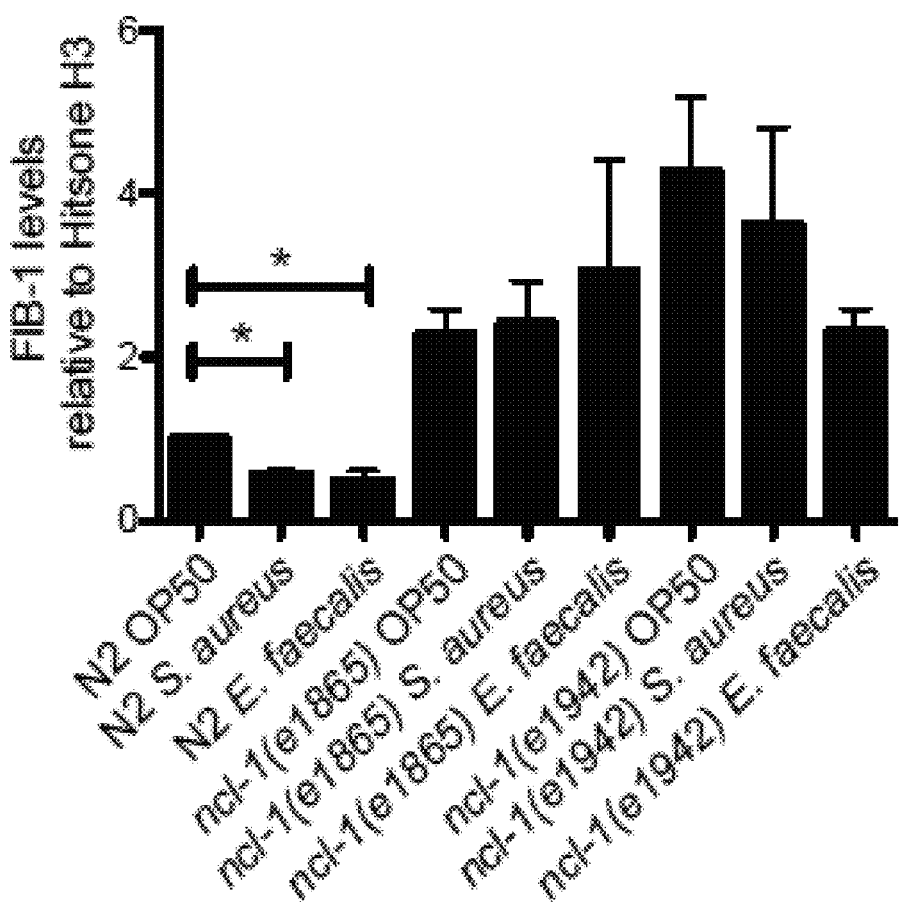
Figure 8:
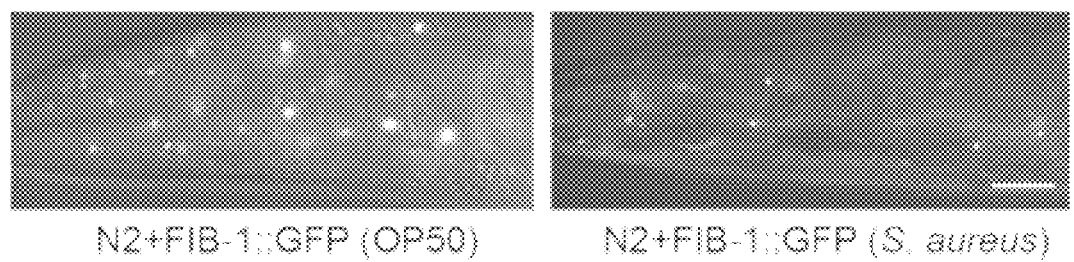
Figure 8:
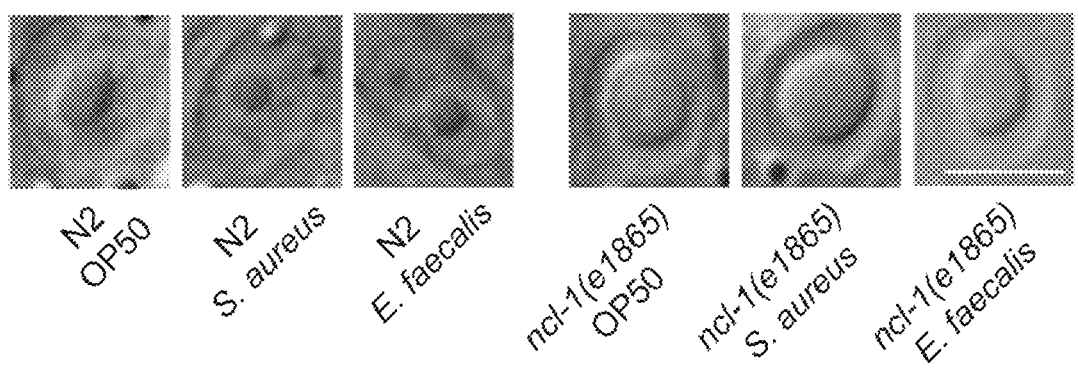
Figure 8:
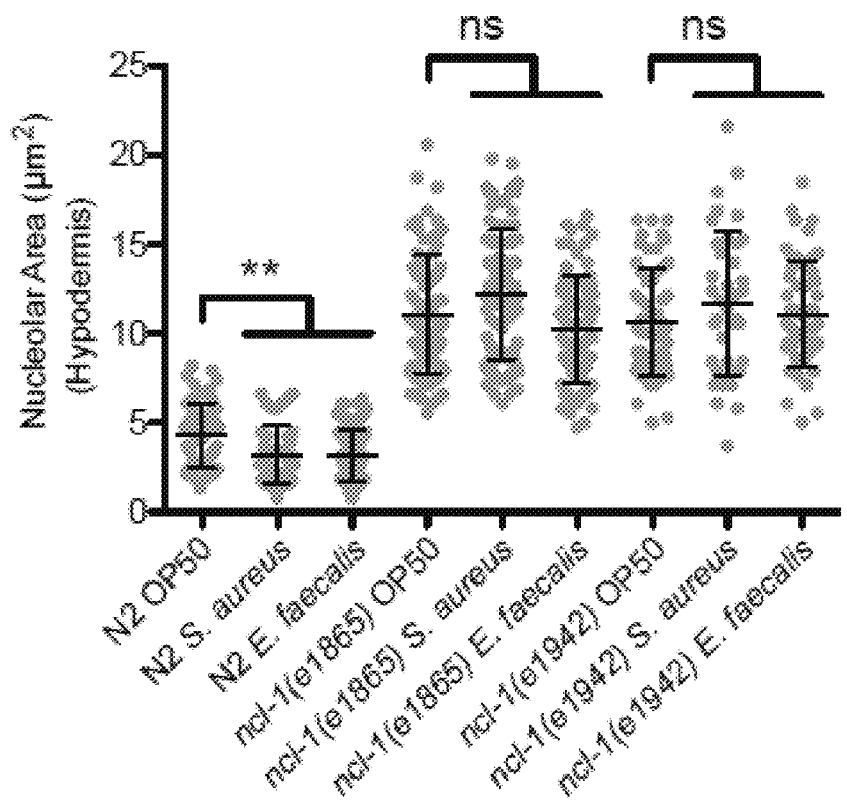

FIG. 8: shows that fib-1/Fibrillarin and nucleolar size are reduced upon bacterial infection. (A,B) FIB-1 levels are significantly reduced in wildtype N2 after S. aureus and E. faecalis infection. FIB-1 is reduced in ncl-1 mutants after infection but the levels are still higher relative to wildtype N2 after infection. Error bars represent mean±s.e.m. of three independent biological replicates. (C) FIB-1::GFP shows reduced fluorescent signal after infection with S. aureus. (D,E) Nucleolar size in hypodermal cells of wildtype N2 worms is reduced after 12-hour infection with S. aureus and E. faecalis. Nucleolar size in hypodermal cells of ncl-1 mutants after infection remains unaffected. Error bars represent mean ±s.d. Scale bars represent 20 μm (C) and 5 μm (D). *P<0.05, **P<0.01, ns non-significant, unpaired t-test.

Figure 9:
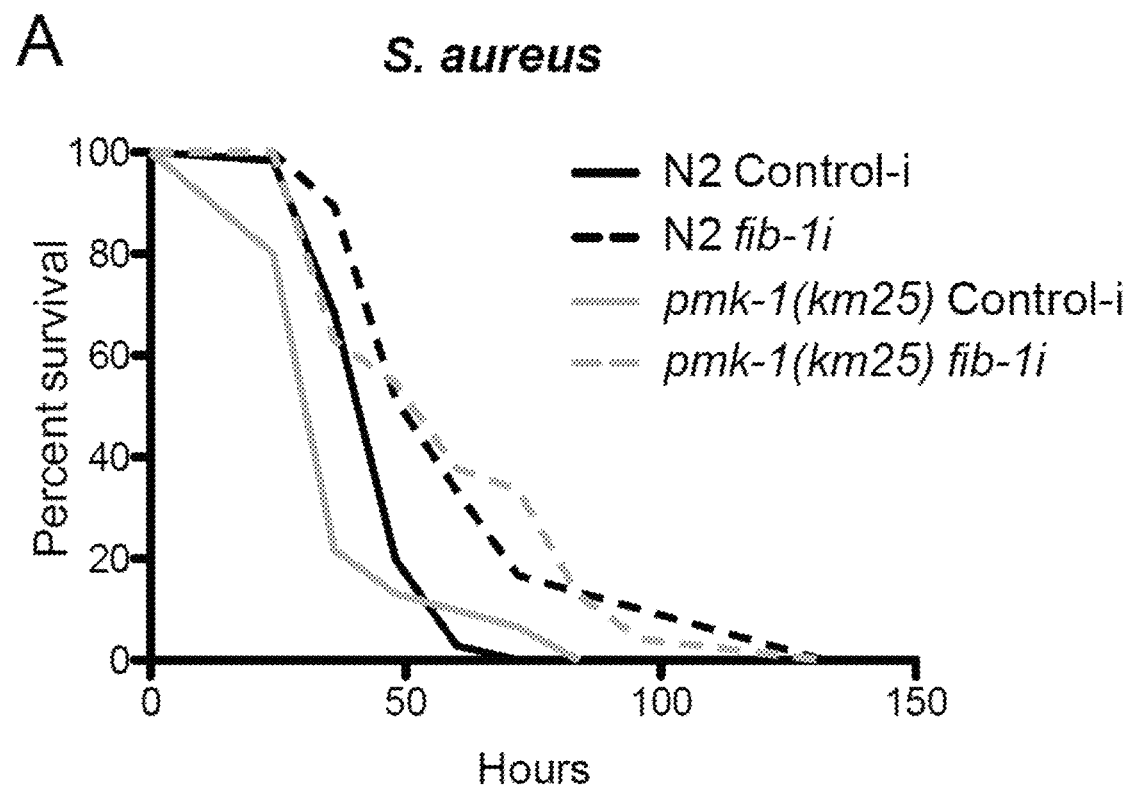
Figure 9:
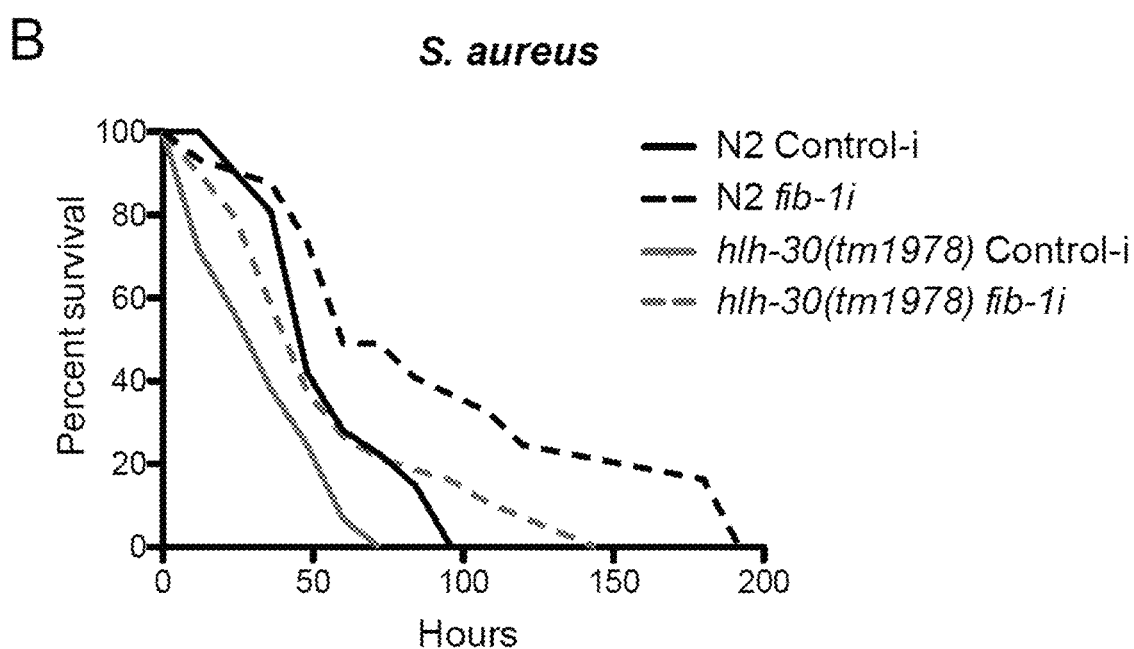
Figure 9:
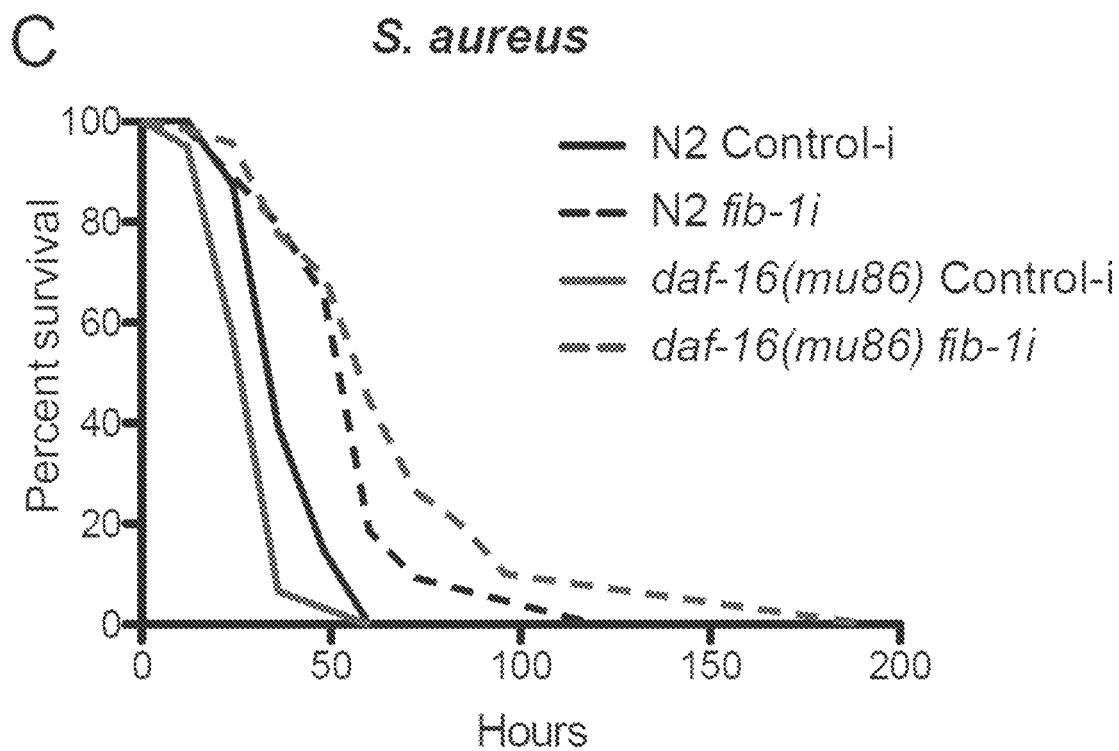
Figure 9:
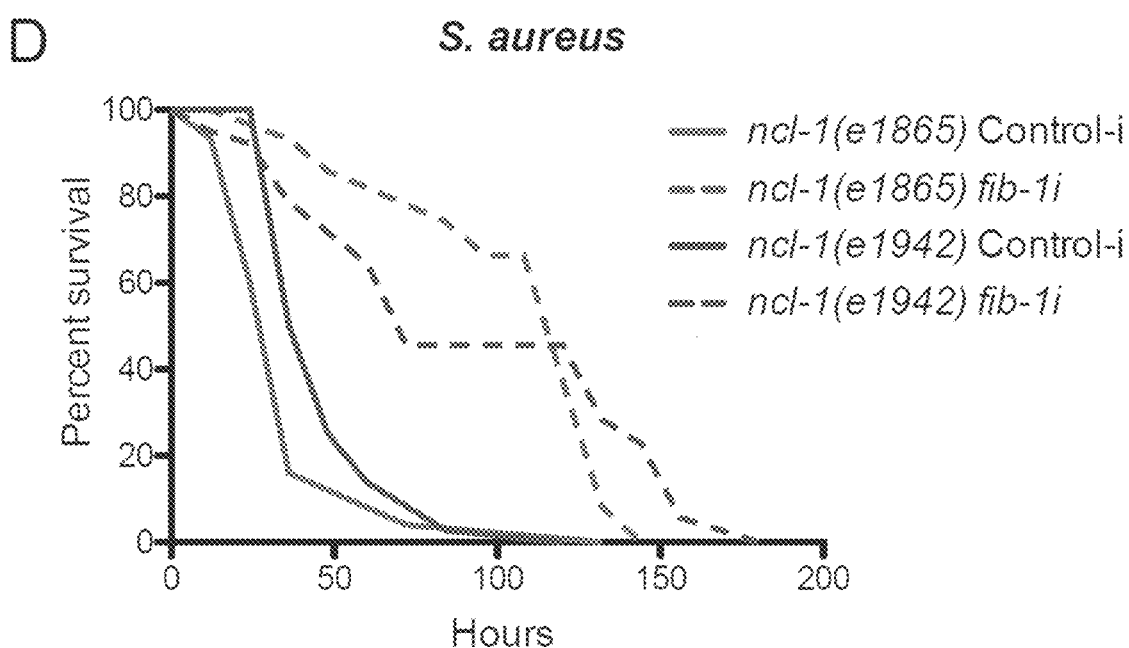

FIG. 9: shows that fib-1/Fibrillarin reduction improves resistance of infection sensitive mutants. (A,B,C,D) fib-1 RNAi significantly improves the survival of infection sensitive pmk-1(km25) (P=0.0001), hlh-30(tm1978) (P=0.0021), daf-16(mu86) (P<0.0001) and ncl-1(e1865 and e1942) mutants (P<0.0001) upon S. aureus infection. Survival experiments were performed three times independently. P-values were calculated by log-rank test.

Figure 10:
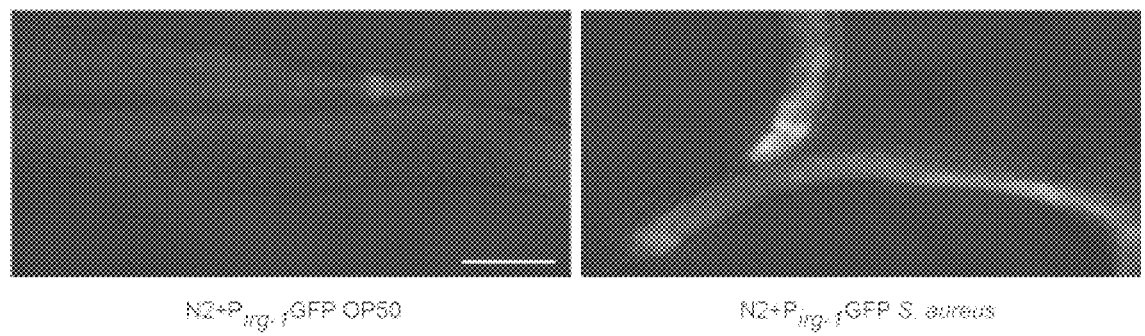
Figure 10:
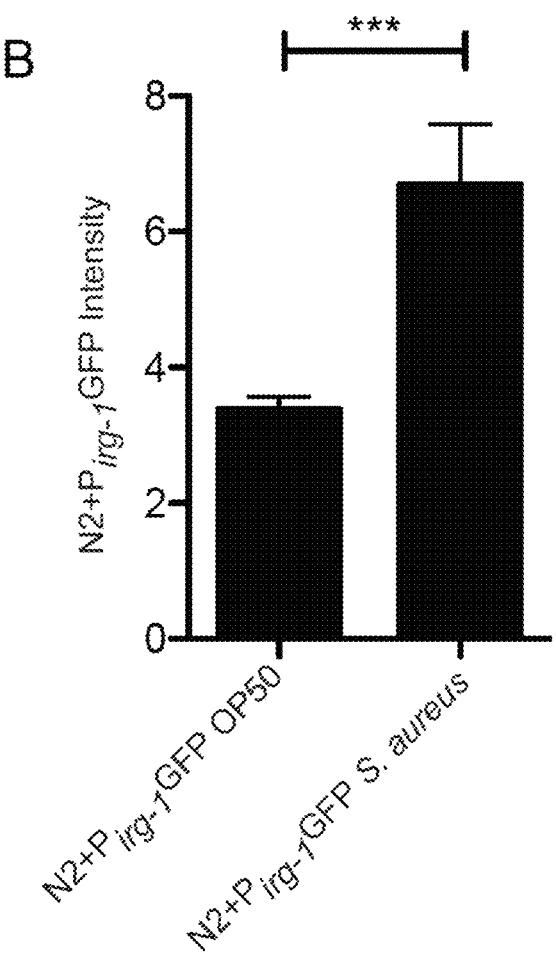
Figure 10:
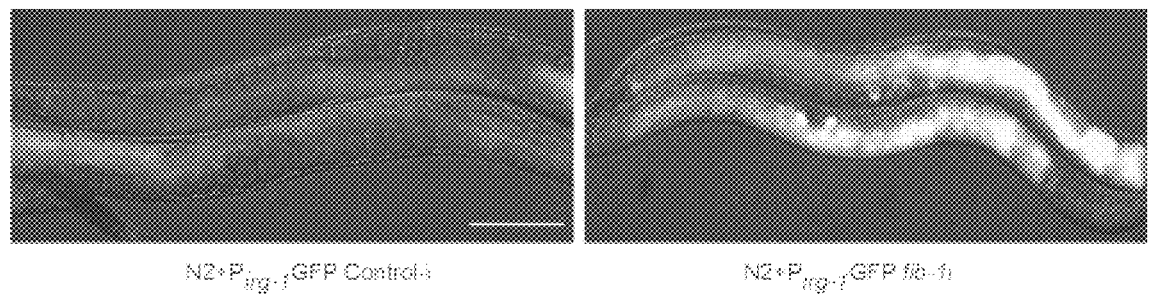
Figure 10:
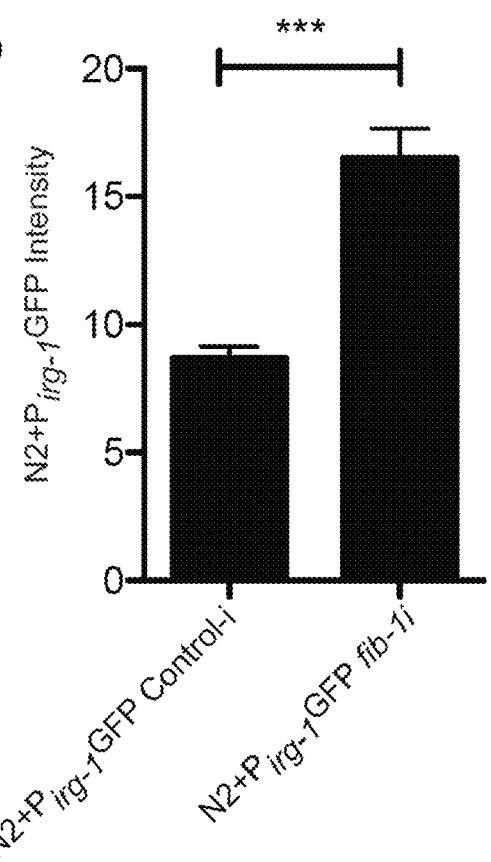
Figure 10:
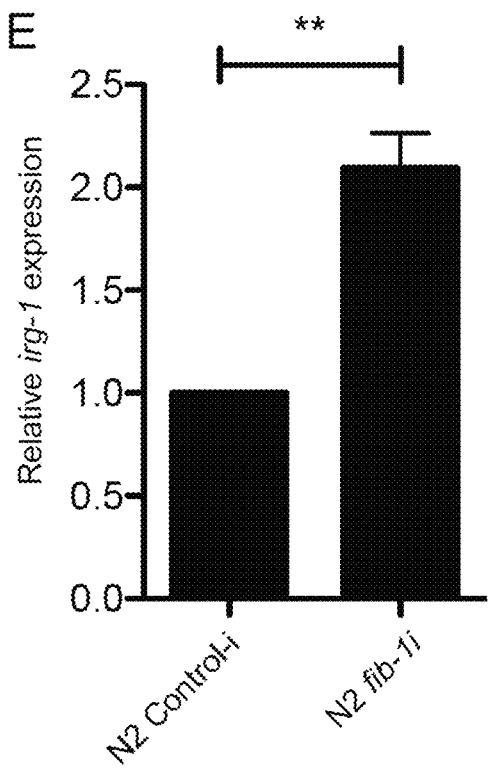
Figure 10:
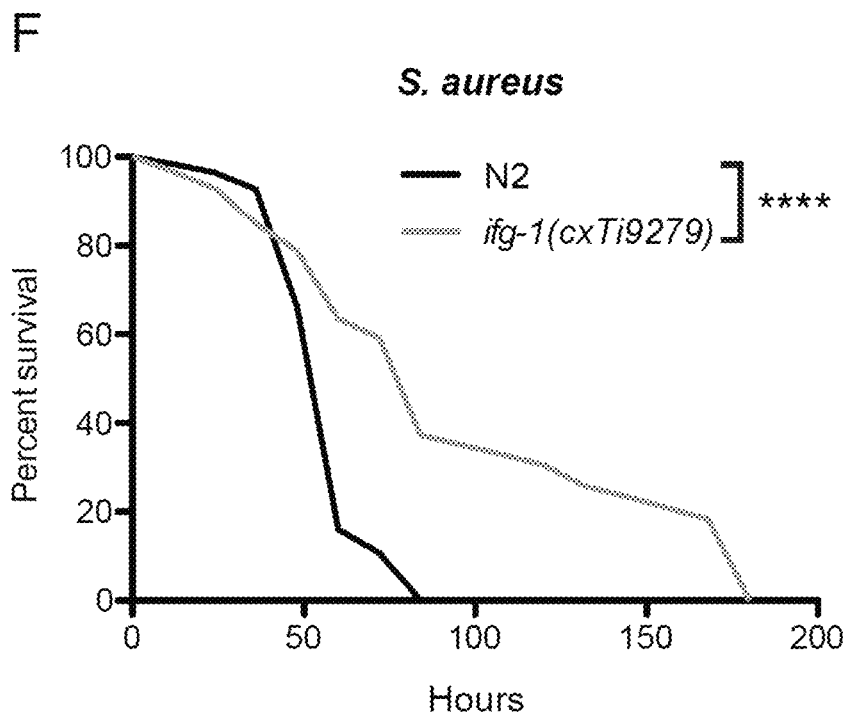
Figure 10:
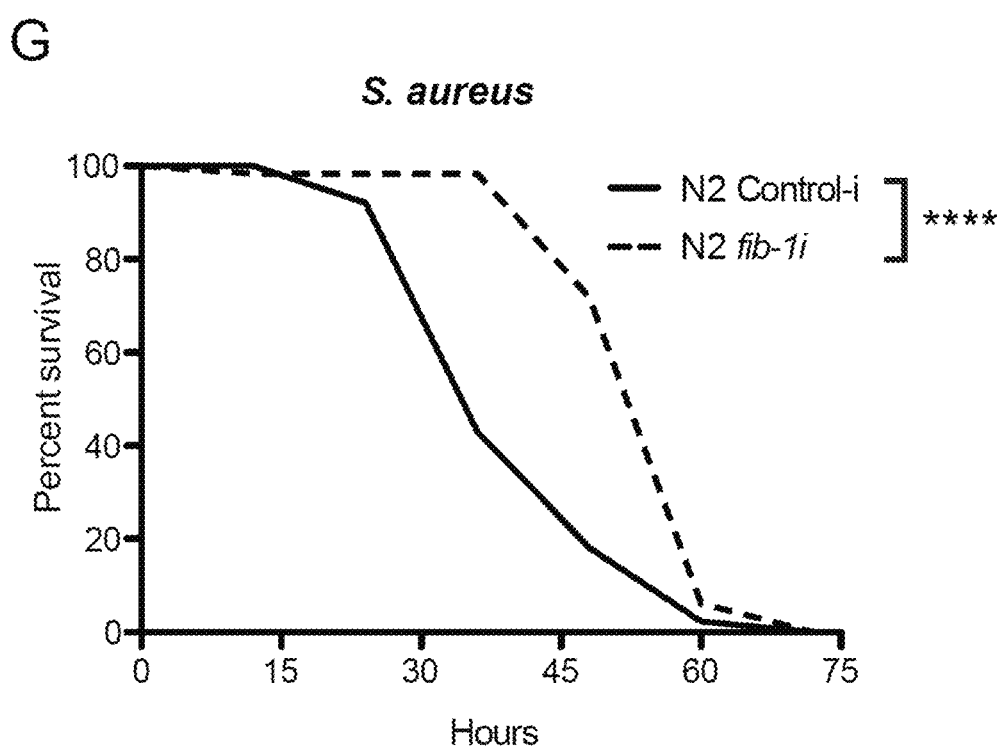
Figure 10:
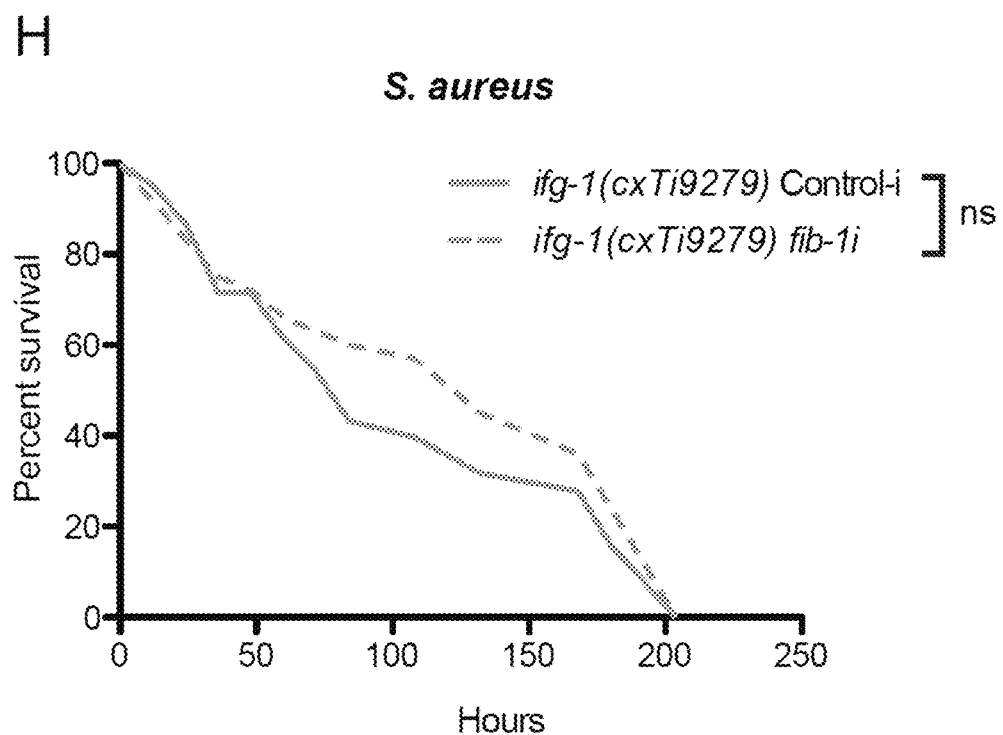

FIG. 10: shows that fib-1/Fibrillarin reduction induces translation suppression reporter irg-1. (A,B) 12-hour S. aureus infection induces $P_{irg-1}$GFP reporter. Error bars represent mean ±s.e.m. (C,D,E) fib-1 knockdown induces $P_{irg-1}$GFP reporter and mRNA expression of irg-1. Error bars represent mean ±s.e.m. (F) ifg-1(cxTi9279) exhibits significantly extended survival compared to wildtype N2 upon S. aureus infection (P<0.0001, log-rank test). (G,H) fib-1 knockdown significantly increases the survival of wildtype N2 (P<0.0001, log-rank test) but not of ifg-1(cxTi9279) (P=0.74, log-rank test) upon S. aureus infection. Survival experiments were performed three times independently. Scale bars represent 100 μm. P<0.01, *P<0.001, ****P<0.0001, ns non-significant, unpaired t-test.

Figure 11:
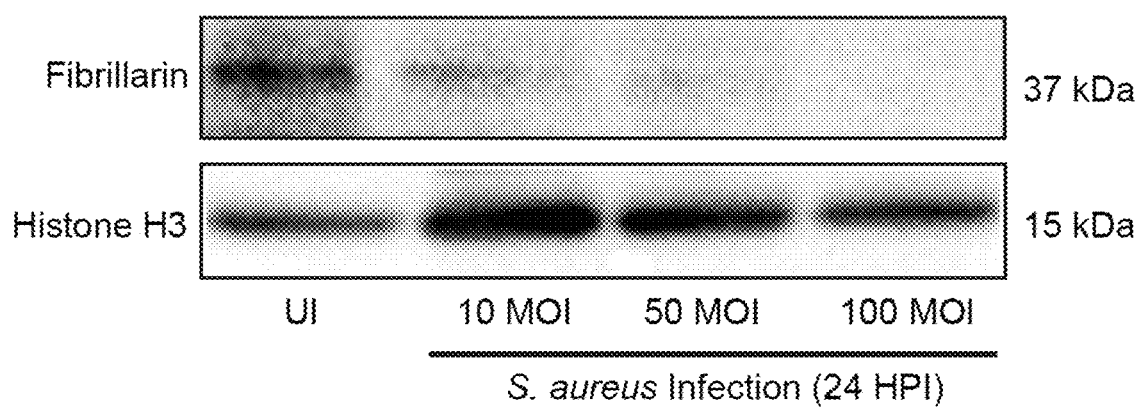
Figure 11:
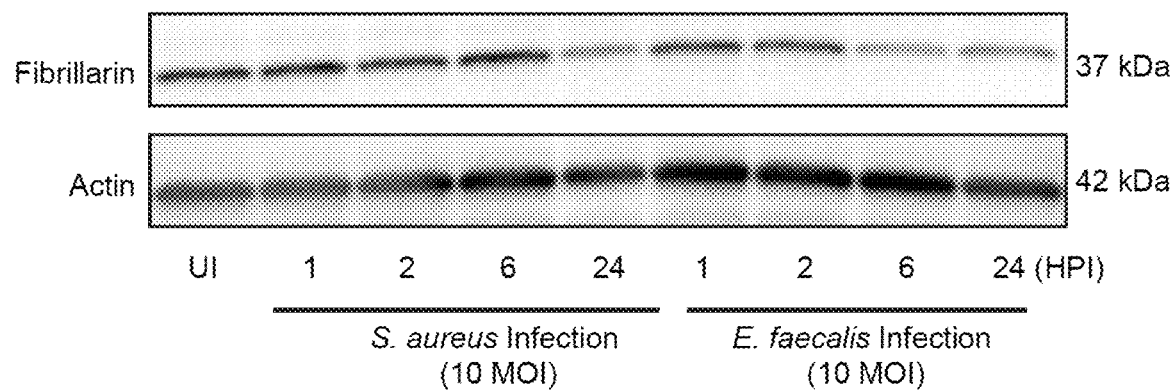
Figure 11:
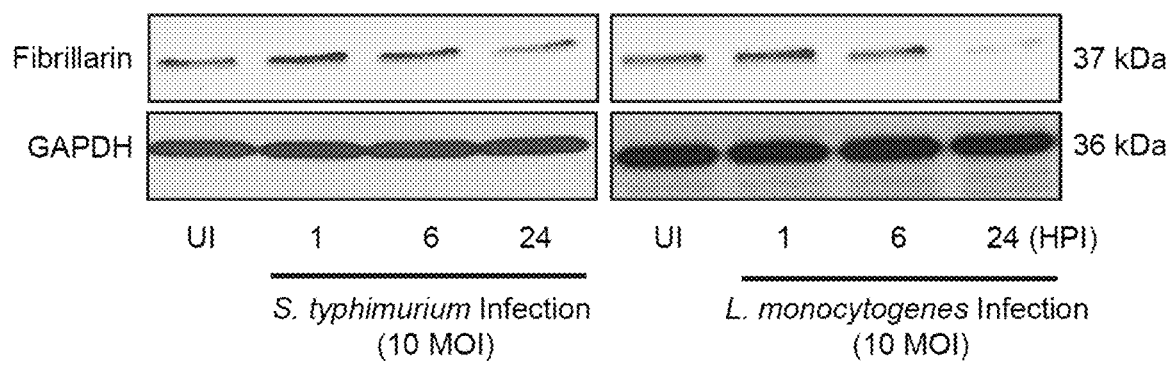
Figure 11:
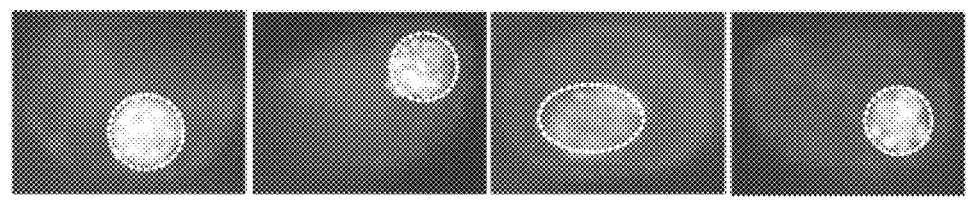
Figure 11:
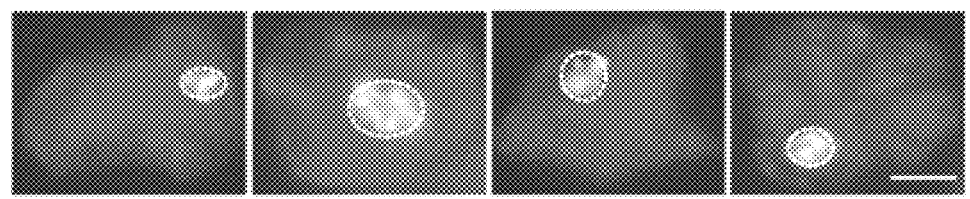
Figure 11:
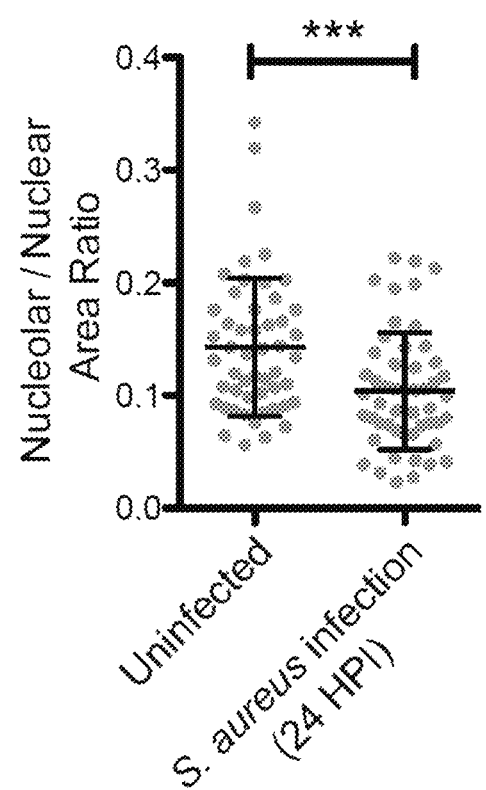
Figure 11:
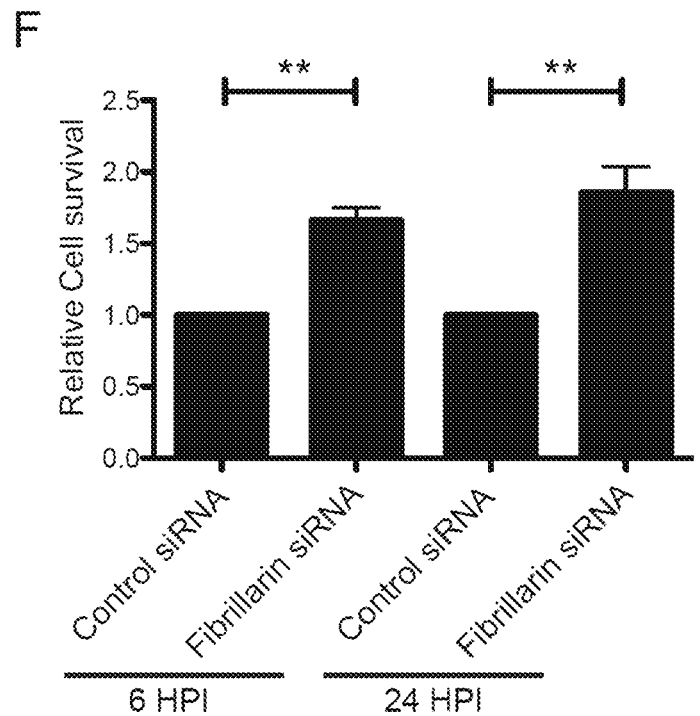
Figure 11:
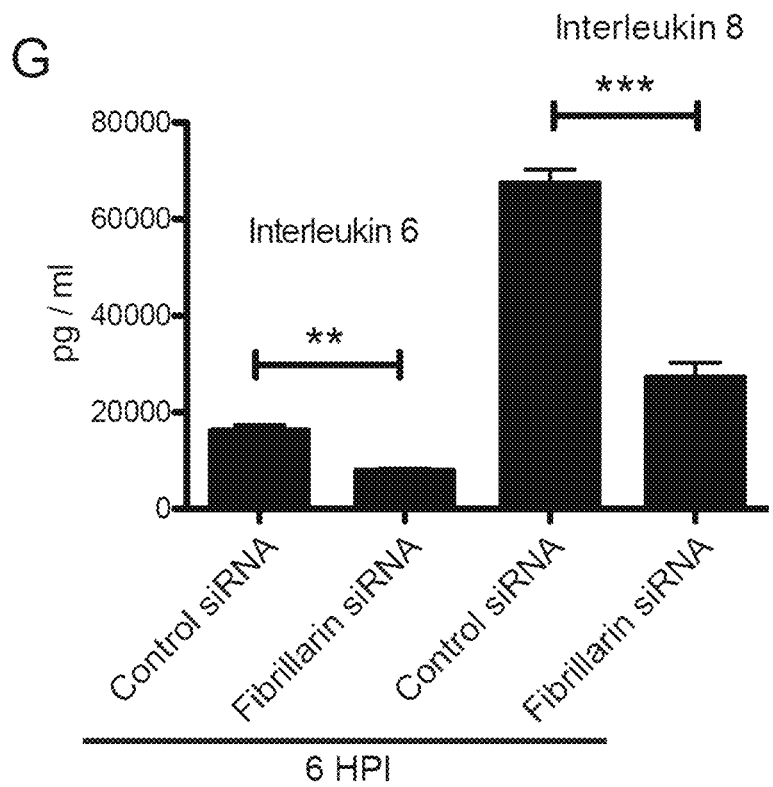
Figure 11:
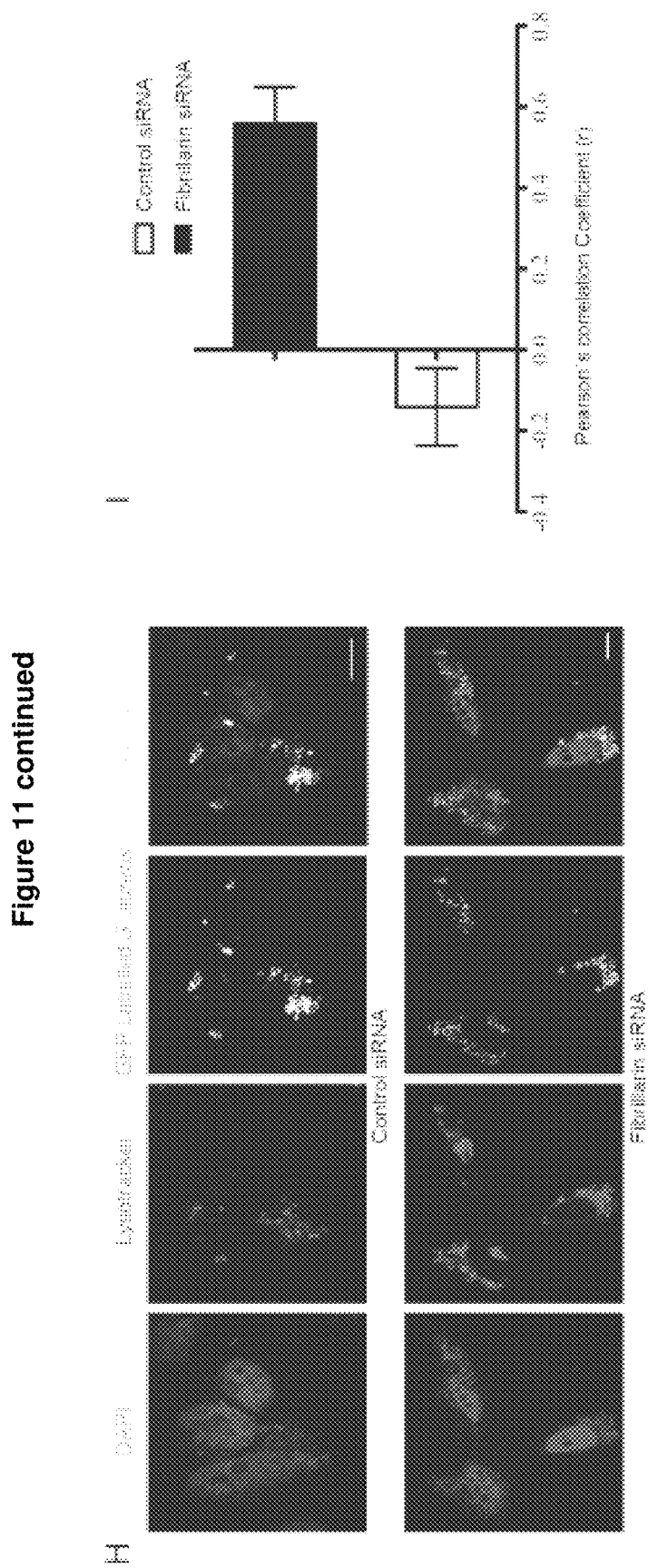
Figure 12:
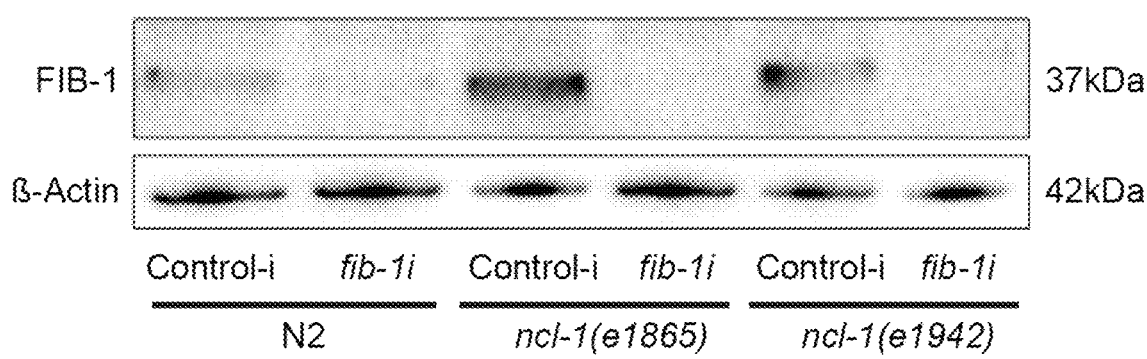
Figure 12:
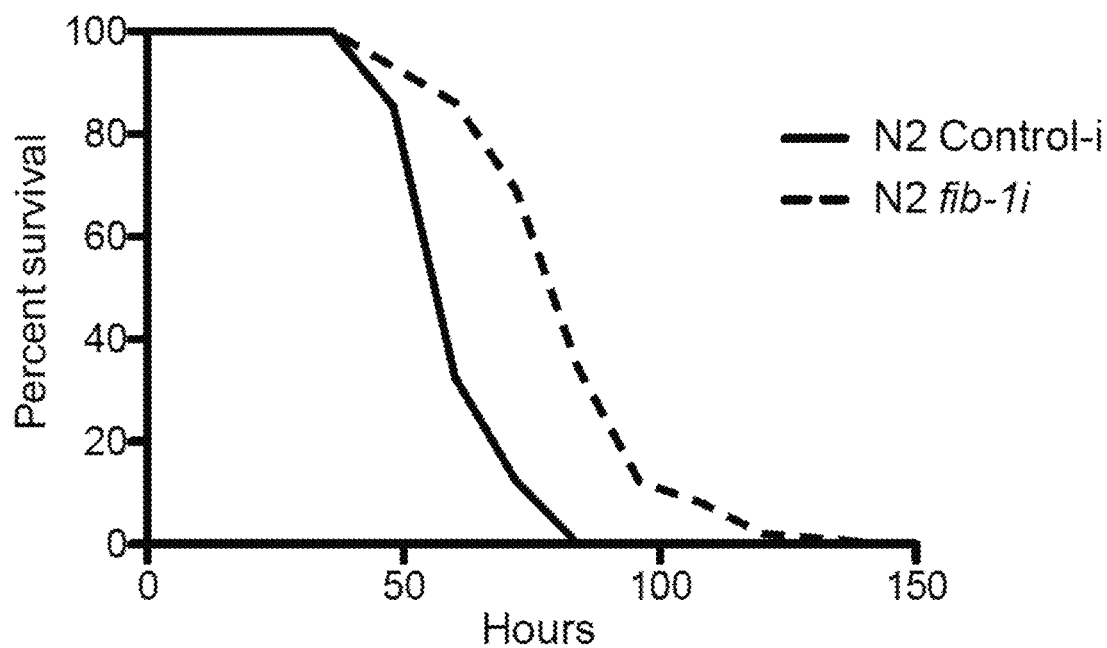
Figure 12:
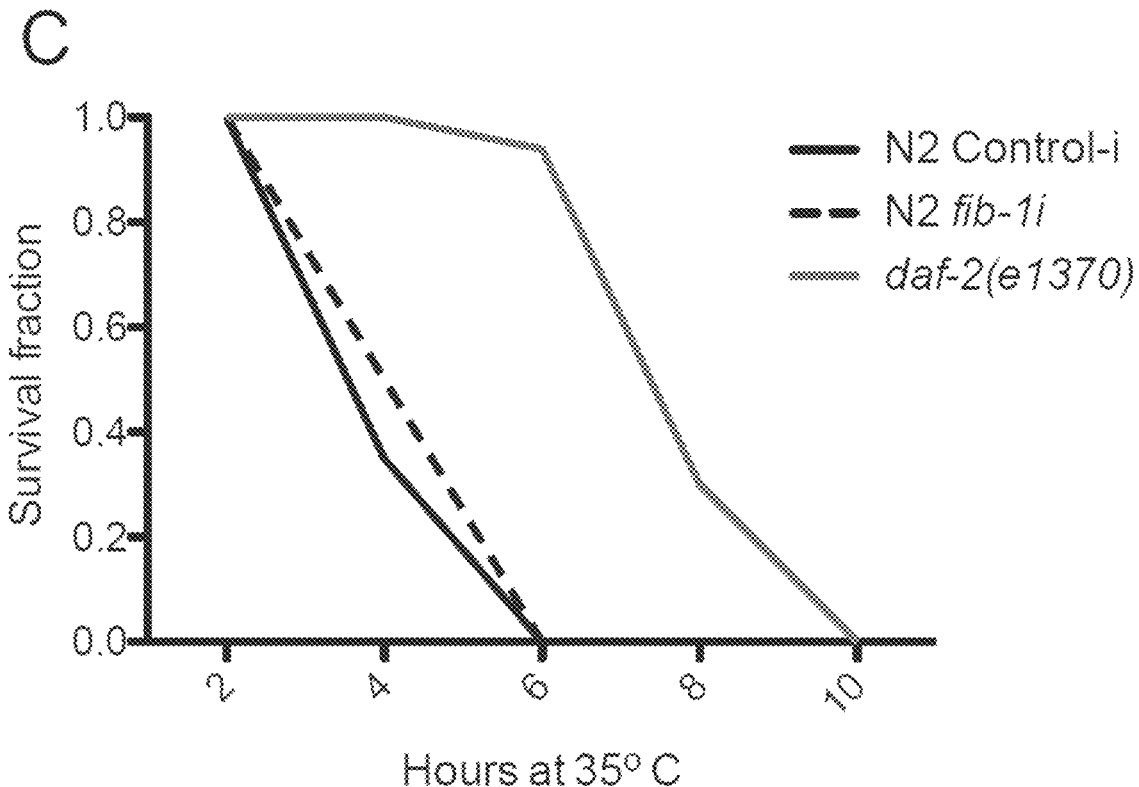
Figure 12:
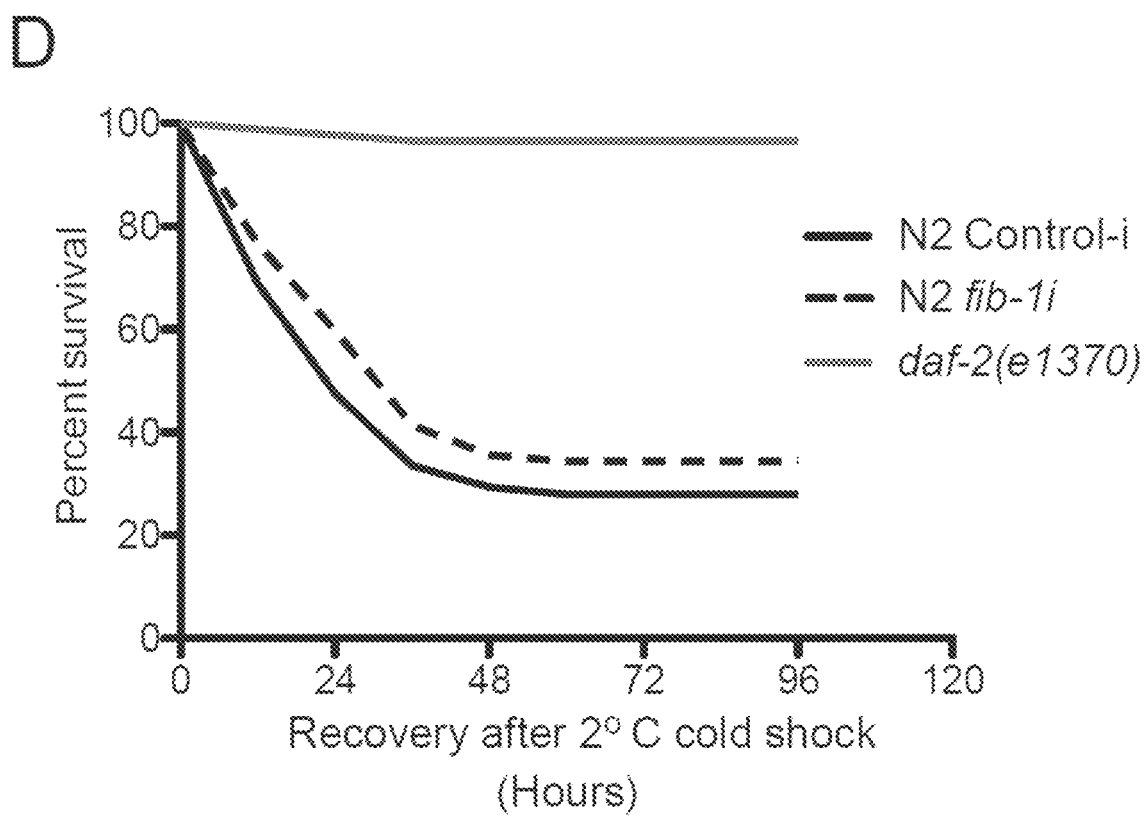
Figure 12:
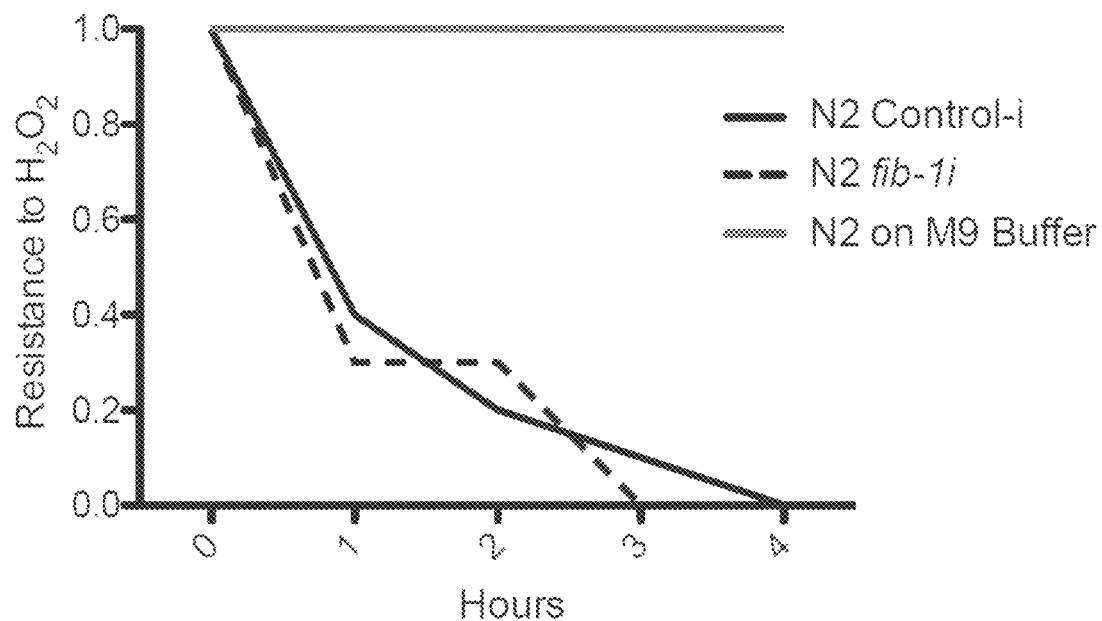
Figure 12:
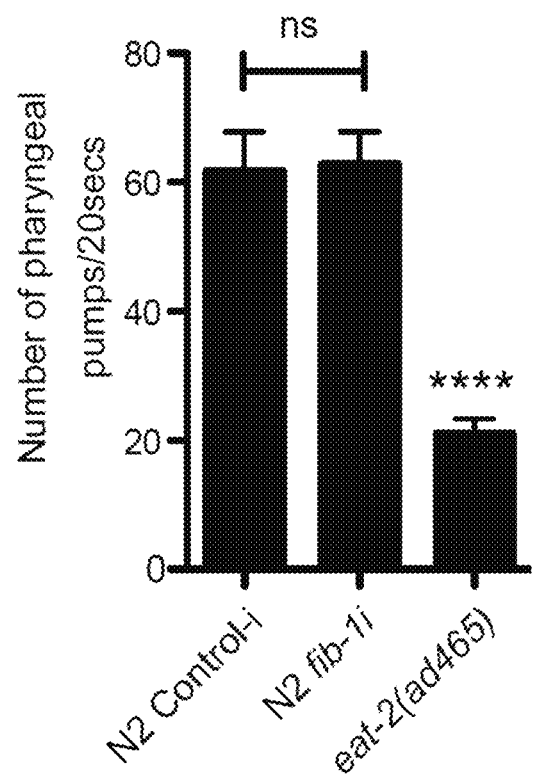
Figure 12:
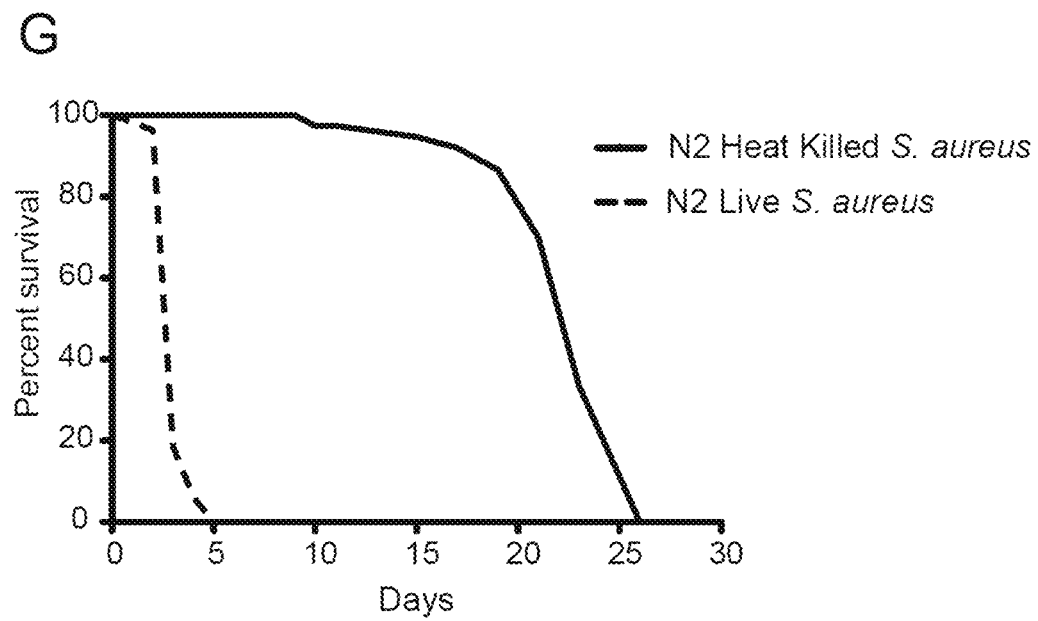

FIG. 11: shows that Fibrillarin reduction protects mammalian cells against bacterial pathogens. (A) S. aureus infection leads to a reduction of Fibrillarin levels in HeLa cells. (B,C) Mouse bone marrow macrophages show a reduction in Fibrillarin 24 hours post-infection with S. aureus, E. faecalis, S. typhimurium and L. monocytogenes. (D,E) 24-hour S. aureus infection leads to a reduction in nucleolar size of THP1 macrophages. Error bars represent mean ±s.d. (F) Fibrillarin siRNA improves cell survival relative to control siRNA after 6 and 24 hours of S. aureus infection in HeLa cells. Error bars represent mean ±s.e.m., one-way ANOVA. (G) Six hours after S. aureus infection ELISA results show a decrease in pro-inflammatory cytokines interleukin 6 and 8 after Fibrillarin siRNA treatment in HeLa cells. Error bars represent mean ±s.e.m. (H,I) HeLa cells infected with GFP labeled S. aureus and stained with lysotracker show increased co-localization of bacteria with lysosomes in cells treated with Fibrillarin siRNA. P<0.01, *P<0.001, unpaired t-test. Scale bars represent 4 μm (D) and 10 μm (H). UI —Uninfected, HPI—Hours Post Infection, MOI—Multiplicity of Infection FIG. 12: (A) fib-1 RNAi from larval stage L3 up to day 1 adulthood (~30 hours) is sufficient to reduce the levels of FIB-1 protein in wildtype N2 and ncl-1 mutants. (B) fib-1 RNAi significantly enhances P. aeruginosa infection tolerance in wildtype N2 worms (P<0.0001, log-rank test). Survival experiments were performed three times independently. (C,D,E) fib-1 RNAi does not significantly alter heat tolerance, cold shock recovery, or oxidative stress tolerance in wildtype N2 worms. (F) fib-1 RNAi does not affect pharyngeal pumping rate. Error bars represent mean ±s.d. ****P<0.001, unpaired t-test. (G) Wildtype N2 worms treated with heat killed *S. aureus* live significantly longer than the worms treated with live *S. aureus* (P<0.0001, log-rank test).

Figure 13:
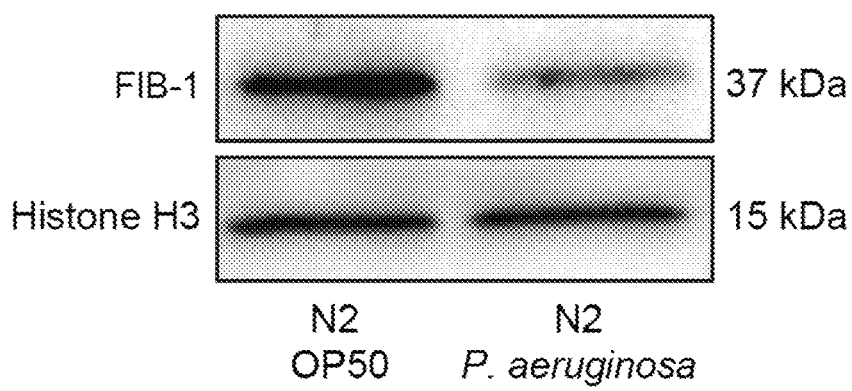
Figure 13:
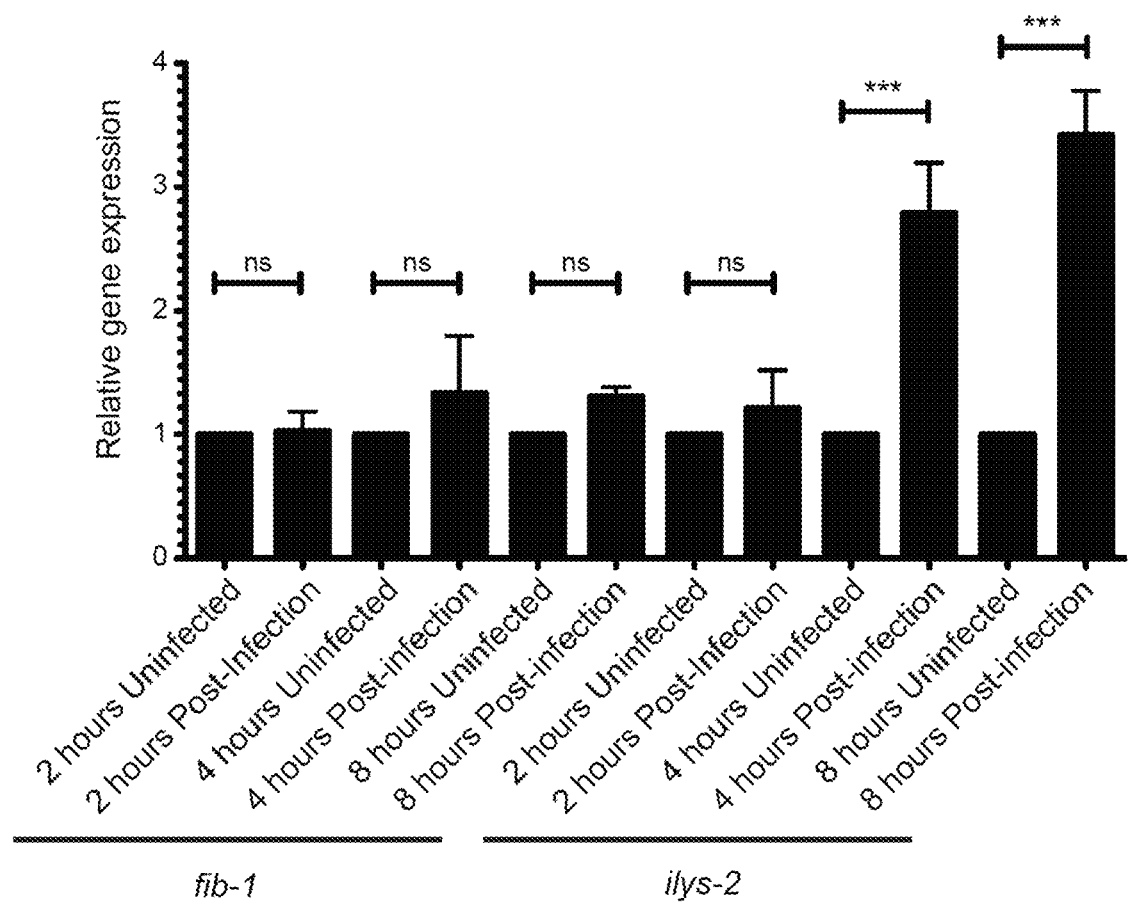
Figure 13:
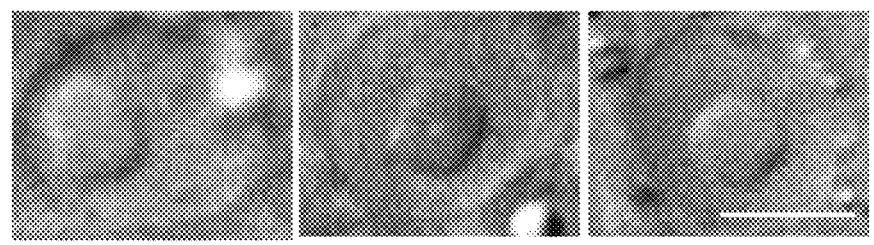
Figure 13:
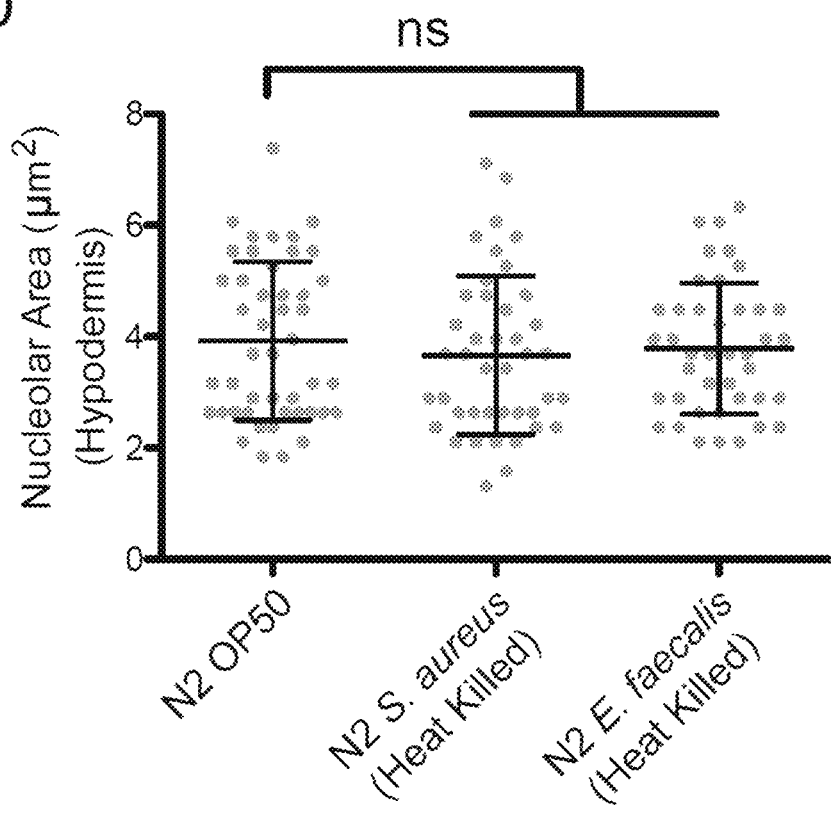

FIG. 13: (A) FIB-1 levels are significantly reduced in wildtype N2 after *P. aeruginosa* infection. Error bar represents mean ±s.e.m. of three independent biological replicates. *P<0.05, unpaired t-test (B) 2, 4 and 8 hour *S. aureus* infection does not change the expression levels of fib-1. ilys-2 levels are increased significantly after 4 and 8 hours of infection and serves as a positive control for the experiment. Error bars represent mean ±s.e.m. from three independent biological replicates ***P<0.001, one-way ANOVA. (C,D) Treatment with heat-killed *S. aureus* and *E. faecalis* does not alter nucleolar size of 20 hypodermal cells in wildtype N2 worms. Error bars represent mean ±s.d. ns non-significant, unpaired t-test. Scale bar represents 5 pμm.

Figure 14:
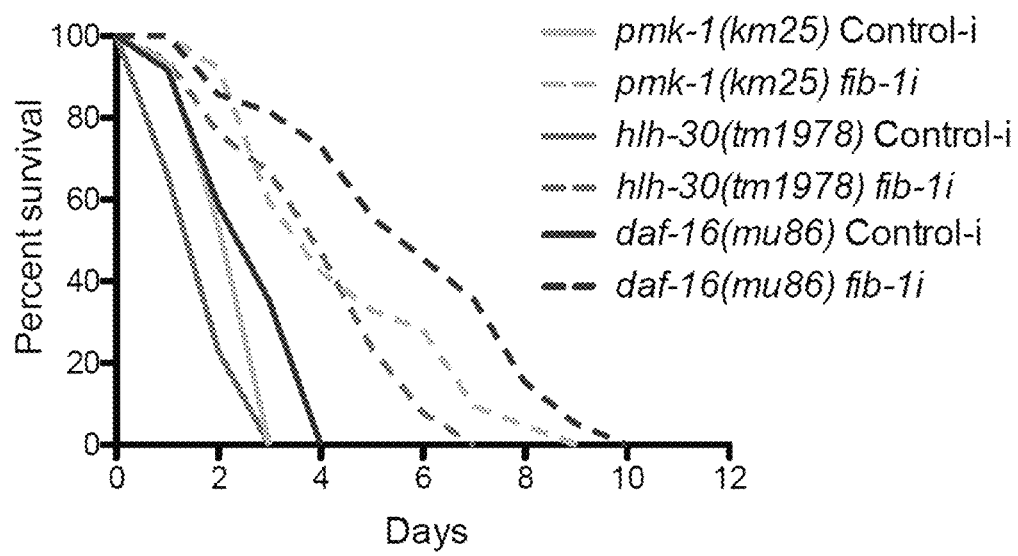
Figure 14:
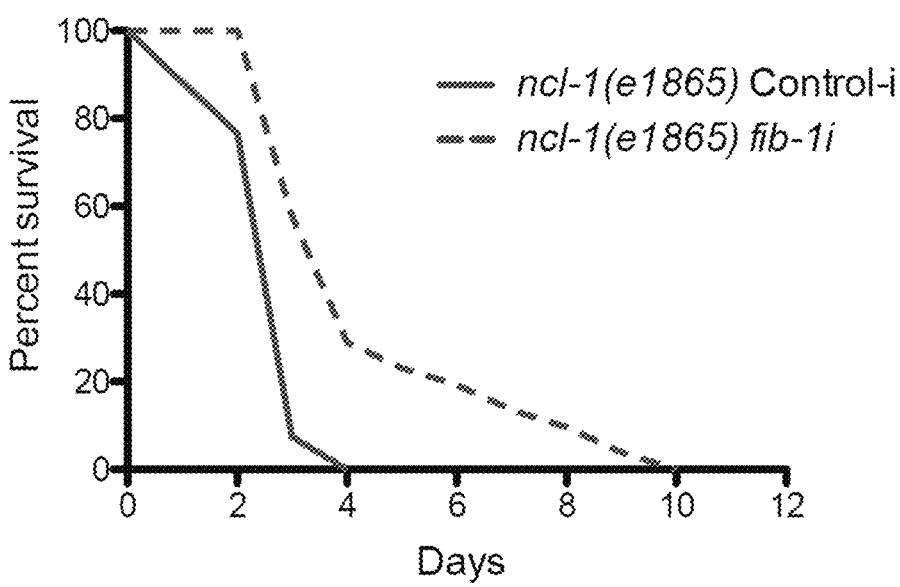
Figure 14:
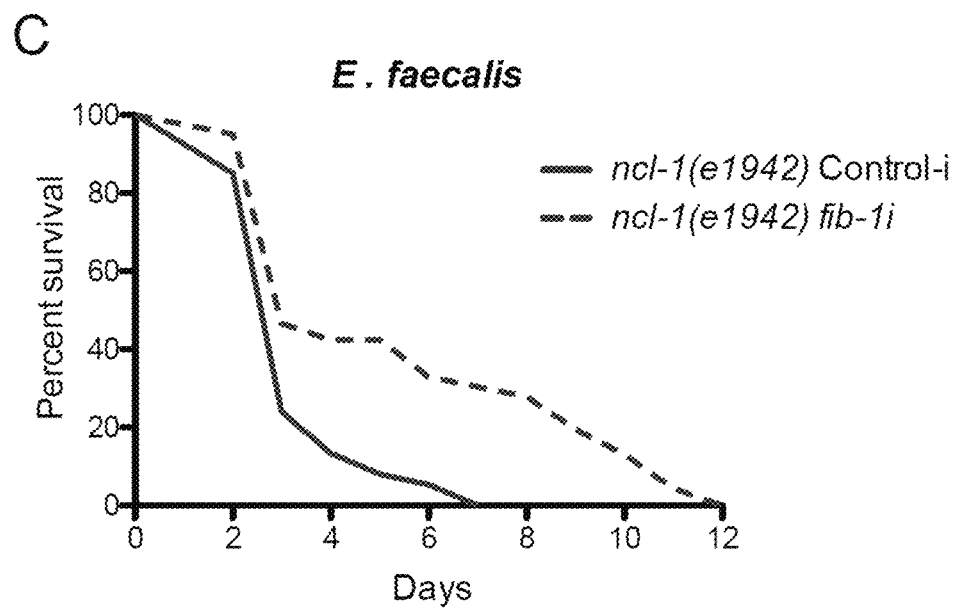

FIG. 14: (A,B,C) fib-1 RNAi significantly improves the survival of infection sensitive pmk-1(km25) (P<0.0001, log-rank test), hlh-30(tm1978) (P<0.0001, log-rank test), daf-16(mu86) (P<0.0001, log-rank test) and ncl-1(e1865 and e1942) mutants (P<0.0001, log-rank test) upon *E. faecalis* infection. The experiments were performed three times independently.

Figure 15:
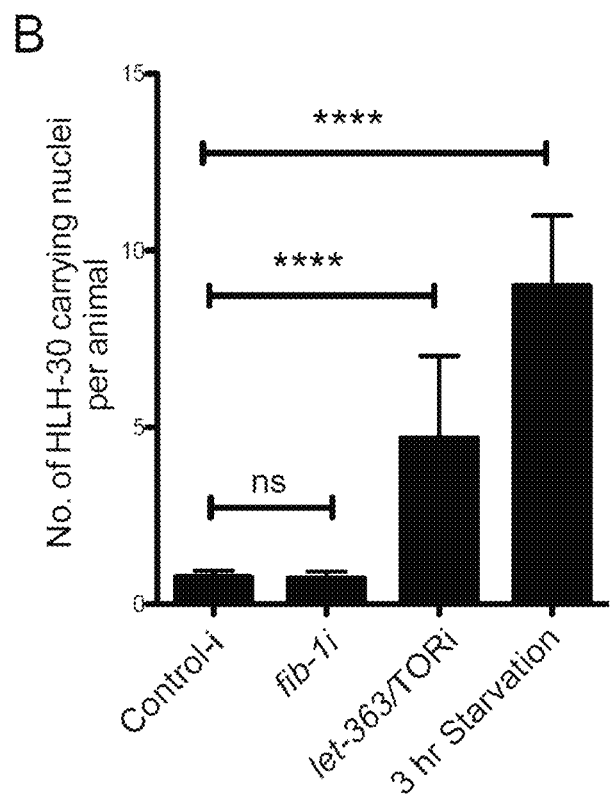
Figure 15:
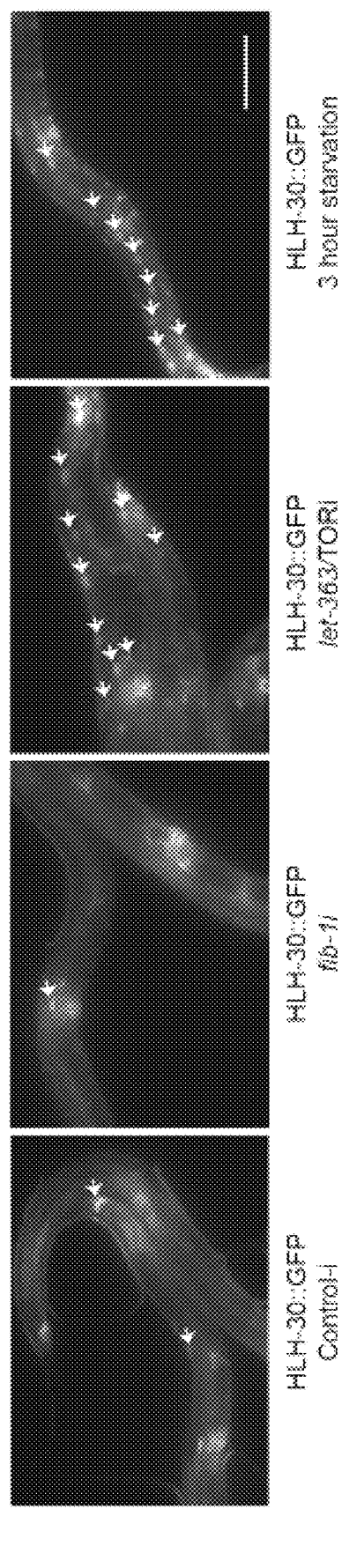

FIG. 15: (A,B) fib-1 RNAi does not affect HLH-30 sub-cellular localization while let-363/TOR RNAi and 3 hour starvation significantly induce HLH-30 nuclear localization. White arrows show the nuclei with HLH-30::GFP. Error bars represent mean ±s.d. ****P<0.001, unpaired t-test. Scale bar represents 100 μm.

Figure 16:
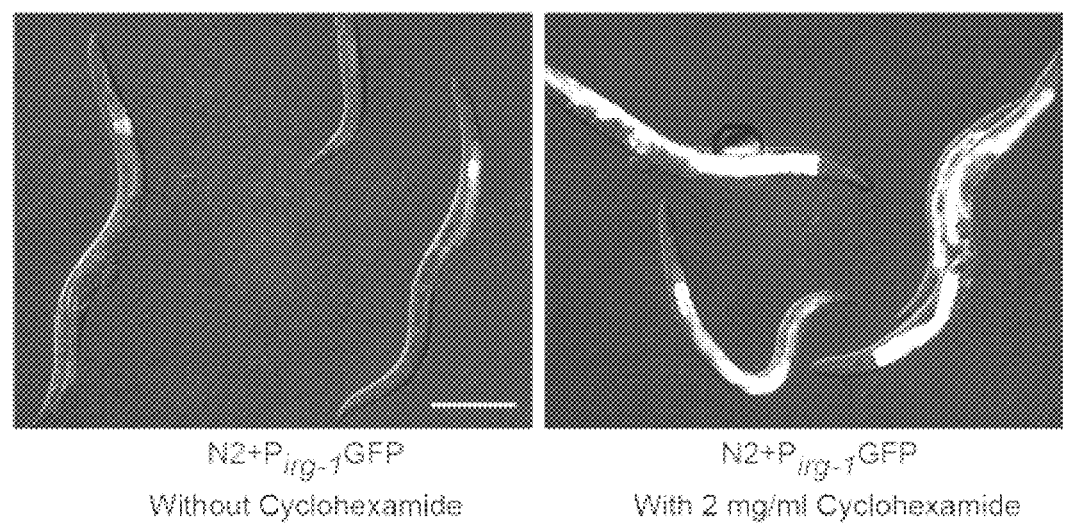
Figure 16:
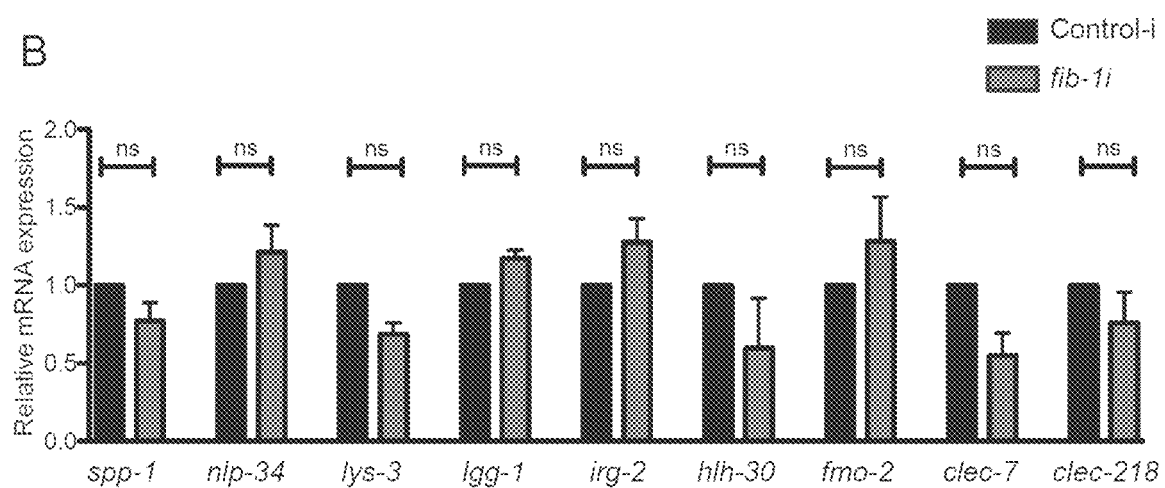
Figure 16:
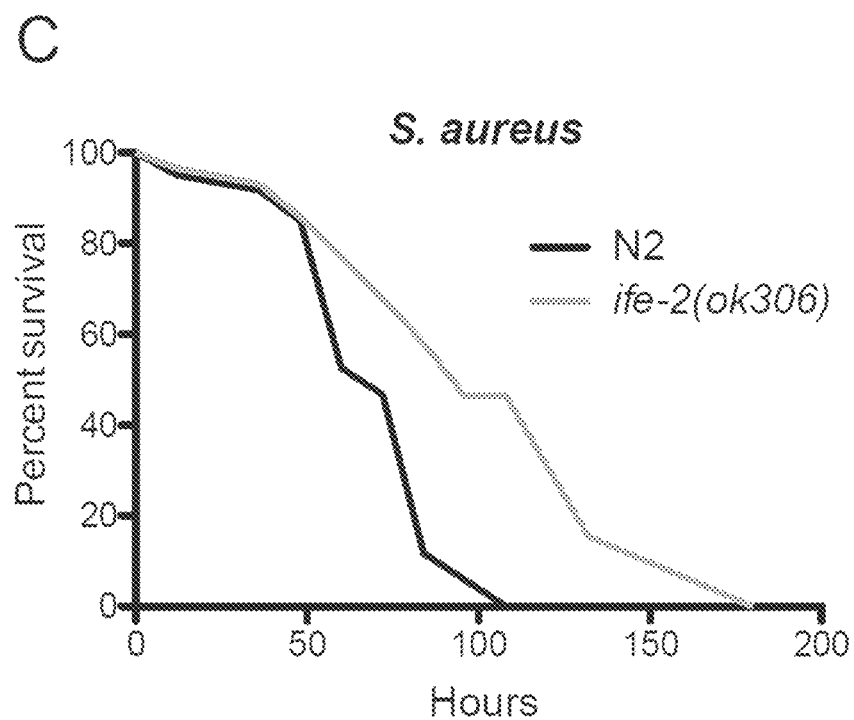

FIG. 16: (A) P$_{irg-1}$GFP reporter is strongly induced by a 3-hour Cyclohexamide (2 mg/ml) treatment. (B) fib-1 RNAi does not significantly change the expression of infection related genes. Error bars represent mean ±s.e.m. from three independent biological replicates, ns non-significant one-way ANOVA. (C) ife-2(ok306) is significantly longer-lived than wildtype N2 worms upon *S. aureus* infection (P=0.0034, log-rank test). The experiments were performed three times independently. Scale bar represents 200 μm.

Figure 17:
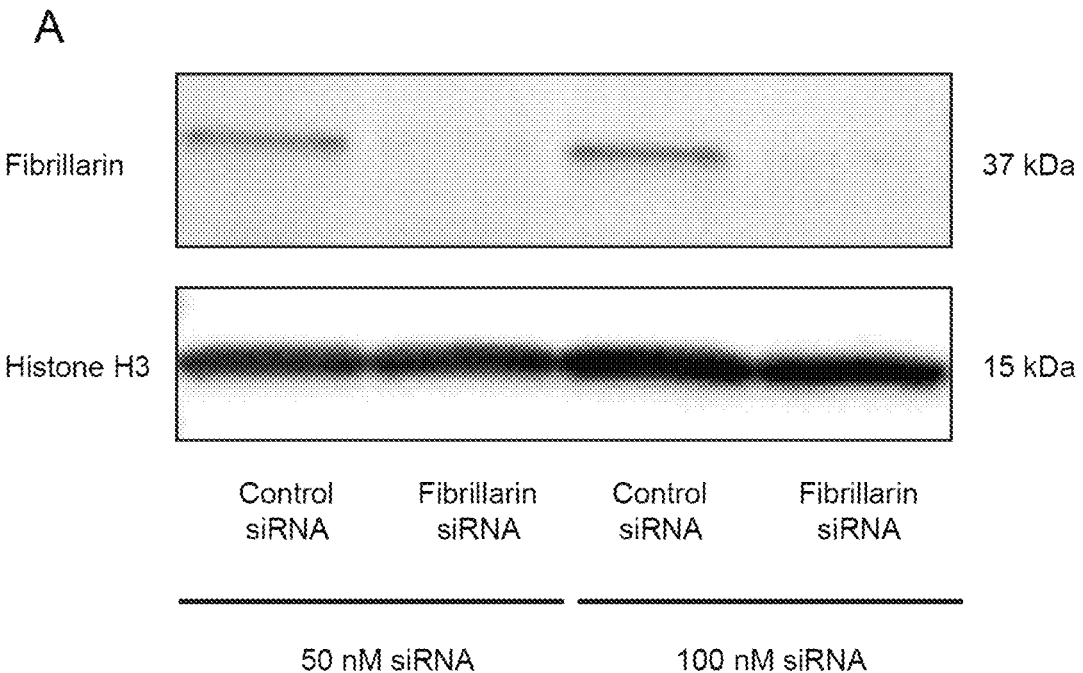
Figure 17:
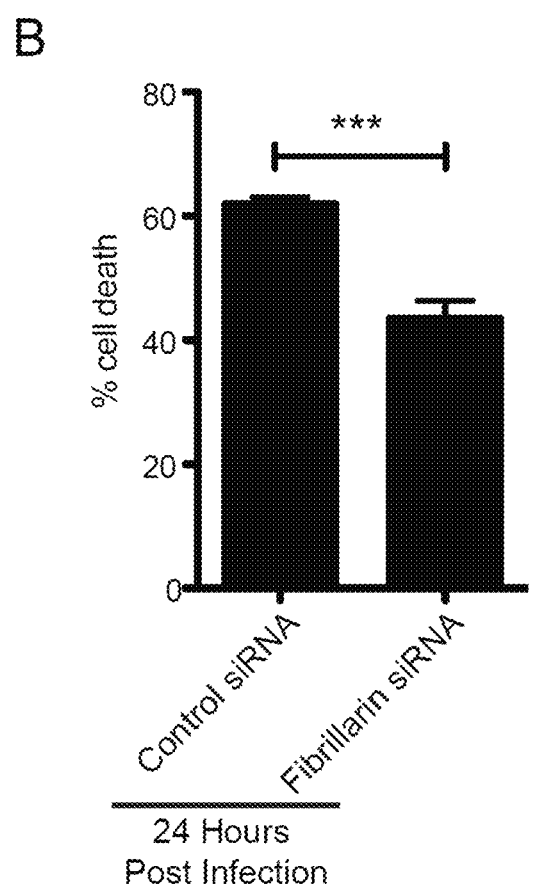
Figure 17:
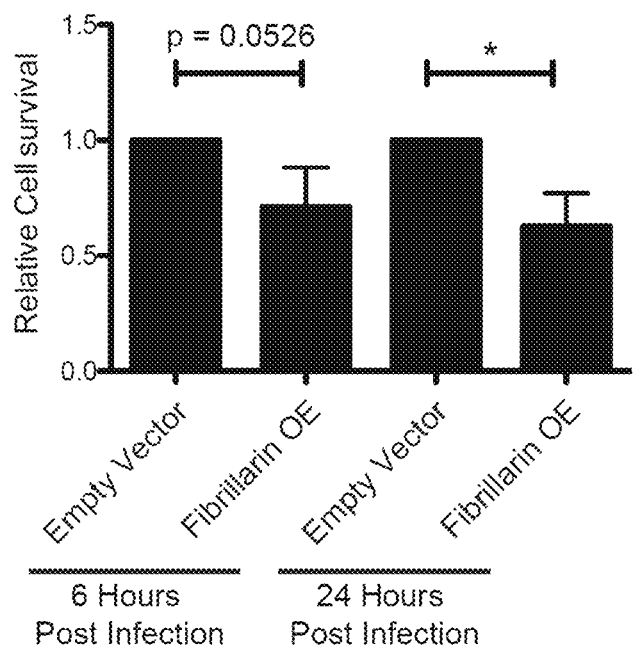
Figure 17:
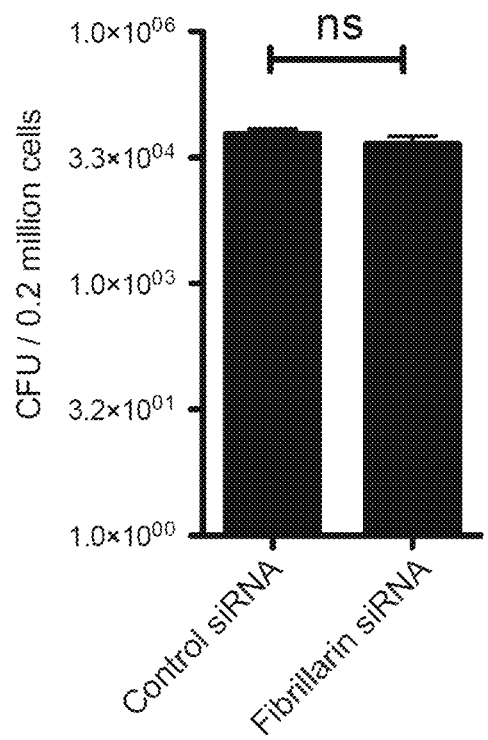
Figure 17:
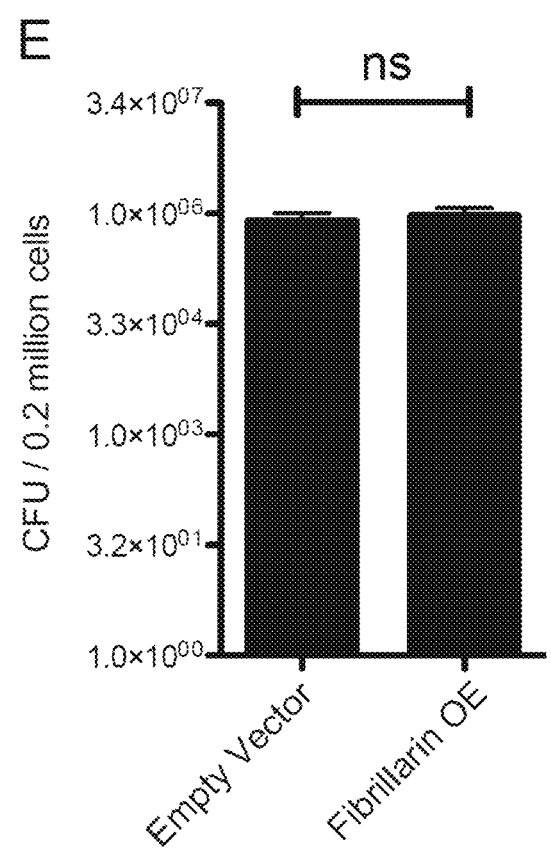

FIG. 17: (A) 50 and 100 nM Fibrillarin siRNA sufficiently knocks down the levels of Fibrillarin protein in HeLa cells. (B) Fibrillarin siRNA significantly reduces infection induced cell death as measured by LDH cytotoxicity assay (***P<0.001, unpaired t-test, error bars represent mean ±s.e.m.). (C) Fibrillarin over-expression reduces cell survival relative to control (empty vector) after 6 and 24 hours of *S. aureus* infection in HeLa cells. Error bars represent mean ±s.e.m. *P<0.05, one-way ANOVA. (D,E) Fibrillarin siRNA and over-expression do not alter bacterial uptake in HeLa cells, relative to respective controls, as measured by CFU analysis. Error bars represent mean ±s.d., ns non-significant, unpaired t-test.

EXAMPLES

Material and Methods

*C. elegans* Strains

All the worm strains were grown using standard procedures at 20° C. unless otherwise noted. Strains carrying glp-1(e2141) mutation were maintained at 15° C. and shifted to 25° C. for inducing germlineless phenotype. The strains used for the experiments were: N2 (wildtype), eat-2(ad465), ncl-1(e1865), ncl-1(e1942), eat-2(ad465);ncl-1(e1865), eat-2(ad465);ncl-1(e1942), isp-1(qm150), isp-1(qm150);ncl-1 (e1942), glp-1(e2141), glp-1(e2141);ncl-1(e1942), daf-2 (e1370), daf-2(e1370);daf-16(mu86), cguIs001 (FIB-1::GFP), eat-2(ad465)+cguIs001, ncl-1(e1942)+cguIs001 and eat-2(ad465);ncl-1(e1942)+cguIs001. dhEx1007 and dhEx1008 ncl-1 extrachromosomal transgenic strains were generated by injecting fosmid DNA WRM0611AC10 (ncl-1::TY1 EGFP) (30 ng/μl) and a co-injectable marker (myo-2::mcherry at 10 ng/μl) in N2 strain and further crossed into eat-2(ad465), eat-2(ad465);ncl-1(e1865) and eat-2(ad465); ncl-1(e1942) backgrounds. The transgenic worms were maintained by selecting the worms showing the expression of the co-injected marker.

Killing assay plate preparation

*S. aureus* (strain MW2-WT), *E. faecalis* (strain ATCC 29212) and *P. aeruginosa* (strain PA14) were used for infection in *C. elegans*. *S. aureus* was grown in tryptic soy broth (TSB) medium. *E. faecalis* was grown in Brain Heart Infusion (BHI) medium. *P. aeruginosa* was grown in lysogeny broth. 20 μL of saturated overnight bacterial cultures were spread on tryptic soy agar (TSA) with 10 μg/mL nalidixic acid (Sigma, NAL) for *S. aureus*, BHI with 10 μg/mL NAL for *E. faecalis* and modified NGM, 0.35% peptone, for *P. aeruginosa*. The plates were then incubated at 37° C. overnight.

*C. elegans* killing assay

Age synchronized young adults were transferred to killing assay plates and the survival assay was carried out at 25° C. For each condition, three technical replicates were set up with 20 worms on each plate. Scoring was performed every 12 hours for *S. aureus* and *P. aeruginosa* and every 24 hours for *E. faecalis*. Worms were scored as dead if they failed to respond to gentle touch with a worm pick. Animals that crawled off the plate or had vulval explosion were censored.

Lifespan Analyses

All the lifespan analyses experiments were performed in three independent biological replicates at 20° C. as previously reported. Animals that crawled off the plates, burst due to a ruptured vulva or had internal hatching of the eggs were censored from the experiment. RNAi lifespan analysis experiments were carried out following previously described protocol (Kamath, R. S., et al.; *Genome Biol* 2, RESEARCH0002 (2001). All RNAi treatments were performed throughout development and adulthood except let-363/TOR and fib-1, which were initiated on the first day of adulthood. For BDR lifespan analyses, the method followed was the same as described in Panowski, S. H., et al.; *Nature* 447, 550-5 (2007).

90 worms were used for each bacterial concentration to be tested and the worms were scored every 3-4 days. The worms were transferred to freshly prepared bacterial conditions on each day of scoring. BDR medium containing FUdR (1 μg/ml) was used for the first two weeks of the experiment to prevent progeny production. All the lifespan experiments were performed in a blinded manner. Mantel-Cox Log Rank method was used for statistical analysis.

ciRT-PCR

Age synchronized young adults were washed three times in M9 buffer and then transferred to tryptic soy agar (TSA) plates with 10 μg/mL nalidixic acid (sigma, NAL) carrying either *S. aureus* or heat-killed OP50 at 25° C. At the indicated times, animals were harvested and washed twice with M0 before lysis. Worms were lysed in QIAzol Lysis Reagent (Qiagen). RNA was isolated using RNeasy Mini kit (QIAGEN). cDNA synthesis was performed using iScript cDNA synthesis Kit (BioRoad). Experiments were performed according to manufacturer's instructions. qPCR was performed on a ViiA 7 Real-Time PCR System (Applied Biosystems) using Power SYBR Green master mix (Applied Biosystems). All the experiments were performed three times independently and the results were normalized to snb-1.

rRNA Analysis

Age-matched day 1 adult worms were collected in TRIzol® (Invitrogen) and snap-frozen in liquid nitrogen. RNA extraction was performed using RNeasy Mini kit (QIAGEN). Levels of rRNA were analyzed by running total RNA, extracted from the same number of worms on Agilent 4200 TapeStation System® following High Sensitivity RNA ScreenTape System protocol (Agilent). rRNA levels were also examined by running total RNA extracted from the same number of worms on agarose gels. NorthernMax® Kit protocol was followed for running RNA gels. The gels were imaged with Alpha Innotech Multilmage II.

[For RNA extraction: n=100 worms/replicate, 3 independent replicates]

Western Blotting

Day 1 adult worms (50) were collected in Laemmli lysis buffer and snap-frozen in liquid nitrogen. The samples were then boiled at 95° C. for 5 minutes, ultrasonicated for 10 cycles and loaded on 4-15% Mini-PROTEAN® TGXTM Precast Protein Gels. After separation, proteins were blotted on a nitrocellulose membrane and probed with the following antibodies against: RPS-6 (abcam® ab70227, 1:1000), RPS-15 (antibodies-online.com ABIN503870, 1:1000), Fibrillarin (Novus Biologicals NB300-269, 1:1000) and β-Actin (abcam® ab8224, 1:5000). [For all Western Blots: n=50 worms/replicate, 3 independent replicates]

For Drosophila western blots, 5 females were homogenised in 100 μl of RIPA lysis buffer carrying 1X Complete mini protease inhibitor (EDTA free) (Roche). Extracts were cleared by centrifugation and protein content determined with BOA assay, 30 μg of total protein was loaded on precast gels (Bio-Rad Any KD, Mini-PROTEAN® TGXTM). The proteins were transferred to nitrocellulose membranes and probed with the same antibodies as above.

[For all Western Blots: n=5 flies/replicate, 3 independent replicates]

Immunofluorescence

Immunofluorescence was performed on 10 μm thick cryosections of mouse tissues derived from kidney, liver and brain. The samples were fixed with 4% Paraformaldehyde (PFA) for 15 minutes at room temperature (RT) followed by three washes with PBS at RT. The samples were then blocked with 5% Normal Donkey Serum in PBS with 0.1% Triton-X for 30 minutes at RT followed by an over-night incubation at 4° C. with the primary antibody against Fibrillarin (abcam® ab166630, 1:200). After three subsequent washes with PBS, the samples were then probed with the secondary anti-rabbit antibody at RT for one hour followed by three more washes with PBS. The samples were mounted with ProLong® Gold Mounting Medium (ThermoFisher Scientific). Immunofluorescence quantification represents three independent biological replicates with each replicate representing 3 mice (DR) and 2 mice (IRS1 KO). Imaging and quantification of the experiments were performed in a blinded manner.

Drosophila guts and fat bodies were dissected out in PBS followed by immediate fixation with 4% PFA in PBS and permeabilization for 10 minutes at RT with 0.3% Triton X-100 in PBS (PBST). Blocking, primary and secondary antibody incubation were done in 5% BSA in PBST using Fibrillarin (Novus Biologicals NB300-269, 1:250) as the primary antibody and goat antimouse conjugated to Alexa Fluor 488 (Invitrogen Inc., 1:1000) as the secondary antibody. Hoechst 33342 was applied at 1:1000 for staining nuclei. Tissues were extensively washed with PBST after antibody treatments and finally mounted on glass slides with 80% glycerol in PBS. The quantification represents three independent biological replicates with each replicate representing 5 dissected flies. Imaging and quantification of the experiments were performed in a blinded manner.

For staining human muscle biopsies, samples were thawed at RT. Then the samples were blocked with 5% milk in PBS with 0.05% Tween (PBST) for 30 minutes at RT, followed by three washes with PBST. The primary antibody, Rabbit-anti-Fibrillarin (abcam® ab166630, 1:600 in PBST), was incubated overnight at 4° C. After three washes with PBST, samples were incubated with the secondary goat-anti-rabbit-conjugated-Alexa647 antibody (Molecular Probes, 1:1000 in PBST) for 1 hour at RT, followed by three washes in PBST and one wash in PBS containing DAPI (0.5 μg/mL, Sigma-Aldrich, Saint Louis, Mo., USA). Slides were mounted with Aqua Poly-Mount® (Polysciences Inc, Niles, Ill., USA). All samples were stained on the same day with the same antibody mixes.

Imaging and Quantification

DIC microscopy was used to perform all the nucleolar imaging. Hypodermal, germ cell and pharyngeal muscle nucleoli of age-matched day 1 adults were imaged using 100× magnification with Axio Imager Z1 (Zeiss). Nucleolar area was quantified manually with the freehand tool using Fiji software. Details of the nucleolar size analysis are given in Supplementary Table 2. Worms carrying FIB-1::GFP and NCL-1::GFP transgenes were imaged using 63× magnification with Axio Imager Z1 (Zeiss). Immunofluorescent images were acquired using a laser-scanning confocal microscope (TCS SP5-X; Leica), equipped with a white light laser, a 405- diode UV laser, and a 100× objective lens (HCX Plan-Apochromat CS 100× oil, 1.46 NA). For human muscle biopsies, a total 15 representative fields with a 63× objective from each muscle sample were obtained, using the DM5500 fluorescent microscope (Leica) and the LAS AF software (version 2.3.6, Leica). Anti-Fibrillarin was detected with the Y5 cube, and nuclei were detected with the A4 cube. The area of the nucleolar and nuclear regions was quantified manually with the freehand tool, and subsequently the ratio of nucleolar/nuclear area was calculated. For the human samples, the average ratio of nucleolar/nuclear area (from an average of 100.4 (±28.9) nuclei) per sample was used for the analyses.

DIC microscopy was used to perform all the nucleolar imaging. Hypodermal cells of age-matched day 1 adults were imaged using 100× magnification with Olympus IX81. Freehand tool software from Fiji was used for nucleolar area quantification. FIB-1::GFP, HLH-30::GFP and N2+$P_{irg-1}$ GFP worms were imaged using Olympus IX81 and Axio Imager Z1(Zeiss).

Mammalian cell culture

Human epithelial cell lines, HeLa was obtained from ATCC. The cells were cultured in Dulbecco's modified Eagle's medium (DMEM) supplemented with 10% fetal calf serum (FCS). The cells were maintained at 37° C. with 5% $CO_2$ in a humid atmosphere.

Bone marrow derived macrophages were prepared from 8-12 weeks old female C57BL/6J mice maintained and bred in the animal facility of Center for Molecular Medicine, University of Cologne, Germany. Mice were sacrificed by cervical dislocation and bone marrows from the femurs were flushed using RPMI medium. The flushed cells were centrifuged and resuspended in RPMI containing 10% FBS. Cells were seeded in culture dishes and allowed to differentiate into macrophages in medium supplemented with 20% L929 cell-culture supernatant for 7 days. Non-adherent cells were removed on days 2 and 4, and adherent macrophages were used from day 7 onwards.

THP1 monocytes were obtained from ATCC. The cells were maintained in RMPI 1640 media, supplemented with 10% FCS. For differentiation of THP1 monocytes into macrophages, Phorbol 12-myristate 13-acetate (PMA, Sigma, P8139) was used. Briefly, THP1 derived monocytes were incubated in 10% FCS RPMI 1640 media supplemented with 25 ng/ml of PMA for 24 hours. The differentiated cells were used for infection.

Fibrillarin knockdown and overexpression siGenome siRNA for Fibrillarin was obtained from Dharmacon (GE Healthcare Life Sciences). HeLa cells were treated with 100 nM of siRNA 48 hours before infection using Dharmafect-2 (GE Healthcare Life Sciences) according to the manufacturer's protocol. For mammalian plasmid transfection, plasmid carrying human fibrillarin fused to EGFP, cloned under CMV promoter (p-EGFP C1) was procured from Addgene (Catalog Number: 26673).

The empty vector only carrying the EGFP was used as the control. HeLa cells were transfected with the plasmids using Lipofectamine 3000 (ThermoFisher Scientific) following the manufacturer's protocol. Transfected cells were assayed for Fibrillarin and GFP expression 48 hours post-transfection and were then used for infection.

Infection in mammalian cells

A late logarithmic phase grown $S.$ $aureus$ (MW2), $E.$ $faecalis$ (ATCC 29212), $S.$ $Typhimurium$ (SL 1344), and $L.$ $monocytogenes$ (EGDe) were used at MOI 50 and MOI 10 for HeLa and Macrophages respectively. The cells were transfected with Fibrillarin siRNA or over-expression plasmid for 48 hours followed by infection. The infected cells were incubated for 10 minutes at room temperature, followed by an incubation for 30 minutes at 37° C. with 5% $CO_2$ in a humid atmosphere. After 30 min, extracellular bacteria were removed and cells were incubated for 2 hours in medium containing 50 µg/ml gentamicin and then were washed and subsequently cultured in medium containing less gentamicin (10 µg/ml). At desired time points cells were collected for western blot analysis using RIPA lysis buffer.

Cell viability assay

Cell viability was measured using a Lactate Dehydrogenase (LDH) Cytotoxicity Assay Kit (CytoTox 96 Non-Radioactive Cytotoxicity Assay; Promega). Released LDH was measured according to the manufacturer's protocol. The percentage of cell death was calculated using the formula: % Cell Death=Experimental release/Maximum release ×100. Trypan Blue method was performed by treating cells with trypsin at different time points post-infection and counting viable cells using standard Trypan Blue dye exclusion assay.

Gentamycin protection assay

After $S.$ $aureus$ infection, HeLa cells were washed three times with sterile PBS and lysed with 0.3% Triton X-100 in PBS for 5 minutes at room temperature. Several dilutions of the lysate were plated on BHI plates and incubated over night at 37° C. The following day, $S.$ $aureus$ colony forming units (CFU) were counted.

Immunocytochemistry

HeLa cells were infected with GFP expressing $S.$ $aureus$ as per the above-mentioned protocol. $24h$ post infection, the cells were incubated with 250 nM lysotracker deep red (Invitrogen) for 15 minutes at 37° C. with 5% $CO_2$ in a humid atmosphere. Then the cells were washed with warm PBS and fixed at room temperature for 15 minutes in 4% paraformaldehyde. Fixed cells were washed three times with PBS and mounted on slides with ProLong Gold mounting medium containing DAPI (ThermoFisher Scientific). Images were acquired with a 60× oil PlanApo objective Numerical Aperture 1.4 at room temperature on an Olympus IX81 inverted confocal microscope equipped with PMT detectors for imaging.

Olympus Fluoview −10 ASW 4.2 software was used for acquisition and calculating Pearson's correlation.

ELISA

The supernatants from infected and uninfected cells were collected and snap frozen. ELISA was performed to gauge the levels of IL-6 and IL-8 using DUOSet ELISA kits from R&D Biosystems for human IL-6 and IL-8 respectively, following the manufacturer's protocol.

Drosophila melanogaster Experiments: DR, Rapamycin Treatment and dilp2-3,5

DR in Drosophila melanogaster was performed by feeding a total of 50 hatched flies with 0.5× SYA food compared to ad libitum food supply of 2× SYA for 10 days. Rapamycin treatment was performed by dissolving Rapamycin in absolute ethanol and mixing it with SYA food at a final concentration of 200 µM and fed to a total of 50 age-matched flies. For control food, ethanol alone was added. Both DR and Rapamycin treatment were performed for 10 days before harvesting the flies for experiments. The treatments were performed separately in 3 different vials serving as 3 independent biological replicates. Long-lived dilp2-3,5 and control wDah flies were harvested on day 1 of adulthood. The flies were dissected and immunofluorescence was performed on the dissected tissues as described above.

DR and IRS1 KO Mice

The mice used for the experiments were handled according to the guidelines of LANUV (Landesamt fur Natur, Umwelt and Verbraucherschutz Nordrhein-Westfalen, Germany). C57BL/6 male mice were maintained under 12-hour light:12 hour dark schedule and were fed standard chow diet (SC)—4.5 g SC/animal/24 hours (ssniff® Spezialdiäten GmbH) until 10 weeks of age and then subjected to DR at 75% food intake (3 g SC per animal/24 hours) compared to ad libitum fed control mice. The DR regimen was continued for 1 month and the mice were sacrificed at the age of 14 weeks along with the ad libitum fed controls to perform cryosectioning for the analysis of nucleoli. The tissues sampled with sectioning were kidney and liver.

C57BL/6 IRS1 KO male and WT control male mice were maintained similarly on SC diet. The animals were sacrificed at the age of 12 months to perform cryo-sectioning for the analysis of nucleoli. The tissues sampled with sectioning were kidney and brain.

For both the experiments cryo-sectioning was performed horizontally across the entire tissue. This nature of processing aided in observing the effect of the treatments across different cell types in each tissue.

Dietary Restriction (DR) and Exercise Intervention in Human Volunteers

Samples for nucleolar staining were obtained from the biomaterial collected in the Growing Old Together Study, a 13-weeks lifestyle intervention in older adults, consisting of 12.5% caloric restriction and 12.5% increase in physical activity, resulting in an average weight loss of 3.3 kg. The study design, inclusion and exclusion criteria, and changes in metabolic parameters have been described in van de Rest, O. et al.; $Aging$ (Albany N.Y.) 8, 111-26 (2016). For the current study samples from 5 men and 5 women were used and selected based on the greatest weight loss due to the intervention and the availability of muscle tissue from before and after the lifestyle intervention. This subgroup had an average age of 62.4 years (±4.1) and lost an average of 6.8 kg (±1.3) due to the intervention. All participants signed a written informed consent for participating in this study. All experiments were performed in accordance with the relevant regulations and guidelines. The medical ethical committee of the Leiden University Medical Center approved this study. This trial (NTR3499) was registered at the Dutch Trial Register (www.trialregister.nl).

Muscle Biopsies and Sectioning

Muscle biopsies were collected from the vastus lateralis muscle before and after the lifestyle intervention. Biopsies were collected 40-45 minutes following a standardized liquid meal (Nutridrink™, Nutricia Advanced Medical Nutricion, Zoetermeer, The Netherlands) in the morning after at least 10 hours of fasting. Under local anesthesia, an incision was made 10 cm cranial of the patella on the lateral side of the upper leg. A biopsy needle (3 mm thick) was inserted to obtain the muscle biopsy. The muscle biopsy was immediately frozen in liquid nitrogen and stored at −80° C. prior to cryosectioning. Cryosections of 16 μm were made with the CM3050-S cryostat (Leica, Wetzlar, Germany), pasted on SuperFrost Plus slides (Menzel-Glaser, Braunschweig, Germany) and stored at −20° C. prior to staining.

Blinding of Experiments

All the lifespan analysis experiments were performed in a blinded manner. For blinding, the strain names were concealed during scoring, analyzing and plotting the data. Nucleolar imaging and quantification were also performed with concealed strain names.

Drosophila nucleolar size analysis was performed in a blinded manner. Two different people were involved in performing the experiment. One individual carried out fly feeding and mutant strain maintenance and the samples were passed on blinded for imaging and quantification to the second experimenter.

Mouse nucleolar size analysis was also carried out blinded. Three different people were involved in performing the experiments. One experimenter maintained the mice while carrying out the feeding/treatments and sacrificed the mice for sectioning. The experiment was blinded henceforth. The sectioning was carried out blinded by the second experimenter. The blinded sections were stained, imaged and quantified by the third experimenter.

Two different experimenters performed human muscle biopsy staining. The whole experiment including staining, imaging and image quantification were performed completely blinded.

Example 1: ncl-1 Mediates DR Induced Lifespan

Figure 1:
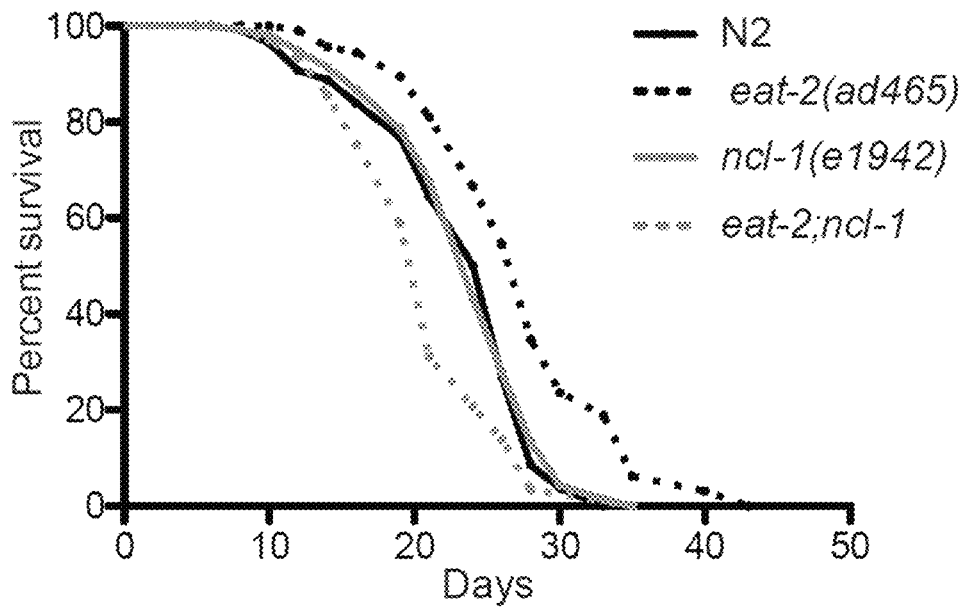
FIG. 1: shows that ncl-1 mediates DR and other forms of lifespan.
 (a) Lifespan of eat-2(ad465) is abolished with the loss of ncl-1(e1942) (P<0.0001). (b) ncl-1(e1942) is significantly shorter lived than N2 upon bacterial dilution across 7 different concentrations (P<0.0001). (c,d) ncl-1(e1942) is shorter lived than N2 upon let-363/TOR and daf-2 RNAi (P<0.0001). (e,f) glp-1(e2141) and isp-1(qm150) are significantly longer lived than glp-1;ncl-1 (P<0.0001) and isp-1;ncl-1 (P=0.0016) respectively. (g) Over-expression of ncl-1(+) in N2 for two independent extrachromosomal transgenic arrays (dhEx1007, dhEx1008) increases lifespan (P<0.0001). P-values calculated by log-rank test.
Figure 1:
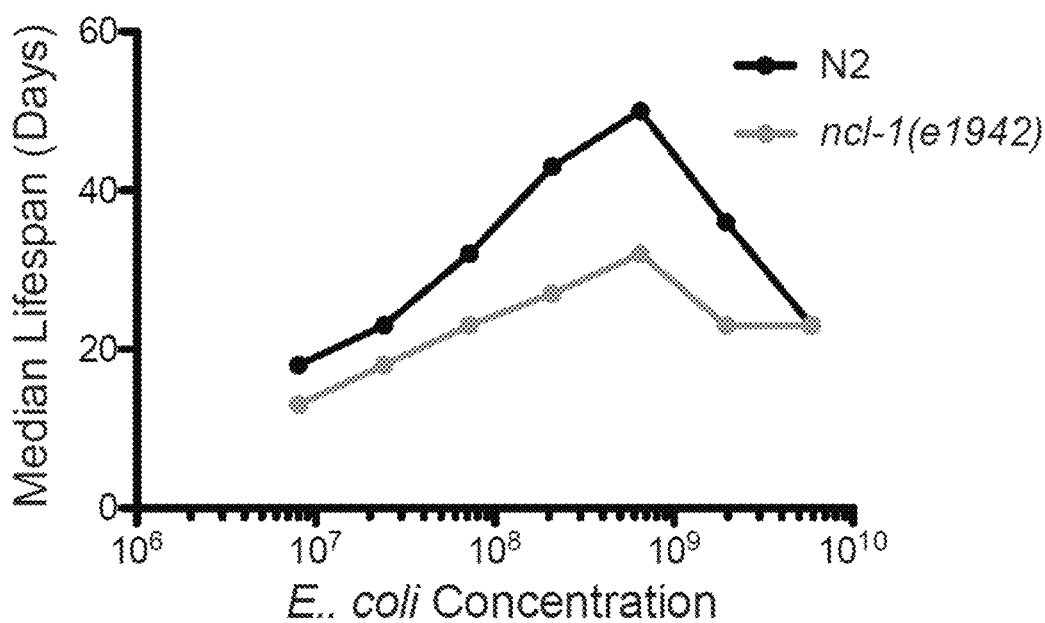
Figure 1:
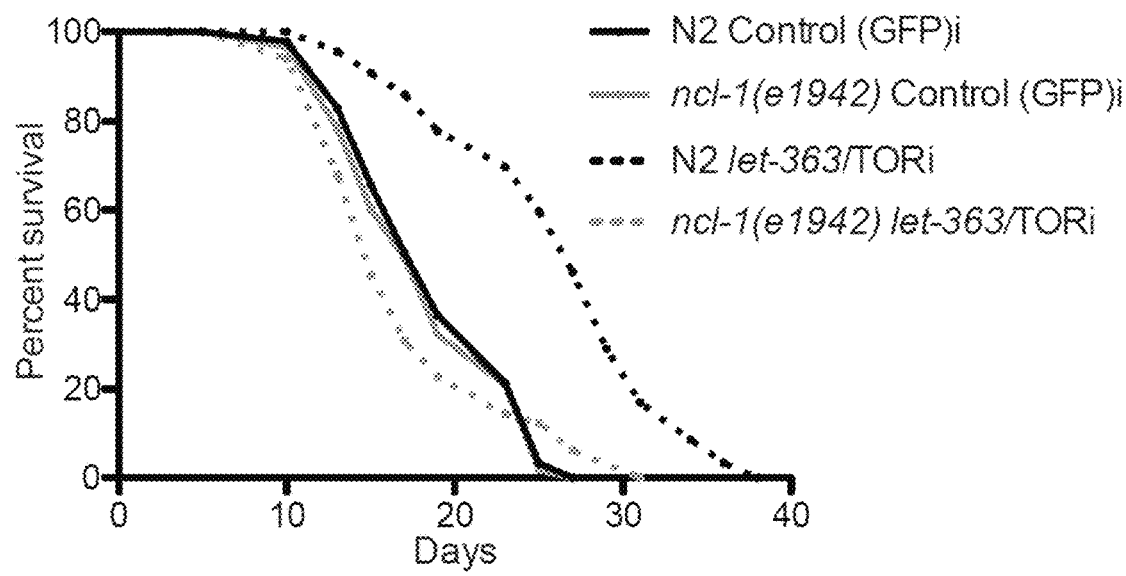
Figure 1:
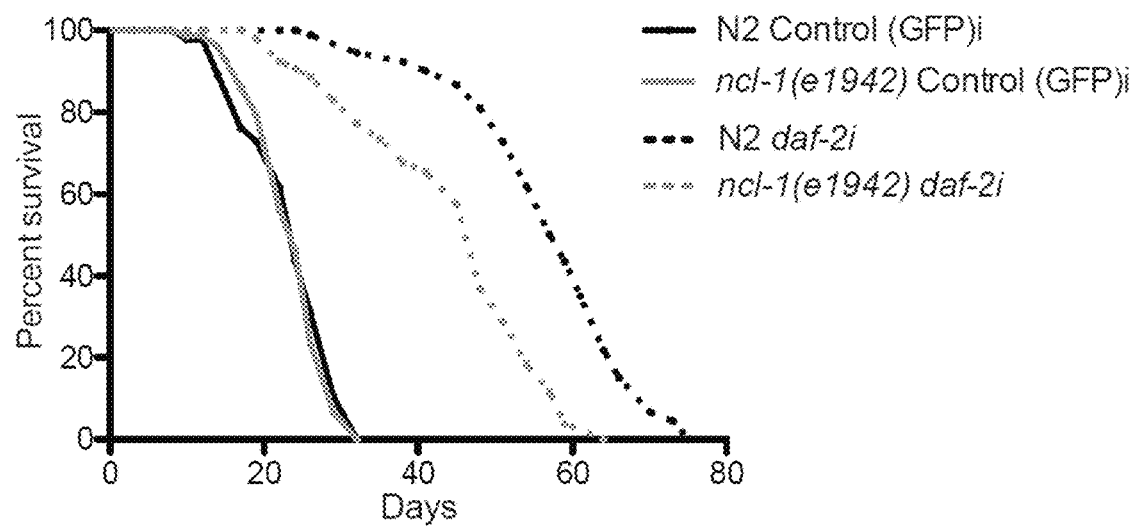
Figure 1:
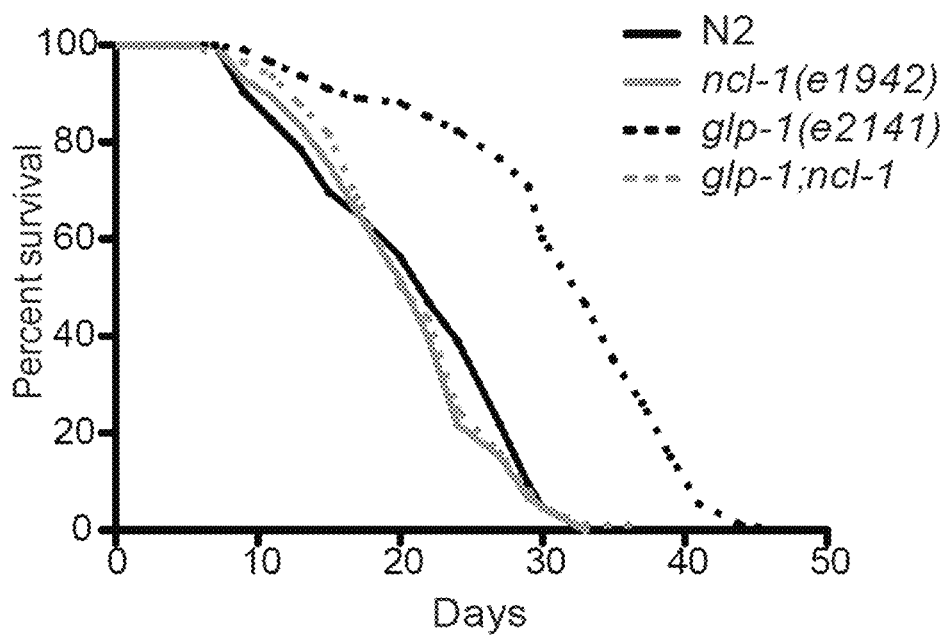
Figure 1:
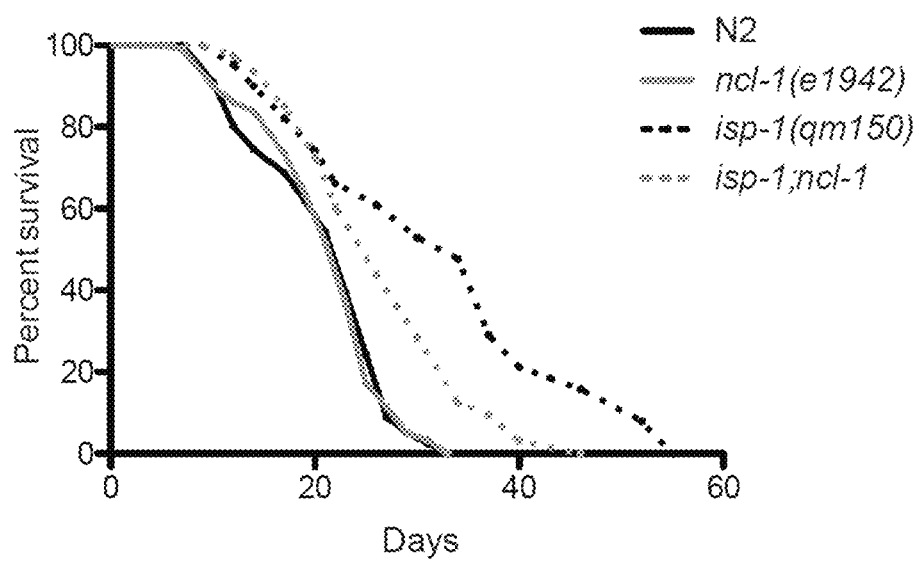
Figure 1:
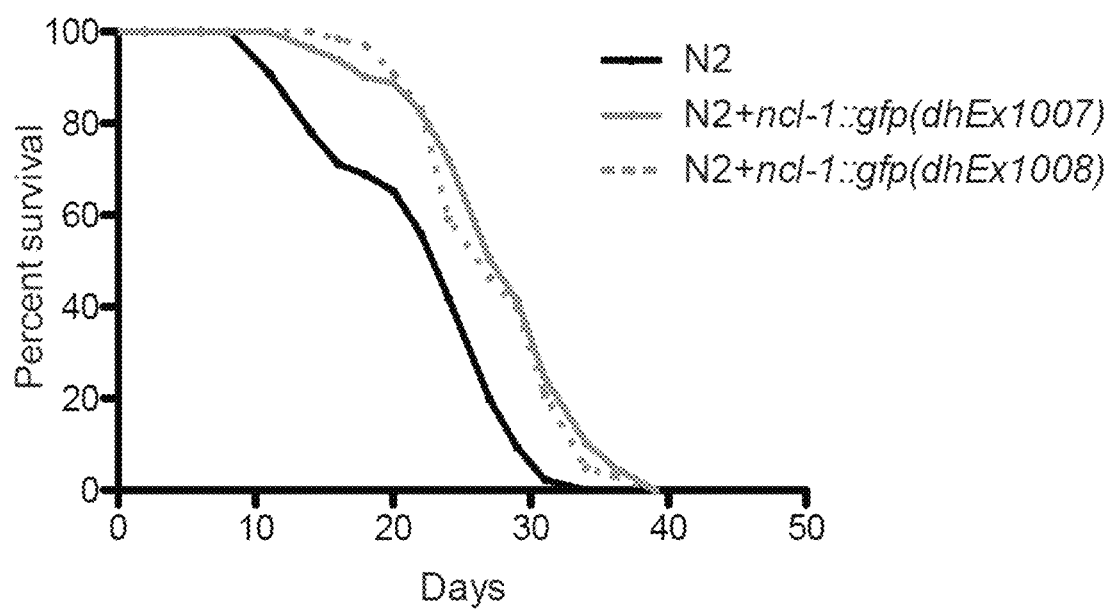
Figure 1:
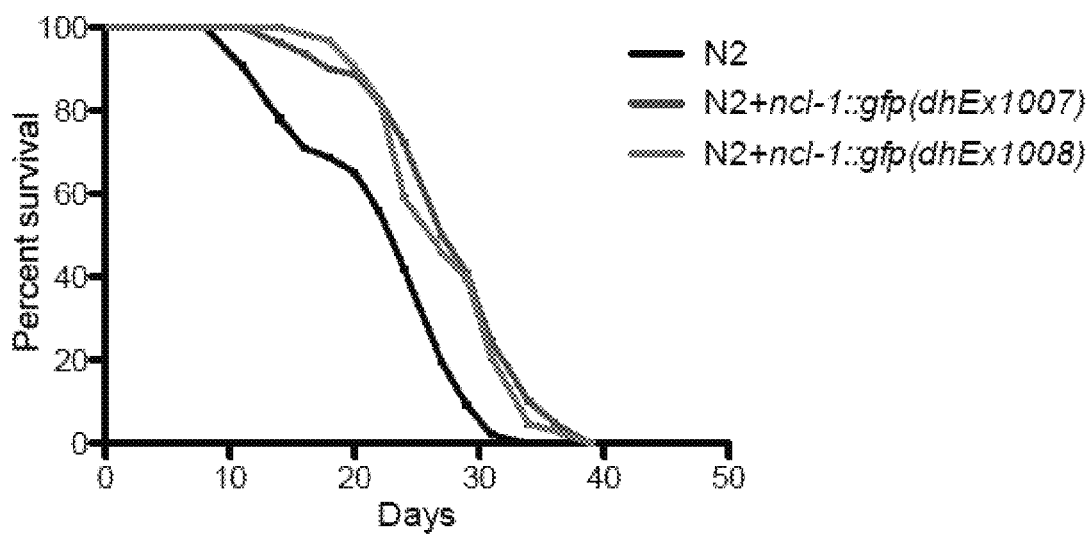

The inventors identified the conserved B-box protein NCL-1 in genetic screens for novel mediators of dietary restriction (DR) induced lifespan. NCL-1 is an ortholog of the TRIM2/BRAT tumor suppressor, which inhibits rRNA and 5S RNA transcription and protein synthesis. Consistent with a role in ribosome biogenesis, NCL-1 regulates nucleolar size and ncl-1 mutants have larger nucleoli especially in neuronal, muscle and hypodermal cells. It could be shown that whereas ncl-1 loss had little effect on wildtype lifespan, it potently suppressed the lifespan of eat-2 mutants, a genetic model of DR (FIG. 1a). ncl-1 mutation also abrogated lifespan across a wide range of bacterial food dilutions, revealing a function in the nutrient response to dietary restriction (FIG. 1b).

Example 2: ncl-1 Mediates Other Forms of Lifespan

The inventors next asked if ncl-1 also modulates lifespan in other known lifespan models. Reduced TOR signaling is partly responsible for lifespan extension under DR conditions. Accordingly, ncl-1 mutation abrogated lifespan induced by let-363/TOR RNAi knockdown (FIG. 1c), suggesting that ncl-1 mediates lifespan extension upon TOR down-regulation. Reduced insulin/IGF signaling potently promotes lifespan across taxa, and knockdown of daf-2, the C. elegans insulin/IGF receptor, doubles the lifespan; ncl-1 mutation partially suppressed daf-2 lifespan as well (FIG. 1d). Furthermore, ncl-1 loss abolished lifespan extension in long-lived germlineless glp-1 mutants (FIG. 1e) and partially suppressed lifespan triggered by mutation of the iron sulfur protein isp-1, which reduces mitochondrial function (FIG. 1f). A modest reduction in translation is known to extend lifespan in different organisms. C. elegans harboring loss-of-function mutations in ife-2 or ifg-1, which encode translation initiation factors, have reduced translation and extended lifespan. Similarly, rsks-1 codes for the ribosomal protein S6 kinase (S6K), which is a known downstream target of the TOR kinase whose deficiency reduces protein synthesis and extends lifespan in multiple species. Loss of ncl-1 by RNAi largely abolished the longevity phenotype of ifg-1, ife-2, and rsks-1 mutant worms (FIG. 1g). Altogether these findings reveal that ncl-1 works in major lifespan pathways to affect lifespan, as part of a convergent mechanism.

Example 3: Further Investigation of the Role of ncl-1

Therefore, extra-chromosomal transgenic lines expressing wildtype ncl-1 fused to gfp were generated. Arrays restored normal nucleolar size and extended lifespan in eat-2;ncl-1 double mutants, demonstrating that the transgene is functional. The fusion protein was found to reside in multiple tissues including neurons, body wall muscle, pharynx, seam cells and vulva. Consistent with an instructive role, ncl-1 over-expression in the wildtype background was sufficient to reduce nucleolar size and increase lifespan (FIG. 1h). No further increase of lifespan of eat-2 upon ncl-1 over-expression was seen, indicating an overlapping mechanism.

Example 4: Investigation of Nucleolar Size in Long-Lived Genotypes

Figure 2:
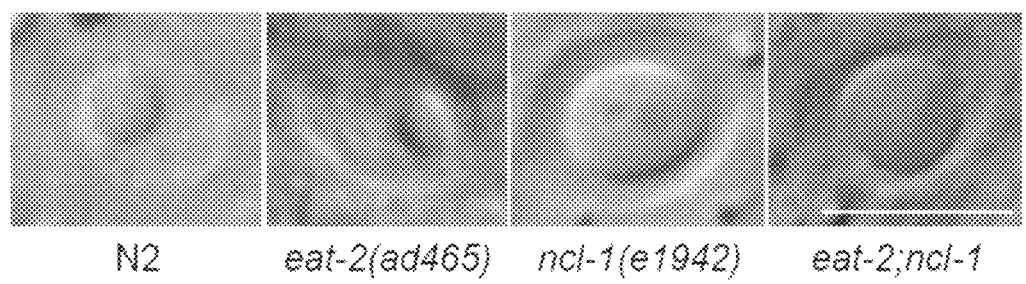
FIG. 2: shows that the nucleolar size inversely correlates with lifespan.
Figure 2:
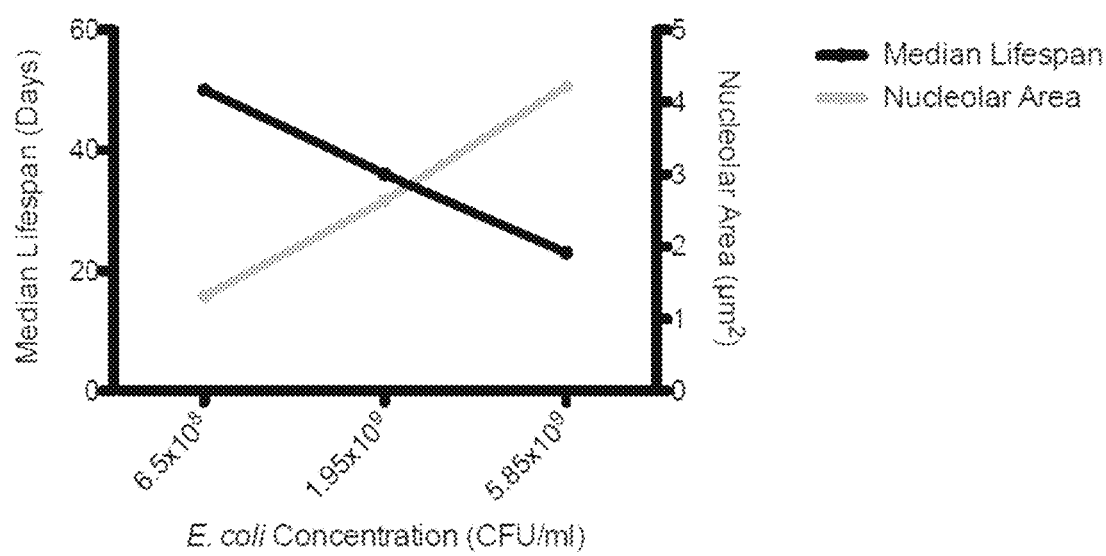
Figure 2:
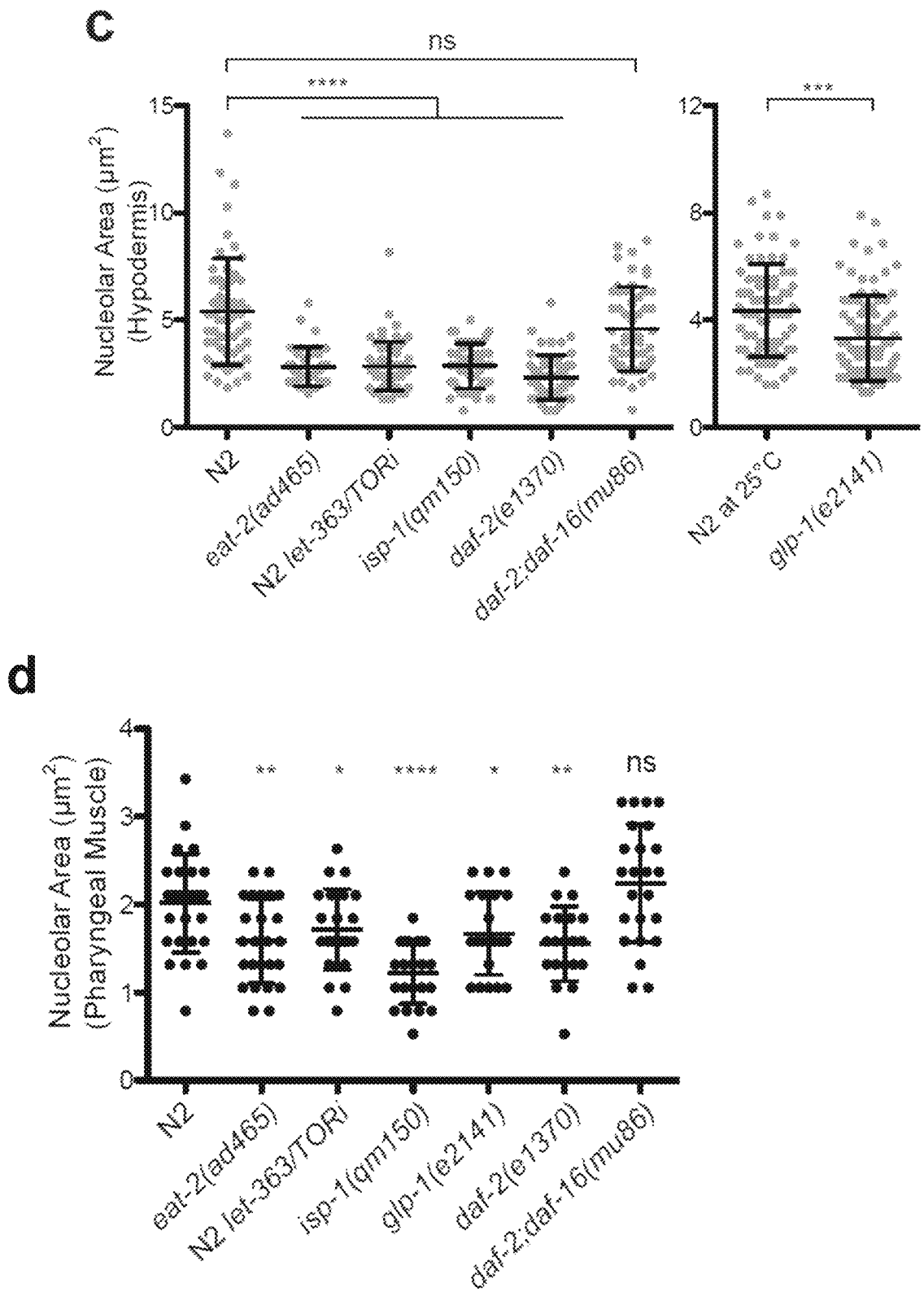
Figure 2:
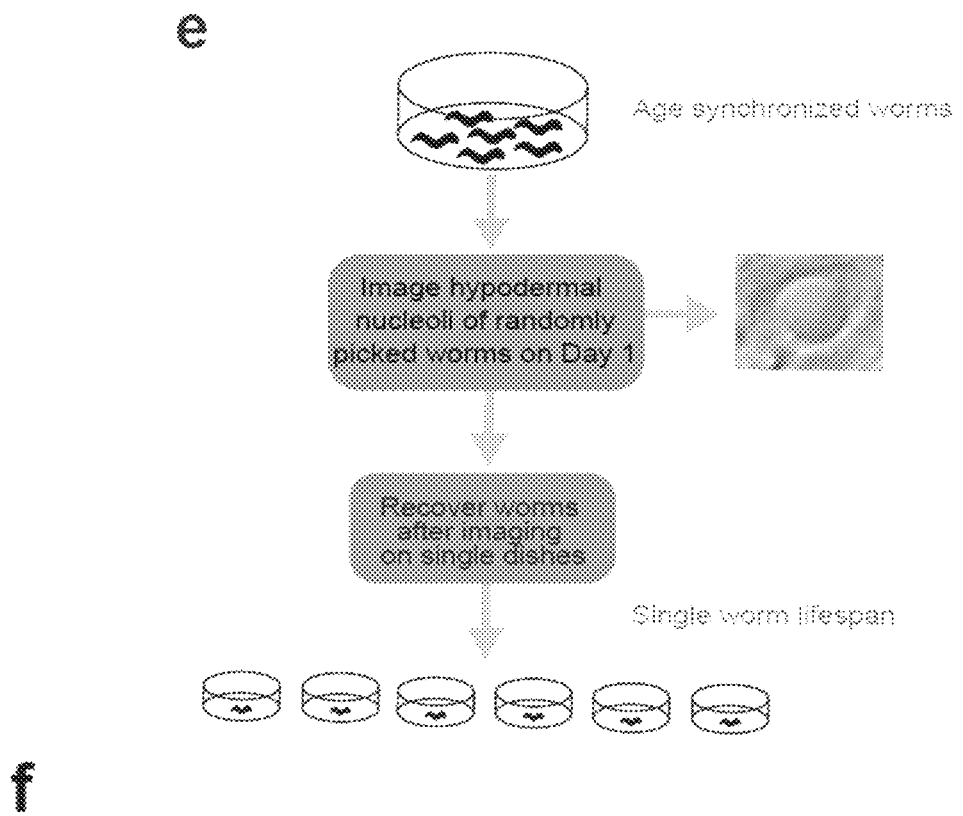
Figure 2:
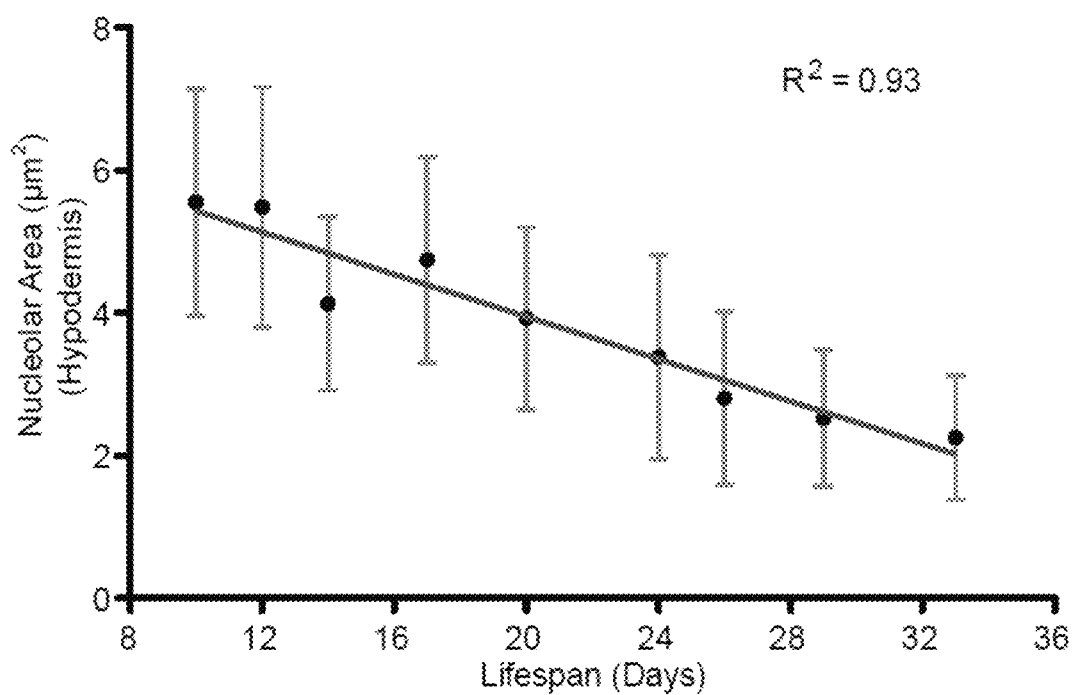

Since ncl-1 affects both lifespan and nucleolar size, the inventors wondered if nucleolar size also changes in long-lived genotypes. To address this issue, the nucleolar size of superficial hypodermal cells was measured on the first day of adulthood. As previously shown, ncl-1 mutants had enlarged nucleoli compared to wildtype (FIG. 2a). It could further be observed that eat-2 mutants had smaller nucleoli (FIG. 2a,c), and accordingly found that reducing nutrient levels through bacterial dilution diminished nucleolar size (FIG. 2b). Nucleolar size was enlarged in eat-2;ncl-1 double mutants, revealing that ncl-1 is epistatic to eat-2 for both nucleolar size and lifespan (FIG. 2a). These intriguing observations led us to ask whether other lifespan pathways more generally affect nucleolar size. Surprisingly, reduced insulin/IGF signaling (daf-2), reduced mTOR (let-363), reduced mitochondrial function (isp-1), reduced translation (rsks-1, ife-2, ifg-1) and germlineless animals (glp-1) all displayed smaller nucleoli in several tissues (FIG. 2c,d). ncl-1 mutation variously suppressed nucleolar size in these backgrounds. The FOXO homolog daf-16, which promotes daf-2 lifespan, was also required for small nucleolar size of daf-2 mutants, supporting the notion that these signaling pathways impinge on the nucleolus to regulate lifespan (FIG. 2c,d).

Isogenic wildtype worms show considerable variance in life expectancy, with some animals dying as early as day 10 and others as late as day 30, despite culture in a uniform environment. The basis of this variance however has remained elusive. It could be shown that wildtype animals showed variance in nucleolar size. To address this question if these differences associate with lifespan in wildtype populations, the inventors imaged the nucleoli of age-matched worms on the first day of adulthood, recovered them on single plates and monitored their lifespan individually (FIG. 2e). A striking inverse correlation (Pearson correlation coefficient, 0.61-0.93) between nucleolar size and lifespan was found, where animals with smaller nucleoli lived considerably longer than the ones with larger nucleoli (FIG. 2f). Thus, nucleolar size could be a source of variance in lifespan and may predict C. elegans life expectancy.

Example 5: Examination of Nucleolar Functions Affected by ncl-1

To unravel molecular mechanisms, the inventors examined how ncl-1 and various lifespan mutants affected nucleolar functions. Loss of ncl-1 has been previously shown to up-regulate the nucleolar protein FIB-1/fibrillarin, which serves as a methyltransferase for pre-rRNA processing and modification, and regulates rRNA transcription and histone modification. In accord with this, it was possible to observe increased levels of FIB-1::GFP as well as endogenous FIB-1 in ncl-1 mutants (FIG. 3a,c). Conversely ncl-1 over-expression down-regulated FIB-1. The inventors next asked if FIB-1 expression was affected in various lifespan mutants. Indeed both FIB-1::GFP and endogenous FIB-1 were significantly reduced in eat-2, daf-2, glp-1, isp-1 and upon TOR knockdown and loss of ncl-1 reversed this effect (FIG. 3a,c,d), revealing that these pathways converge on FIB-1 expression. It was further evaluated if FIB-1 is a passive marker or a causal factor for lifespan. Consistent with the latter, fib-1 RNAi knockdown reduced nucleolar size and extended lifespan of wildtype worms (FIG. 3e,f). RNAi knockdown of another gene involved in nucleolar function, rrn-3, which encodes TIF1A that assists in rRNA transcription mediated by RNA Polymerase I, had little observable effect on longevity, perhaps because achieving a balance where benefits outweigh deleterious effects is difficult.

Nucleoli are the cellular site of ribosome biogenesis. Therefore the expression levels of rRNA and ribosomal proteins were examined. Mutation of ncl-1 increased rRNA and ribosomal protein levels (FIG. 3b,c). These molecules were also reduced in worms over-expressing ncl-1. Notably long-lived eat-2, daf-2, glp-1, isp-1 and TOR RNAi knockdown worms exhibited reduced levels of rRNA and ribosomal proteins RPS6 and RPS15, suggesting down-regulated ribosome biogenesis associates with lifespan (FIG. 3b,c). Loss of ncl-1 variously suppressed these phenotypes in double mutant backgrounds (FIG. 3b,c). Similarly, daf-16 mutation restored the reduced rRNA and ribosomal proteins levels seen in daf-2 mutants back to wildtype levels (FIG. 3b). Taken together, these results suggest that smaller nucleoli, reduced fibrillarin and ribosome biogenesis, are signatures of long life.

Example 6: Investigation of Nucleoli Size in Higher Organisms

Given the results in C. elegans, the inventors wondered if these findings hold true in long-lived models in other species. Remarkably it could be shown that long-lived Drosophila melanogaster undergoing DR, exposed to the mTOR inhibitor rapamycin, or harboring deletion of the insulinlike peptides ilp-2-3,5, all had smaller nucleoli in the fat body and intestine (FIG. 4a,b). Furthermore, they showed reduced levels of fibrillarin and ribosomal proteins, although RPS6 and RPS15 levels did not significantly change upon Rapamycin treatment in flies unlike worms.

Age-matched mice undergoing DR and long-lived IRS1 knockout mice also exhibited smaller nucleoli in kidney, liver and whole brain sections compared to controls (FIG. 4c,d). Finally, an overall trend towards reduction of nucleolar size in muscle biopsies of elderly human volunteers who underwent a regime reducing caloric intake by 12.5% combined with moderate increase in exercise by 12.5% (FIG. 4e,f) could be observed.

Example 7: Examination of Nucleolar Functions Affected by fib-1/Fibrillarin

The present invention discloses a novel role of the nucleolus and more specifically the nucleolar methytransferase Fibrillarin in response to infection against different pathogenic bacteria. Infection in C. elegans with Staphylococcus aureus and Enterococcus faecalis leads to a reduction in nucleolar size. ncl-1/TRIM2 mutants that are known to possess enlarged nucleoli are refractory to infection mediated reduction in nucleolar size and are thereby more sensitive to infection suggesting that a reduction in nucleolar size might be a protective innate immune response towards infection (FIG. 5). Interestingly, human macrophages often display a similar response towards infection; their nucleolar size modestly shrinks after bacterial infection suggesting that the effects on the nucleolus are conserved across evolution and may represent a specialized defense response towards infection (FIG. 5).

At the molecular level, it was observed nucleolar methyltransferase Fibrillarin, which plays a crucial role in the maturation of ribosomal RNA (rRNA), is involved in regulating infection resistance. Similar to nucleolar size, Fibrillarin levels drop after infection in C. elegans. These effects are also conserved across taxa. Fibrillarin levels are reduced in human HeLa cells and murine bone marrow macrophages after infection. Interestingly a reduction in Fibrillarin levels via RNAi prior to infection primes the host for a stronger response against infection ultimately leading to a significantly increased survival. Furthermore, a reduction in Fibrillarin prior to infection leads to enhanced bacterial clearance within cells presumably due to enhanced phagocytosis since Fibrillarin knockdown augments the apposition of the intracellular bacteria to lysosomes and increases expression of lysosomal markersLAMP1 and Cathepsin. Finally fibrillarin treatment results in lower levels of inflammatory cytokines but increased levels of anti-inflammatory cytokines. These data provide strong evidence of the conserved role of the nucleolus and nucleolar resident protein Fibrillarin in response to infection (FIG. 6) Fibrillarin reduction mediated immune protection represents a novel mechanism against infection. Fibrillarin functions independently of the well-known C. elegans' pathways that are activated upon infection. daf-16/FOXO, pmk-1/p38 MAP kinase and hlh-30/TFEB are major factors known to mediate immunity in worms and mutations in these genes render worms susceptible to infection. However, Fibrillarin knockdown in these mutants increases resistance and overcomes their susceptibility to infection suggesting that Fibrillarin mediated regulation represents a novel conserved immune mechanism.

Cellular organelles such as the mitochondria and the endoplasmic reticulum have been shown to have important roles in regulating innate immune responses. The present invention discloses a novel role of the nucleolus in the infection response. Fibrillarin is one such factor which could potentially serve as a drug target.

Results fib-1/Fibrillarin Regulates Bacterial Infection Resistance in C. elegans.

C. elegans fib-1 encodes the highly conserved nucleolar methyltransferase Fibrillarin, which is a vital factor in the C/D small nucleolar ribo-nucleoprotein (snoRNP) complex. Fibrillarin mediates 2'-O-ribose methylation of ribosomal RNA (rRNA) thereby assisting in the maturation of rRNA, and also methylates histone H2AGIn105 at the rDNA locus. fib-1 is down-regulated in multiple well-established longevity mutants of C. elegans and that fib-1 knockdown reduces nucleolar size and extends lifespan in worms. Since genes that promote lifespan extension often induce tolerance against multiple stress conditions including pathogenic infections, the inventors wondered if fib-1 reduction could confer infection resistance against pathogens. The inventors knocked-down fib-1 using RNAi and monitored infection resistance in worms. Since fib-1 is an essential gene, the inventors resorted to RNAi from larval stage 3 (L3) up to day one of adulthood (around 30 hours of fib-1 RNAi), which led to a significant reduction in FIB-1 levels without causing any developmental defects (FIG. 12A). Interestingly, animals with fib-1 RNAi displayed significantly increased survival upon infection with pathogens S. aureus, E. faecalis and P. aeruginosa (FIG. 7A,B and FIG. 12B). fib-1 knockdown did not affect other stress responses including heat, cold and oxidative stress resistance, suggesting that fib-1 specifically regulates pathogen resistance (FIG. 12C, D,E). fib-1 RNAi did not affect pharyngeal pumping rate, ruling out the possibility of differences in bacterial intake (FIG. 12F). the inventors have shown previously the B-box protein NCL-1/TRIM2 to be an upstream negative regulator of FIB-1. FIB-1 levels are highly upregulated in ncl-1 loss-of-function mutants. Therefore, the inventors tested the survival of ncl-1 mutants upon infection. Interestingly, the inventors found ncl-1 mutants were more susceptible to infection, suggesting that increased levels of fib-1 are detrimental for survival upon infection challenge (FIG. 7C,D). Heat killed bacteria did not lead to infection and early mortality, attributing the early mortality to pathogenic infection caused by live bacteria (FIG. 12G). Taken together, our results reveal a state of protection conferred by fib-1 reduction that helps worms survive longer upon infection.

FIB-1/Fibrillarin and nucleolar size are reduced upon bacterial infection

Next, the inventors assessed the levels of FIB-1 after infection. the inventors performed western blot to detect the endogenous levels of FIB-1 after 12-hour infection in wildtype and more susceptible ncl-1 mutants. The inventors observed a down-regulation of FIB-1 protein levels in wildtype worms after infection with S. aureus, E. faecalis and P. aeruginosa (FIG. 8A,B, FIG. 13A).

ncl-1 mutants also exhibited a slight reduction of FIB-1 after infection but the levels remained significantly higher compared to wildtype (FIG. 8A,B). The inventors also obtained similar results with the FIB-1::GFP strain harboring a translational fusion; the GFP signal was significantly down-regulated after infection with S. aureus (FIG. 8C). Notably, the inventors did not observe significant transcriptional changes of fib-1 using qPCR, suggesting a posttranscriptional response (FIG. 13B). In our previous study, the inventors reported that the nucleolar size decreased in worms subjected to fib-1 RNAi. Because the inventors observed a reduction in FIB-1 levels after infection, the inventors wondered if nucleolar size changes correspondingly. Indeed the inventors observed a significant decrease (~25%) in the nucleolar size of worms after 12-hour infection with S. aureus and E. faecalis (FIG. 8D,E). The size of nucleoli did not change when worms were fed heat-killed S. aureus and E. faecalis, suggesting that nucleolar reduction was caused by active infection (FIG. 13C,D). ncl-1(+) is known to limit nucleolar size in worms; ncl-1 null mutants possess enlarged nucleoli in multiple tissues. The inventors assessed the nucleolar size of ncl-1 mutants after infection and observed that unlike wildtype worms, nucleolar size remained enlarged (FIG. 8D,E). Taken together, these results suggest that a reduction in FIB-1 levels and nucleolar size might be a host-response towards combating infection challenge. ncl-1 mutants are somewhat refractory in this response, which might explain their increased susceptibility.

fib-1/Fibrillarin reduction improves resistance of infection sensitive mutants

The inventors next sought to investigate the link between fib-1 and established major defense-response pathways in C. elegans. The inventors examined genetic epistasis between fib-1 and known vital mediators of defense-response upon pathogenic insult in worms. p38 MAP Kinase (MAPK) pathway is a key evolutionarily conserved defense-response pathway that is activated upon microbial infection and mediates important downstream transcriptional changes. p38 MAPK, which is encoded by pmk-1 in C. elegans, is the major regulator of this pathway. A mutation in pmk-1, leads to increased susceptibility of worms upon infection with diverse pathogens. fib-1 knockdown significantly improved the survival of pmk-1 (FIG. 9A, FIG. 14A). Next the inventors tested hlh-30/TFEB which is a crucial factor promoting autophagy and antimicrobial gene expression as part of the host-response upon infection in worms and mammals. Previous reports have shown that HLH-30/TFEB is nuclear localized upon bacterial infection and is required for mediating infection resistance in C. elegans. However, fib-1 knockdown did not affect HLH-30 nuclear localization (FIG. 15A,B). Interestingly, knocking-down fib-1 in hlh-30 mutants also led to a significant increase in survival of these animals upon infection (FIG. 9B, FIG. 14A). These findings suggest that the protective effects imparted by fib-1 reduction function independently of HLH-30/TFEB. Finally the inventors examined the epistasis with daf-16/FOXO, another important highly conserved transcription factor driving anti-microbial genes and infection resistance of daf-2 mutants. Similar to the effects on pmk-1 and hlh-30, daf-16 showed increased survival on infection upon fib-1 RNAi (FIG. 9C, FIG. 14A). Furthermore, reduced survival of ncl-1 mutants was also rescued with fib-1 RNAi (FIG. 9D, FIG. 14B,C). Taken together, our results reveal FIB-1 as a novel regulator of host-response towards infection working downstream or independently of established defense-response pathways in worms.

fib-1/Fibrillarin reduction induces translation suppression reporter irg-1

To investigate the mechanism behind fib-1 reduction mediated pathogen resistance, the inventors studied the involvement of mRNA translation. Recent studies have reported that worms detect translation suppression by infection as a means to activate defense response. Since FIB-1 is a methyltransferase involved in rRNA maturation and ribosome biogenesis, the inventors hypothesized that fib-1 RNAi might lead to a reduction in ribosome biogenesis and thereby translation, thus activating the defense response. To test this possibility, the inventors examined a well-established reporter gene, irg-1 (infection response gene-1) fused to GFP. irg-1 is activated by the bZIP transcription factor ZIP-2 during pathogen challenge. In response to a block in translation upon infection with *P. aeruginosa*, ZIP-2 itself is preferentially translated in a manner dependent upon its upstream 5' UTR. After infection with *S. aureus*, the inventors observed a strong induction of irg-1 (FIG. 10A,B). Interestingly, the inventors observed a similar induction of irg-1 transgene as well as the irg-1 transcript upon fib-1 knockdown without infection, suggesting that fib-1 RNAi might reduce translation and thereby activate irg-1 (FIG. 10C,D,E). As a control, the translational inhibitor cycloheximide also induced irg-1 in a similar manner (FIG. 16A). This was not a generalized inflammatory response, however, as other major infection related genes did not change upon fib-1 RNAi (FIG. 16B). The inventors next sought to test if fib-1 mediated protection is mediated by a reduction in translation. To address this question, the inventors first asked if mutants with reduced translation have improved infection resistance. The inventors used ifg-1 and ife-2 mutants, which are known to have reduced translation. ifg-1 encodes the translation initiation factor eI4F/G, while ife-2 encodes the cap binding initiation factor eIF4E. Indeed ifg-1 and ife-2 strains were significantly resistant to infection (FIG. 10F, FIG. 16C). Moreover, fib-1 RNAi only marginally enhanced the survival of ifg-1 mutants upon infection (FIG. 10G,H).

These results collectively suggest that fib-1 knockdown mediated pathogen resistance mechanistically overlaps with infection resistance conferred by translational reduction.

Fibrillarin reduction protects mammalian cells against bacterial pathogens

The inventors next sought to understand the potential role of Fibrillarin in imparting immunity against infections in mammalian systems. To begin with, it is wondered if mammalian Fibrillarin levels are also perturbed after infection, as observed in *C. elegans*. It is found that HeLa cells infected with *S. aureus* exhibited significantly reduced levels of Fibrillarin at varying multiplicities of infections (MOI) (FIG. 11A). Similarly mouse bone marrow derived macrophages infected with *S. aureus*, *E. faecalis*, *S. typhimurium* and *L. monocytogenes* showed reduced levels Fibrillarin after 24 hours of infection (FIGS. 11 B,C). Moreover the inventors also observed a reduction in nucleolar size in THP1 cells 24 hour post-infection with *S. aureus* similar to our results in worms, indicating that nucleolar size reduction is a conserved hostresponse to infection (FIGS. 11 D,E).

The inventors next wondered whether Fibrillarin reduction post-infection in mammalian systems is protective. The inventors reasoned that if Fibrillarin was reduced before infection, it could prime a host response to incoming pathogens. The inventors used HeLa cells, a widely used model system to study *S. aureus* infections$_{38-41}$. A major feature of *S. aureus* infection is the ability of the pathogen to induce inflammation and host cell death, a phenomenon attributed to the pathogenicity of the bacteria. The inventors performed siRNA mediated silencing of Fibrillarin 48 hours before infection (FIG. 17A) and compared the percentage of cells surviving at 6 and 24 hours post-infection in both Fibrillarin and control siRNA treated cells. Fibrillarin knockdown cells displayed significantly better survival after infection with *S. aureus* compared to control siRNA treated cells as assayed by trypan blue staining (FIG. 11F) and lactate dehydrogenase (LDH) cytotoxicity assay (FIG. 17B). Conversely, Fibrillarin over-expression modestly enhanced the susceptibility of HeLa cells to infection (FIG. 17C). Fibrillarin knockdown and overexpression did not influence bacterial uptake by cells as measured by comparing intracellular colony forming units (CFU) with respective controls (FIG. 17D,E). Furthermore Fibrillarin knockdown prior to infection led to a reduction of pro-inflammatory cytokines IL-6 and IL-8, indicating reduced inflammation (FIG. 11G). Immunofluorescence using GFP labelled *S. aureus* showed increased apposition of the intracellular bacteria to lysosomes in cells treated with Fibrillarin siRNA compared to control siRNA (FIG. 11H,I), which might explain increased cell survival. Taken together, these results point towards a conserved mechanism of bacterial infection resistance possibly imparted by increased phagosome maturation and reduced inflammation that is mediated by Fibrillarin knockdown in mammalian cells.

Discussion

Perturbation of biological systems by infection leads to a multilayer complex cellular and organismal response. Whether this response ultimately leads to clearance of infection or collapse of the host system is largely dependent on the extent and nature of the cellular pathways perturbed and the interplay between host and pathogen.

Cellular organelles such as mitochondria, ER, and lysosome have long been identified as signaling hubs that help manage infection. However, a role for the nucleolus in mediating the innate response to pathogenic stress is relatively unstudied. In this work, the inventors identified the nucleolar protein Fibrillarin as a novel player in regulating bacterial pathogen resistance of *C. elegans*. Fibrillarin reduction increases the survival of worms challenged with *S. aureus*, *E. faecalis*, and *P. aeruginosa* infection and conversely ncl-1/TRIM2 mutants that possess higher levels of Fibrillarin are more susceptible to infection. Since *C. elegans* is largely dependent on innate immune signaling for pathogen resistance, the results indicate that higher levels of Fibrillarin suppress innate immunity against bacterial pathogens. Interestingly, active bacterial infection and not heat-killed bacteria lead to a reduction in nucleolar size. This indicates that a reduction in nucleolar size and a decrease in Fibrillarin levels constitute a host response mounted against active bacterial infection. *C. elegans* pathogen defense pathways are activated by a number of important factors including PMK-1/p38 MAPK, HLH-30/TFEB and DAF-16/FOXO. However, it still remains unclear how these different molecules coordinate downstream mechanisms to confer pathogen resistance. The present invention demonstrates that Fibrillarin regulates infection resistance as a convergent factor genetically downstream or parallel to these major players.

Pathogens often disrupt core cellular processes by delivering toxins so as to disable essential processes and pathways that would otherwise help mount a defense response. Multiple studies have reported that disruption of major cellular processes including mitochondrial respiration, proteasomal activity, microtubular dynamics and mitochondrial UPR can provoke immune-responsive genes, corroborating the notion of effector-triggered immunity. The present invention shows that translation inhibition imparts pathogen resistance possibly working in the realm of effector-triggered immunity. It is further shown that perturbation of nucleolar function by Fibrillarin knockdown promotes immunity against bacterial infection.

The present invention thus demonstrates a novel connection between the nucleolus and anti-bacterial immune function. Since the nucleolus is involved in multiple cellular processes, it remains to be seen which specific processes influence the immune function. The present data discloses that the mechanism might be translation since the inventors observe translation reduction actively triggers pathogen resistance and Fibrillarin knockdown only modestly improves survival of mutants with reduced translation suggesting overlapping mechanisms. Fibrillarin is a highly conserved protein with similar structure and function in diverse species. Our study reveals a novel evolutionarily conserved function of Fibrillarin in regulating innate immunity in mammals. Human epithelial cells and macrophages show a down-regulation of Fibrillarin after 24 hours of infection, corroborating the results obtained in *C. elegans* and suggesting that reduction in Fibrillarin levels as an ancestrally conserved host-defense response towards infection. Depletion of Fibrillarin dampened the secretion of pro-inflammatory cytokines upon *S. aureus* infection, which also correlated with diminished cell death. Similarly, Fibrillarin knockdown in *C. elegans* stimulated irg-1 expression but not a general transcriptional inflammatory response. Inflammatory response to infection is required to defend against infection. However, overt inflammation makes the host susceptible to infection as a result of collateral damage to cells and tissues caused by the inflammatory cytokines. Therefore, pathogen resistance mechanisms encompass negative regulators of inflammation, which are required to elicit optimal host antimicrobial response. Moreover, fusion of the pathogen containing phagosome with lysosomes plays a vital role in containing infection, and inflammatory stimuli are also known to affect the process of phagosome maturation.

Consistently, the inventors also observed an increased co-localization of intracellular bacteria with lysosomes in cells bearing Fibrillarin knockdown. This intriguing observation points towards a possible role of Fibrillarin in mediating lysosomal biogenesis or acidification, which needs to be further investigated. Whether the observed reduction in pro-inflammatory cytokine generation and increased cell survival is a result of accelerated phagosome maturation, translation regulation, or other processes affected by Fibrillarin remains to be seen. Conceivably, Fibrillarin and related molecules could be used as vital targets for drug screens combating bacterial infections in mammals.

What is claimed is:

1. An in vitro method for determination of aging and metabolic health by a biomarker for aging and metabolic health and at least one further biomarker for aging, wherein the biomarker for aging and metabolic health is a nucleolar size, wherein the nucleoli are derived from blood cells, and the at least one further biomarker for aging is selected from the group comprising fibrillarin, TRIM2/3, and ribosomal proteins.

2. The in vitro method according to claim 1, wherein the biomarker for aging or metabolic health in humans is the nucleolar size.

3. The in vitro method according to claim 1, wherein the in vitro method is applied to test an effect of chemical compounds, medication, food and/or diet on life expectancy of humans.

4. The in vitro method according to claim 1, wherein virtual age is higher as the nucleolar size is smaller.

5. The in vitro method according to claim 1, wherein the at least one further biomarker for aging is fibrillarin.

* * * * *